(12) United States Patent
Wells et al.

(10) Patent No.: US 8,869,798 B2
(45) Date of Patent: Oct. 28, 2014

(54) FOAM-BASED INTERFACING STRUCTURE METHOD AND APPARATUS

(75) Inventors: Alicia Kristianne Wells, Bella Vista (AU); Lee James Veliss, Bella Vista (AU); Melanie Lucia Cariola, Bella Vista (AU); Fiona Catherine Carroll, Bella Vista (AU); Scott Alexander Howard, Frenchs Forest (AU)

(73) Assignee: ResMed Limited, Bella Vista (AU)

( * ) Notice: Subject to any disclaimer, the term of this patent is extended or adjusted under 35 U.S.C. 154(b) by 282 days.

(21) Appl. No.: 12/737,919

(22) PCT Filed: Sep. 3, 2009

(86) PCT No.: PCT/AU2009/001144
§ 371 (c)(1),
(2), (4) Date: Mar. 1, 2011

(87) PCT Pub. No.: WO2010/028425
PCT Pub. Date: Mar. 18, 2010

(65) Prior Publication Data
US 2011/0146684 A1     Jun. 23, 2011

(30) Foreign Application Priority Data

Sep. 12, 2008  (AU) ............................... 2008904769
Sep. 15, 2008  (AU) ............................... 2008904778

(51) Int. Cl.
*A62B 18/08*    (2006.01)
*A61M 16/06*    (2006.01)

(52) U.S. Cl.
CPC ........... *A61M 16/06* (2013.01); *A61M 16/0633* (2014.02); *A61M 2209/02* (2013.01)
USPC .................................................. 128/206.24

(58) Field of Classification Search
USPC ............ 128/206.24, 206.28, 205.25, 207.11, 128/207.13, 207.18, 206.21, 201.22
See application file for complete search history.

(56) References Cited

U.S. PATENT DOCUMENTS

| | | |
|---|---|---|
| 443,191 A | 12/1890 | Illing |
| 781,516 A | 1/1905 | Guthrie, Jr. |
| 1,081,745 A | 12/1913 | Johnston |
| 1,125,542 A | 1/1915 | Humphries |
| 1,192,186 A | 7/1916 | Greene |

(Continued)

FOREIGN PATENT DOCUMENTS

| | | |
|---|---|---|
| AU | 199651130 | 10/1996 |
| AU | 2005100738 | 11/2005 |

(Continued)

OTHER PUBLICATIONS

International Search Report issued in PCT/AU2009/001144 (Dec. 18, 2009).

(Continued)

*Primary Examiner* — Melanie Hand
*Assistant Examiner* — Ned T Heffner
(74) *Attorney, Agent, or Firm* — Nixon & Vanderhye P.C.

(57) ABSTRACT

A cushioning component for use with a mask is constructed of foam material. A patient contacting surface, that is adapted to contact a patient, in use, has a rounded cross sectional profile and a base surface opposed to the patient contacting surface.

17 Claims, 72 Drawing Sheets

(56) References Cited

U.S. PATENT DOCUMENTS

| | | |
|---|---|---|
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,749,910 A * | 6/1956 | Faulconer, Jr. .................. 601/44 |
| 2,931,356 A | 4/1960 | Schwarz |
| 3,013,556 A | 12/1961 | Galleher |
| 3,670,726 A | 6/1972 | Mahon et al. |
| 3,682,171 A | 8/1972 | Dali et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Tiep |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 10/1985 | Chien |
| 4,572,323 A | 2/1986 | Randall |
| 4,587,967 A | 5/1986 | Chu et al. |
| 4,601,465 A | 7/1986 | Roy |
| 4,617,637 A | 10/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,753,233 A | 6/1988 | Grimes |
| 4,767,411 A | 8/1988 | Edmunds |
| 4,774,946 A | 10/1988 | Ackerman et al. |
| 4,782,832 A * | 11/1988 | Trimble et al. .......... 128/207.18 |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | Amrhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,191,824 A | 3/1993 | Rathbun, Jr. |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,299,599 A | 4/1994 | Farmer et al. |
| 5,304,146 A | 4/1994 | Johnson et al. |
| 5,335,656 A | 8/1994 | Bowe et al. |
| 5,349,949 A | 9/1994 | Schegerin |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stern et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,560,354 A | 10/1996 | Berthon-Jones et al. |
| 5,570,684 A | 11/1996 | Behr |
| 5,592,938 A | 1/1997 | Scarberry et al. |
| 5,623,923 A | 4/1997 | Bertheau et al. |
| 5,626,814 A | 5/1997 | Vicino |
| 5,647,357 A | 7/1997 | Barnett et al. |
| 5,653,228 A | 8/1997 | Byrd |
| 5,655,527 A | 8/1997 | Scarberry et al. |

(56) References Cited

U.S. PATENT DOCUMENTS

| | | |
|---|---|---|
| 5,662,101 A | 9/1997 | Ogden et al. |
| 5,682,881 A | 11/1997 | Winthrop et al. |
| 5,704,345 A | 1/1998 | Berthon-Jones et al. |
| 5,707,342 A | 1/1998 | Tanaka |
| 5,724,965 A | 3/1998 | Handke et al. |
| 5,735,272 A | 4/1998 | Dillon et al. |
| 5,740,799 A | 4/1998 | Nielsen |
| 5,752,511 A | 5/1998 | Simmons et al. |
| 5,794,619 A | 8/1998 | Edelman et al. |
| 5,807,341 A | 9/1998 | Heim |
| 5,842,469 A | 12/1998 | Rapp et al. |
| 5,906,203 A | 5/1999 | Klockseth et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,019,101 A | 2/2000 | Cotner et al. |
| 6,026,811 A | 2/2000 | Settle |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,176,164 B1 | 1/2001 | Nylander |
| 6,193,914 B1 | 2/2001 | Harrison |
| 6,196,223 B1 * | 3/2001 | Belfer et al. ............ 128/206.25 |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 * | 3/2003 | Kwok et al. ............ 128/206.21 |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,860,270 B2 | 3/2005 | Sniadach |
| 6,895,965 B2 | 5/2005 | Scarberry et al. |
| 6,907,882 B2 | 6/2005 | Ging et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,951,218 B2 * | 10/2005 | Gradon et al. ............ 128/205.25 |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,191,781 B2 | 3/2007 | Wood |
| 7,207,328 B1 | 4/2007 | Altemus |
| 7,210,481 B1 | 5/2007 | Lovell et |
| 7,237,551 B2 | 7/2007 | Ho et al. |
| 7,243,723 B2 | 7/2007 | Surjaatmadja et al. |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam et al. |
| 7,523,754 B2 | 4/2009 | Lithgow |
| 7,658,189 B2 | 2/2010 | Davidson |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | DeVoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0124849 A1 | 9/2002 | Billette De Villemeur et al. |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1 | 12/2002 | Bishop |
| 2003/0000526 A1 | 1/2003 | Goebel |
| 2003/0019495 A1 | 1/2003 | Palkon et al. |
| 2003/0019496 A1 | 1/2003 | Kopacko et al. |
| 2003/0079749 A1 | 5/2003 | Strickland et al. |
| 2003/0089373 A1 | 5/2003 | Gradon et al. |

(56) References Cited

U.S. PATENT DOCUMENTS

| | | |
|---|---|---|
| 2003/0111080 A1 | 6/2003 | Olsen et al. |
| 2003/0154980 A1 | 8/2003 | Berthon-Jones et al. |
| 2003/0168063 A1 | 9/2003 | Gambone et al. |
| 2003/0196656 A1 | 10/2003 | Moore et al. |
| 2003/0196658 A1 | 10/2003 | Ging et al. |
| 2004/0025882 A1 | 2/2004 | Madaus et al. |
| 2004/0025885 A1 | 2/2004 | Payne, Jr. |
| 2004/0045551 A1 | 3/2004 | Eaton et al. |
| 2004/0065328 A1 | 4/2004 | Amarasinghe et al. |
| 2004/0106891 A1 | 6/2004 | Langan et al. |
| 2004/0107968 A1 | 6/2004 | Griffiths |
| 2004/0111104 A1 | 6/2004 | Schein et al. |
| 2004/0112384 A1 | 6/2004 | Lithgow et al. |
| 2004/0127856 A1 | 7/2004 | Johnson |
| 2004/0211428 A1 | 10/2004 | Jones |
| 2004/0226564 A1 | 11/2004 | Persson |
| 2004/0226566 A1 | 11/2004 | Gunaratnam et al. |
| 2005/0011523 A1 | 1/2005 | Aylsworth et al. |
| 2005/0028822 A1 | 2/2005 | Sleeper et al. |
| 2005/0033247 A1 | 2/2005 | Thompson |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0101933 A1 | 5/2005 | Marrs et al. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2005/0284481 A1 | 12/2005 | Meyer et al. |
| 2006/0060200 A1 | 3/2006 | Ho et al. |
| 2006/0081250 A1 | 4/2006 | Bordewick et al. |
| 2006/0095008 A1 | 5/2006 | Lampropoulos et al. |
| 2006/0095009 A1 | 5/2006 | Lampropoulos et al. |
| 2006/0118117 A1 | 6/2006 | Berthon-Jones |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0237017 A1 | 10/2006 | Davidson et al. |
| 2006/0237018 A1* | 10/2006 | McAuley et al. ........ 128/206.24 |
| 2006/0283461 A1 | 12/2006 | Lubke et al. |
| 2007/0023044 A1 | 2/2007 | Kwok et al. |
| 2007/0125387 A1 | 6/2007 | Zollinger et al. |
| 2007/0144525 A1 | 6/2007 | Davidson et al. |
| 2007/0186930 A1 | 8/2007 | Davidson et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110469 A1 | 5/2008 | Weinberg |
| 2008/0200880 A1 | 8/2008 | Kyvik et al. |
| 2008/0257354 A1 | 10/2008 | Davidson et al. |
| 2009/0044808 A1 | 2/2009 | Guney et al. |
| 2010/0000534 A1 | 1/2010 | Kooij et al. |
| 2010/0018534 A1 | 1/2010 | Veliss et al. |

FOREIGN PATENT DOCUMENTS

| | | |
|---|---|---|
| CN | 1553820 | 12/2004 |
| DE | 37 19 009 | 12/1988 |
| DE | 39 27 038 | 2/1991 |
| DE | 197 03 526 | 8/1998 |
| DE | 199 44 242 | 3/2001 |
| DE | 10002571 | 7/2001 |
| DE | 102 13 905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 0 303 090 | 4/1992 |
| EP | 0 658 356 | 6/1995 |
| EP | 0 776 679 | 6/1997 |
| EP | 1 099 452 | 5/2001 |
| EP | 1 258 266 | 11/2002 |
| EP | 1 481 702 | 12/2004 |
| FR | 2 720 280 | 12/1995 |
| GB | 532214 | 1/1941 |
| GB | 2 176 404 | 12/1986 |
| GB | 2 368 533 | 5/2002 |
| GB | 2376896 | 12/2002 |
| GB | 2 385 533 | 8/2003 |
| JP | 2000-515784 | 11/2000 |
| JP | 2009-520579 A | 5/2009 |
| WO | WO 82/03548 | 10/1982 |
| WO | WO 87/01950 | 4/1987 |
| WO | WO 92/20392 | 11/1992 |
| WO | WO 92/20395 | 11/1992 |
| WO | WO 96/28207 | 9/1996 |
| WO | WO 98/04310 | 2/1998 |
| WO | WO 98/12965 | 4/1998 |
| WO | WO 98/23305 | 6/1998 |
| WO | WO 99/16327 | 4/1999 |
| WO | WO 99/25410 | 5/1999 |
| WO | WO 99/43375 | 9/1999 |
| WO | WO 99/61088 | 12/1999 |
| WO | WO 00/20072 | 4/2000 |
| WO | WO 00/38772 | 7/2000 |
| WO | WO 00/50121 | 8/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/38221 | 5/2002 |
| WO | WO 02/45784 | 6/2002 |
| WO | WO 03/090827 | 11/2003 |
| WO | WO 03/105921 | 12/2003 |
| WO | WO 2004/022146 | 3/2004 |
| WO | WO 2004/041342 | 5/2004 |
| WO | WO 2004/073778 | 9/2004 |
| WO | WO 2004/078230 | 9/2004 |
| WO | WO 2005/053781 | 6/2005 |
| WO | WO 2005/063328 | 7/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | WO 2007/068044 | 6/2007 |
| WO | WO 2007/120355 A2 | 10/2007 |
| WO | PCT/AU2007/001936 | 12/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | PCT/AU2009/000262 | 3/2009 |
| WO | WO 2009/108994 | 9/2009 |

(56) References Cited

FOREIGN PATENT DOCUMENTS

| WO | WO 2009/109004 | 9/2009 |
|---|---|---|
| WO | WO 2010/028425 | 3/2010 |

OTHER PUBLICATIONS

Chinese Office Action issued in corresponding Chinese Application No. 200980136031.7 dated Feb. 27, 2013.
Examination Report for corresponding New Zealand Application No. 591308, mailed Jun. 21, 2012, 2 pages.
Patent Examination Report No. 1 issued in corresponding Australian Patent Application No. 2009291491 on Oct. 8, 2013.
U.S. Appl. No. 10/385,701, filed Aug. 2003, Berthon-Jones et al.
U.S. Appl. No. 10/533,928, filed Jul. 2005, Berthon-Jones.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
"Ear Loop Face Mask".
Adam J. Singer MD et al, "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
"If You Hate CPAP! You Need CPAP Prot®," www.cpappro.com.
Webster's New World Dictionary, Third College Edition 1988, definition for engaged and flexible.

EP Supplementary Search Report issued in EP Application 03793493, dated Dec. 2, 2009.
European Search Report filed on Jul. 27, 2009 in EP Application No. 07784697.0.
European Search Report issued in EP 07845378.4, mailed Dec. 1, 2009.
Examination Report filed in New Zealand Application 539836, dated Aug. 25, 2005.
Examiner's Report No. 3 mailed Nov. 18, 2009 in New Zealand Application No. 2003275762.
Extended European Search Report dated Mar. 19, 2009 in European Application No. EP 08161249.
Extended European Search Report Mailed Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http://www.rudolphkc.com/products.php?category=MASKS.
International Preliminary Report on Patentability for PCT/AU2004/001832, dated Jul. 3, 2006.
International Search Report filed in PCT/AU2005/000803, dated Jun. 30, 2005.
International Search Report filed in PCT/AU2006/000770, dated Aug. 3, 2006.
International Search Report for PCT/AU2007/001052, dated Oct. 9, 2007.
International Search Report for PCT/AU2007/001051, dated Nov. 5, 2007.
International Search Report for PCT/AU2004/001832, dated Mar. 24, 2005.
International Search Report for PCT/AU2007/001936, dated Mar. 4, 2008.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Office Action mailed Dec. 22, 2009 in European Appln. No. 04802133.1.
Office Action issued in Japanese Application No. 2007-513621 (Aug. 24, 2010) with English translation.
ResMed Co.—Mask Products—http://resmed.com/portal/site/ResMedUS/index.jsp?. . . .
Respironics Co.—Mask Family—http://masksfamily.respironics.com/.
SNAPP Nasal Interface, Tiara Medical Systems, Inc.—http://www.tiaramed.com/asp_shops/shopdisplayproducts.asp?id=109&cat=SNAPP%2A+Nasal+Interface.
Subbu Venkatraman et al., "Review Skin Adhesives and Skin Adhesion 1. Transdermal Drug Delivery Systems," Biomaterials, vol. 19, 1998, pp. 1119-1136.
Supplementary European Search Report mailed Sep. 8, 2009 in European Appln. No. 04802133.1.
Supplementary European Search Report mailed Dec. 18, 2009 in European Application No. 03810331.3.
Unsolicited email from Elson Silva, PhD, dated Mar. 28, 2008, "Requesting IDS of US 6,766,817 for patents on fluids moving on porosity by Unsaturated Hydraulic Flow," (email provided in both HTML and plain text format).
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
Office Action issued in European Appln. No. 05746824.1 (Mar. 22, 2011).

(56) References Cited

OTHER PUBLICATIONS

Notice of Reasons for Rejection issued in corresponding Japanese Application No. 2011-526353 on Oct. 8, 2013 with English-language translation.
Notice of Allowance issued Apr. 28, 2014 in corresponding Japanese Application No. 2011-526353.
Second Office Action issued in corresponding Chinese Application No. 200980136031.7 on Nov. 19, 2013 with English-language translation thereof.
Third Office Action issued in corresponding Chinese Application No. 200980136031.7 on Jun. 20, 2014 with English-language translation thereof (8 pages).

* cited by examiner

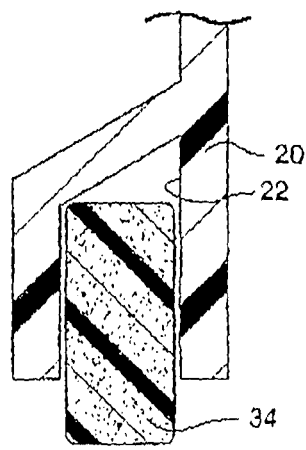
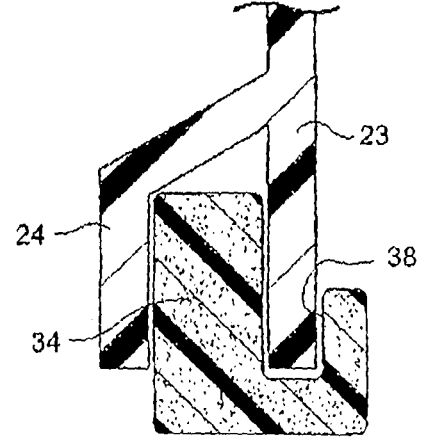
Fig. 2         Fig. 3a
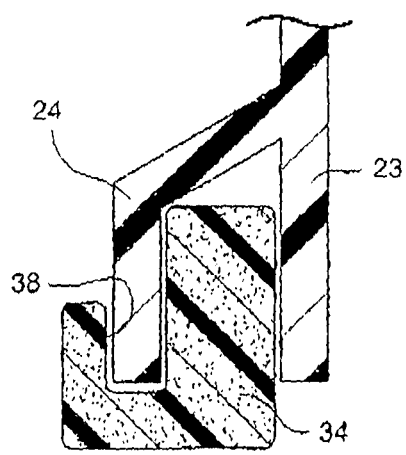
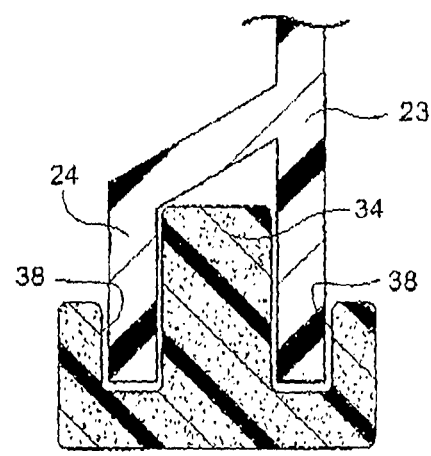
Fig. 3b        Fig. 3c

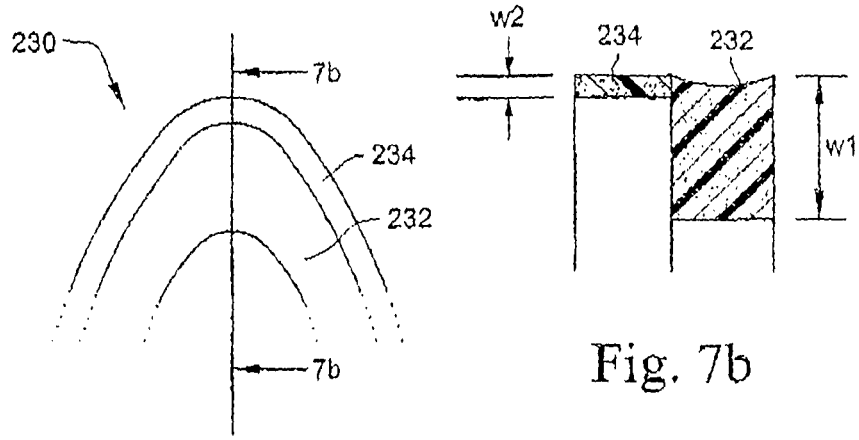
Fig. 7a
Fig. 7b
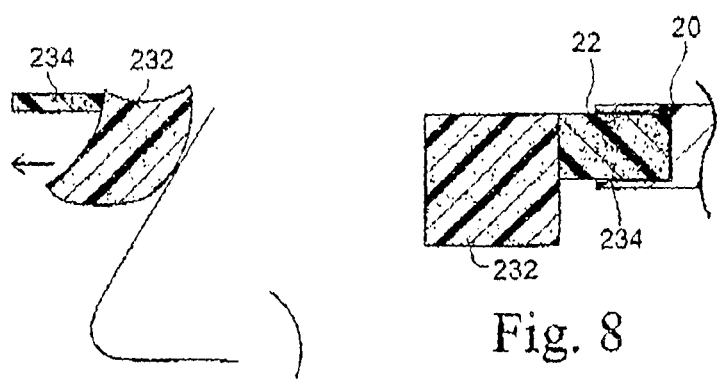
Fig. 7c
Fig. 8

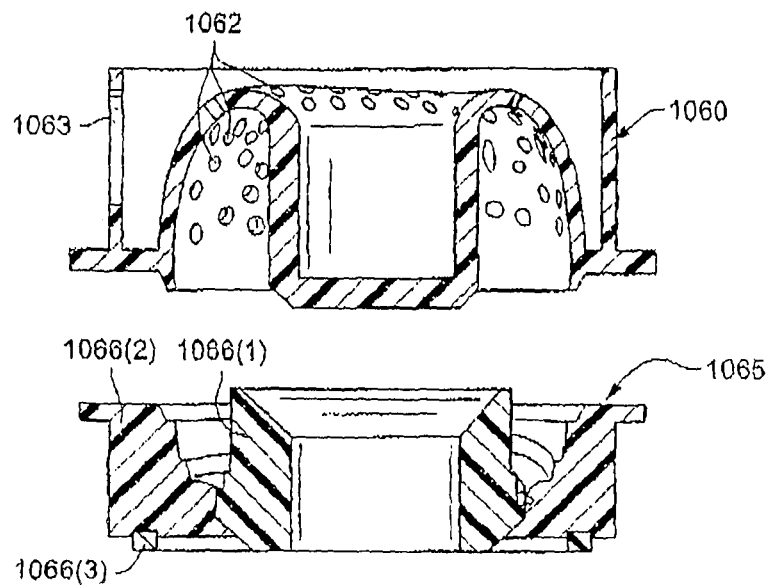
Fig. 17a
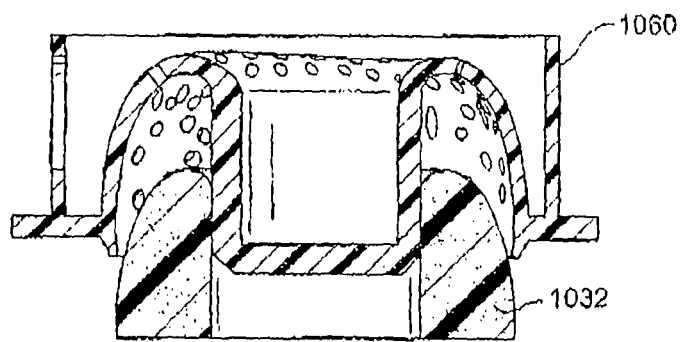
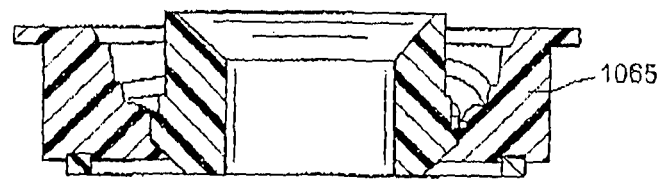
Fig. 17b

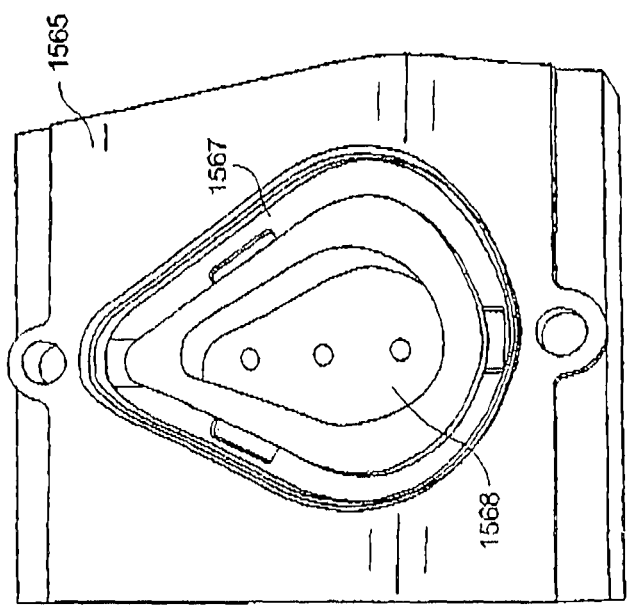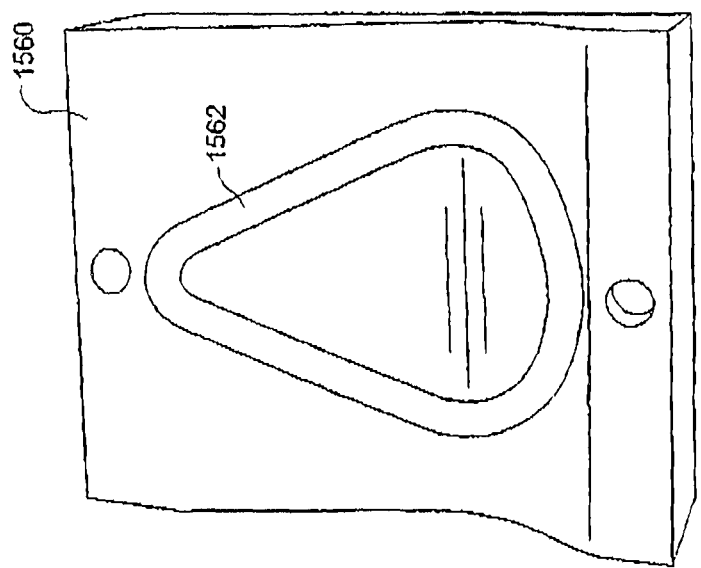
Fig. 18a

CUSHION FOAM

| MATERIAL PROPERTY | UNITS | 2nd PREFERRED RANGE | 1st PREFERRED RANGE | TEST STANDARD |
|---|---|---|---|---|
| Density | (kg/m^3) | 40 - 70 | 50 - 60 | DIN EN ISO 845 AS 2282.3 |
| Compression Set | (%) | 0 - 20 | < 2 | ISO 1856 AS 2282.9 |
| Tear Resistance | (N/m) | 100 - 500 | 200-350 | (AS 2282.7) |
| Tensile Strength | (N) | 10 - 30 | 15 - 22 | (AS 2282.6) |
| Elongation @ break | (mm) | 150 - 300+ | 200 - 300 | (AS 2282.6) |
| Tensile Stiffness | (N/mm) | 0.05 - 1.25 | 0.07 - 1.00 | Section 6 of specification |
| Hardness ILD @ 40% | (N) | 70 - 160 | 90 - 130 | (AS 2282.8) |
| Sealing Force @ 40% | (N) | 10 - 30 | 15 - 25 | TBA |
| Hysteresis | (%) | 25 - 35 | 2 - 50 | ISO 3385 - 1/2 |
| Relaxation @ 40% | (%) | 0 - 50 | 10 - 30 | TBA |
| Resilience (Rebound) | (%) | < 50 | <10 | AS 2282.11 |
| Cell Count | (Cells/cm) | 5 - 120 | 60 - 120 | (AS 2282.5) |
| Cell Structure | Homo/Heterogeneous (Cell Size - μm) | Homogeneous or Heterogeneous (20 - 4000) | Heterogeneous (20-1000) | N/A |
| Air flow | (L/sec at 400 Pa) | 0 - 1 | 0.2 - 0.5 | AS 2282.14 |
| Air permeability (annular sample) | (L/min at 40% compression 20 cmH2O) | 1 - 16 | 1 - 3 | Section 6 |
| Air permeability (cushion tested in mask form, all other leak paths sealed) | (L/min at 40% compression 20 cmH2O) | 0 - 25 | 0.5 - 8 | Section 6 of specification |

Fig. 48

CLIP FOAM (MICROCELLULAR PU)

| MATERIAL PROPERTY | UNITS | 2nd PREFERRED RANGE | 1st PREFERRED RANGE | TEST STANDARD |
|---|---|---|---|---|
| Air permeability | (L/m^2/s) | 0 - 5 | 0 | any |
| Density | (Kg/m^3) | 100 - 500 | 150 - 300 | DIN EN ISO 845 AS 2282.3 |
| Compression Set | (%) | 0 - 20 | 0 - 2 | ISO 1856 |
| Hardness ILD @ 40% | (N) | 10 - 100 | 30 - 60 | Shore O (or Shore A - TBC) |
| Resilience (Rebound) | (%) | > 50 | > 80 | AS 2282.11 |
| Cell Count | (Cells/cm) | | higher | (AS 2282.5) |
| Cell Structure | Homo/Heterogeneous (Cell Size - mm) | | small | N/A |

Fig. 49

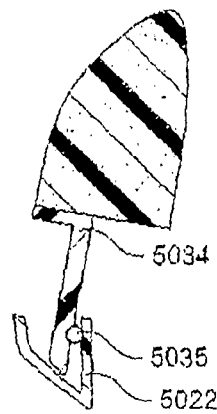 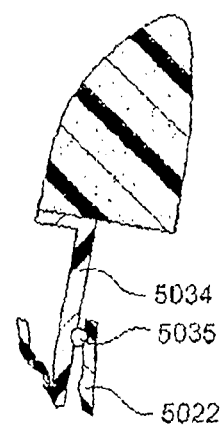
Fig. 52-1    Fig. 52-2
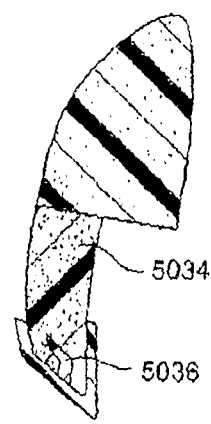 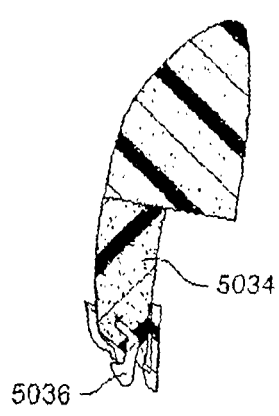
Fig. 53-1    Fig. 53-2

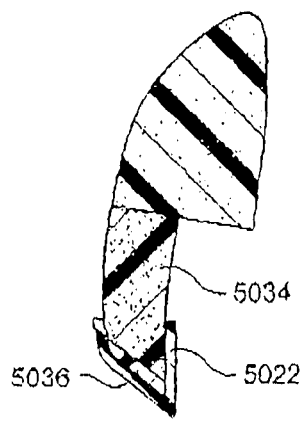 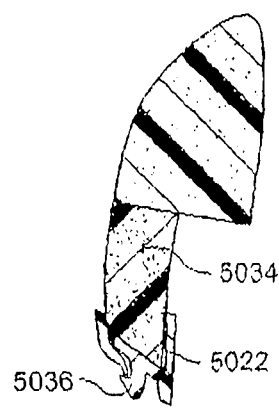
Fig. 54-1    Fig. 54-2
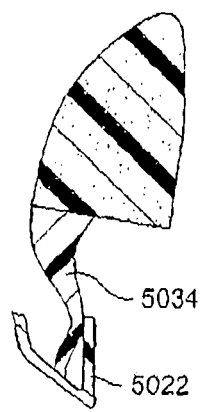 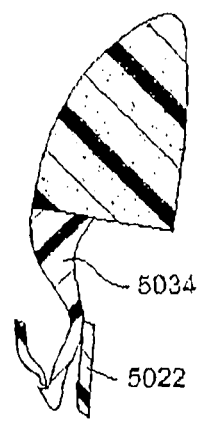
Fig. 55-1    Fig. 55-2

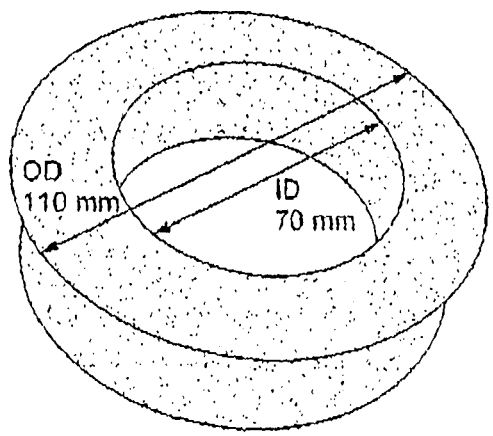
Fig. 60-1
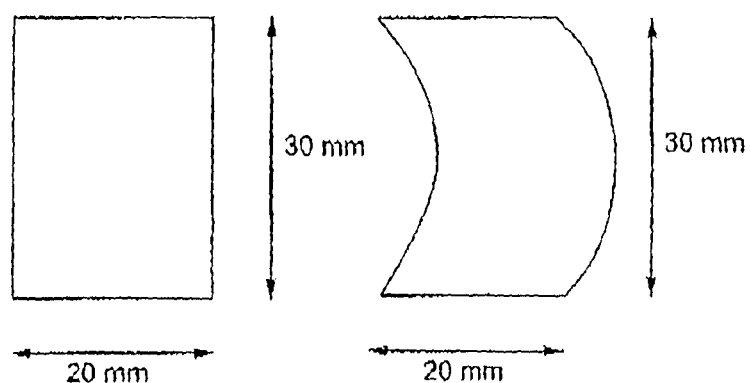
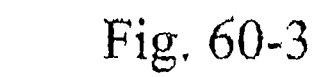
Fig. 60-2     Fig. 60-3

FOAM-BASED INTERFACING STRUCTURE METHOD AND APPARATUS

CROSS-REFERENCE TO APPLICATION

This application is the U.S. national phase of International Application No. PCT/AU2009/001144, filed Sep. 3, 2009, which designated the U.S. and claims the benefit of Australian Provisional Application Nos. AU 2008904769, filed Sep. 12, 2008, and AU 2008904778, filed Sep. 15, 2008, each of which is incorporated herein by reference in its entirety.

FIELD OF THE INVENTION

The present invention relates to an interface between a human and a piece of equipment, for example respiratory devices that include a foam-based interfacing structure.

BACKGROUND OF THE INVENTION

In a number of fields, such as respiratory therapy, apparatus for delivery of therapy includes a rigid component and a soft, cushioning component positioned between a patient and the rigid component.

In the case of a respiratory device, the rigid component may be a mask frame defining a nose and/or mouth-receiving chamber. The mask frame may include a flange around its periphery or other connecting means. The cushioning component may be glued or otherwise coupled to the flange or connecting means.

The cushioning component may form aa seal with the skin of the patient in some forms of respiratory therapy. In other devices, for example headphones, it may not be necessary for aa seal to be formed.

SUMMARY OF THE INVENTION

A first aspect of the invention is to provide a mask assembly with a foam interfacing structure.

Another aspect of the invention is to provide a mask assembly with a foam interfacing structure where at least a part of the foam (e.g., an unskinned part of the foam) is in direct contact with the skin of the mask user.

Another aspect of the invention is to provide a mask assembly with a foam interfacing structure where the foam is unskinned and has a cellular structure of the foam in direct contact with the skin of the mask user.

Another aspect of the invention is to provide a mask assembly with a removable foam interfacing structure.

Another aspect of the invention is to provide a mask assembly with at least two different types of removably replaceable interfacing structures.

Another aspect of the invention is to include a softer interfacing structure having portion adapted for engagement with a more rigid component.

Another aspect of the invention is to provide a respiratory mask assembly including a frame and an interfacing structure wherein the interfacing structure includes a foam-based cushion component and a clip portion adapted for removable engagement with the frame portion.

Another aspect of the invention is to provide a support structure for a cushioning component wherein the support structure supports the cushioning element on one side and allows movement on another side.

Another aspect of the invention relates to a cushion for a respiratory mask including a clip portion and a cushioning component wherein the cushioning component is constructed from a foam material and the clip portion is narrower than the cushioning component.

Another aspect of the invention relates to a respiratory mask assembly including a frame having a channel and an interfacing structure including a clip portion adapted for interference seal and retention in the channel. The interfacing structure includes a cushion component constructed from foam and having a wider width than the clip portion.

Another aspect is a foam-based cushioning component preferably having a first cross-section in a nasal bridge region, a second cross-section in a lip region and a third cross-section in the cheek region.

Another aspect is a method of manufacturing a cushioning component, e.g., die cutting and/or machining, etc.

Another aspect is a method of insert molding a clip component to a cushioning component to form an interfacing structure.

Another aspect is a cushioning component for use with a mask, wherein the cushioning component is constructed of foam material. A patient contacting surface, that is adapted to contact a patient, in use, may have a rounded cross sectional profile and a base surface opposed to the patient contacting surface.

Another aspect is a removable interfacing structure for use with a mask including a cushioning component constructed of foam material wherein a patient contacting surface that is adapted to contact a patient, in use, has a rounded cross sectional profile and a base surface opposed to the patient contacting surface is joined to a clip portion, and wherein the clip portion is adapted to be removably joined to a frame of the mask.

Another aspect is a mask including a removable interfacing structure and a frame, wherein the interfacing structure includes a clip portion and a cushioning component constructed of foam material having a patient contacting surface that is adapted to contact a patient, in use, has a rounded cross sectional profile and a base surface opposed to the patient contacting surface is joined to the clip portion, and wherein the clip portion is adapted to be removably joined to a frame of the mask.

Another aspect is a mask including a frame and an interfacing structure, wherein the interfacing structure includes a clip portion joined to cushioning component, and wherein the frame is more rigid than the clip portion and the clip portion is more rigid than the cushioning portion.

Another aspect is a cushioning component for use with a mask, wherein at least a portion of the cross section of the cushioning component includes an inner side defined by the side facing the centre of the mask, an outer side defined by a side facing away from the centre of the mask and a base side facing the frame or clip portion, wherein the length of outer side is greater than the inner side.

Another aspect is an interfacing structure for a mask including a clip portion joined to a cushioning component, wherein an upper surface of the clip portion is joined to a base surface of the cushioning component and wherein at least a portion of the upper surface is angled to provide a moment force on cushioning component, when force is applied into the cushioning component.

Another aspect is an interfacing structure for a mask including a clip portion joined to a cushioning component, wherein an upper surface of the clip portion is joined to a base surface of the cushioning component and wherein the cross sectional width of the clip portion is less than the cross sectional width of the cushioning component.

Another aspect is a cushioning component for use with a mask, wherein at least a portion of the cross section of the cushioning component includes an inner side defined by the side facing the centre of the mask, an outer side defined by a side facing away from the centre of the mask and a base side facing the frame or clip portion, wherein the outer side further includes at least an upper and a lower portion, wherein the upper portion is positioned at a reduced angle in comparison to the lower portion.

Another aspect is a nasal mask including a frame removably connected to an interfacing structure, wherein the interfacing structure includes a cushioning component constructed of foam material, and wherein the height of the interfacing structure is reduced in relation to region that is adapted to contact the upper lip region of a patient's face.

One aspect of the present technology relates to a respiratory mask including a frame, a foam cushion and a substructure. The mask includes a nose receiving cavity. The cushion includes at least two sides: an inner side wall, which may be a wall at least partially facing the cavity; and an outer side wall. The foam cushion is soft and conforming. The substructure is constructed from a more rigid material. The foam cushion is adapted to form a seal with at least one region of a face of a patient. In use the foam cushion is supported by the substructure. A connecting surface of the substructure is defined. A patient side of the foam cushion is defined. A non-patient side of the cushion is defined. In use the non-patient side of the cushion is arranged adjacent the connecting surface of the substructure. In one form the foam cushion is glued to the substructure. In another form the foam cushion is insert moulded with the substructure. A first region of the face is defined as a corner of the mouth of the patient. A second region of the face is defined as a chin region, or alternatively a lip region of the face of the patient. An interior region of the cushion is defined as the region or cavity into which a nose of a patient is inserted in use.

In one form, a part of the connecting surface in use adjacent the first region is structured in to direct a corresponding portion of the foam cushion in an inward direction towards the interior region of the cushion in the first region in use. The cross-section of the cushion defines a radial axis and a longitudinal axis is normal to said radial axis. Preferably, at least a portion of the foam cushion is adapted to rotate towards the centre of the mask about said longitudinal axis when pressure is applied into the cushion by the patient's face and wherein at least a portion of the outer side wall of said cushion is adapted to form a seal against the face of a patient.

Wherein portions of the cushion rotate or roll inwards towards the centre of the mask. The feature of rolling or rotating inwards may prevent or limits the possibility of the seal "blowing out" when air pressure is applied to the mask cavity, "Blowing out" is defined by the seal between the cushion and the patient's face breaking due to pressure exerted by air pressure lifting the cushion from a sealing relationship with the face.

In one form, a part of the connecting surface in use adjacent the second region is structured to direct the foam in an outward direction away from the interior region of the cushion in the second region in use. The cross-section of the cushion defines a radial axis and a longitudinal axis is normal to said radial axis. Preferably, at least a portion of the foam cushion is adapted to rotate away from the centre of the mask about said longitudinal axis when pressure is applied into the cushion by the patient's face and wherein at least a portion of the outer side wall of said cushion is adapted to form a seal against the face of a patient.

Preferably, further portions of the cushion may rotate inwards or outwards relative to the centre of the mask in positions defined as being proximal to the patient's chin. In regions or portions of the cushion that can rotate or roll inwards and outwards, this rotation may allow for seal to accommodate different sizes of chin and/or accommodate moderate amounts of mouth or jaw movement that may otherwise destruct the seal formed between the mask and the patient's face.

Another aspect of the present technology is a foam cushion for a respiratory mask wherein the cushion includes a face-contacting portion arranged in use to be adjacent the face of the patient.

Preferably in at least some regions of the face contacting portion, a cross section of the cushion tapers from a wider cross-section to a narrower cross-section closer to the face. The tapered portion defines an inside surface adjacent an interior of the cushion and an outside surface. The inside surface and the outside surface may be adjacent, in another form they may be non-adjacent. The inside and outside surfaces may be arranged at an acute angle with respect to one another. In one form in cross-section the outside surface is longer than the inside surface in certain regions of the cushion, preferably in the nasal bridge region, or in the cheek region, or more preferably in both. In one form the inside and outside surfaces have the same length in a chin region. In one form in a lip region the inside surface is longer than the outside surface in cross-section.

In one form, the cushion is structured to at least partially form a seal on an outside surface of a face in a chin region of the cushion. We have found that a tapered sealing portion may improve the seal.

Other aspects are directed to methods for manufacturing the foam cushioning elements described above.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 3a, 3b, and 3c show a range of rib engagement fitting arrangements between a mask frame and a clip portion of an interfacing structure according to embodiments of the invention;

FIG. 4b shows a bottom view of the interfacing structure of FIG. 4a;

FIG. 4c shows a top view of the interfacing structure of FIG. 4a;

FIG. 4d shows a side view of the interfacing structure of FIG. 4a;

FIG. 4e shows a frame contacting side of the interfacing structure of FIG. 4a;

FIG. 4f shows a patient contacting side isometric view of the interfacing structure of FIG. 4a;

FIG. 4g shows a frame contacting side isometric view of the interfacing structure of FIG. 4a;

FIG. 5b is an isometric view of the interfacing structure shown in FIG. 5a;

FIG. 6b shows a detail in the nasal bridge region of the mask of FIG. 6a;

FIG. 7a shows an elevation view detail from the frame side of the interfacing structure shown in FIG. 4e;

FIG. 7b is a cross-section along line 7b-7b of FIG. 7a;

FIG. 7c is a cross-sectional view showing the interfacing structure of FIGS. 7a and 7b in use;

FIG. 8 is a cross-sectional view showing the assembly of the interfacing structure of FIGS. 7a and 7b and a frame according to an embodiment of the invention;

FIGS. 10a to 10e show various views of a foam-based interfacing structure according to another embodiment of the present invention;

FIGS. 17a to 17h illustrate a tool and manufacturing process for manufacturing an interfacing structure according to an embodiment of the present invention;

FIGS. 18a to 18c show various views of a tool for molding a clip portion according to an embodiment of the present invention;

FIG. 29 defines a horizontal plane of connection between the cushion and the clip portion. In FIGS. 30 to 32 the plane of connection is at an angle with respect to the horizontal, In FIG. 30 the plane of connection is at a downward angle when moving from the outside to the inside of the interfacing portion, in FIG. 32 the plane of connection is at an upward angle when moving from the outside to the inside of the interfacing portion.

FIG. 48 is a chart showing exemplary material properties for a cushion component according to an embodiment of the invention;

FIG. 49 is a chart showing exemplary material properties for a clip portion according to an embodiment of the invention;

FIGS. 50-1 to 57-2 illustrate alternative mechanisms for attaching a clip portion to a frame according to embodiments of the invention;

FIGS. 60-1 to 60-8 illustrate different parameters and apparatus for testing air permeability according to an embodiment of the invention;

FIGS. 62-1 to 62-2 illustrate different parameters and apparatus for testing tensile strength according to an embodiment of the invention;

FIGS. 63-1 to 63-4 illustrate different parameters and apparatus for testing tear resistance according to an embodiment of the invention.

DETAILED DESCRIPTION OF ILLUSTRATED EMBODIMENTS

Figure 1:
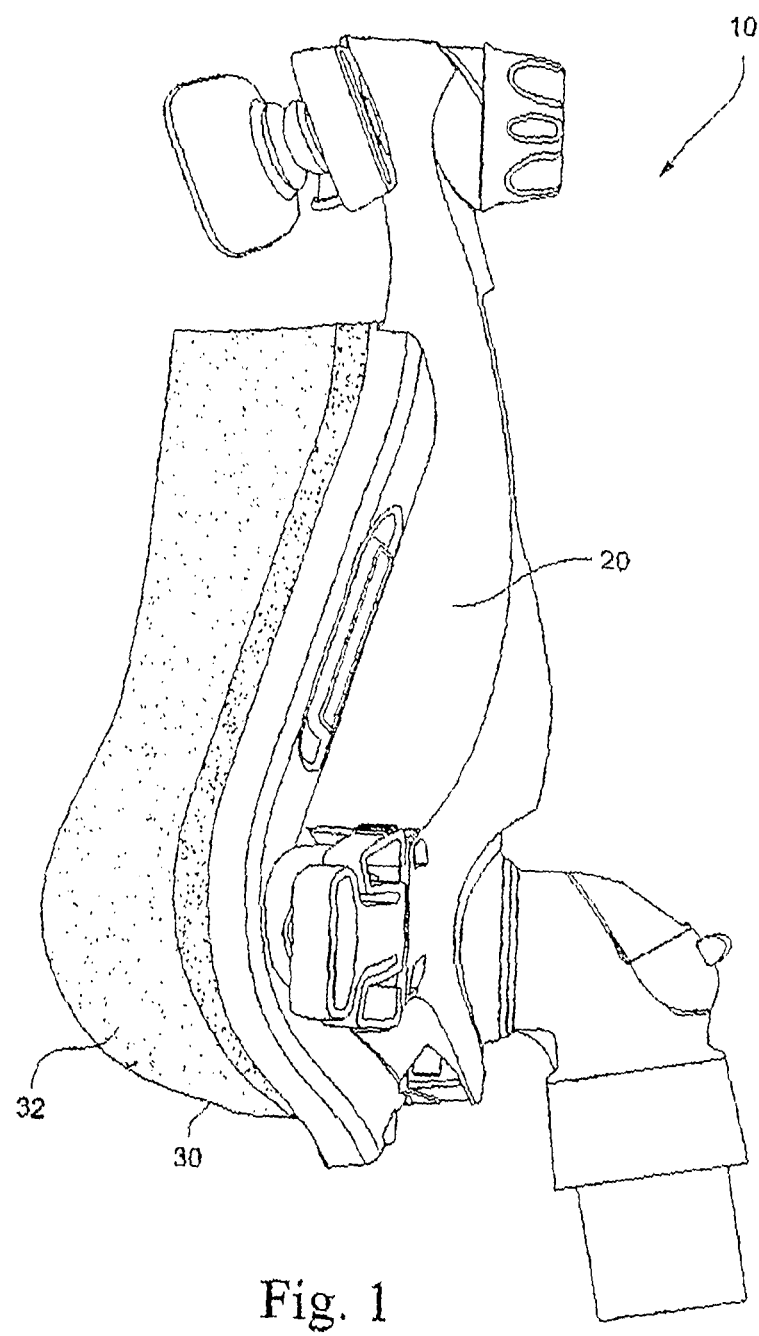
FIG. 1 shows a side view of a mask assembly including a foam interfacing structure according to an embodiment of the invention.

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

The term "seal" will be taken to mean to reduce the flow of air between the pressurized interior of the mask and the ambient conditions to a level sufficient to maintain a therapeutic pressure in the airways to effect treatment. Hence in some cases, there may be an air tight seal, in other cases there may be a small leak.

1. Introduction

A mask assembly used to facilitate the delivery of a supply of air or breathable gas to the entrance of the airways of a patient typically includes a generally soft, conforming interfacing structure, at least a portion of which is in contact with the patient's face and a stabilizing structure that positions and retains the interfacing structure in a suitable position with respect to the patient. The mask assembly typically includes some form of anchor point to which various components may be connected, or about which they may be arranged. In this specification, this anchor point will be referred to as the frame.

By way of example, the stabilizing structure of the mask assembly may be called "headgear" and both the headgear and interfacing structure may be connected to a frame. In some forms of mask, the boundary lines between the different components may be blurred. For example, aspects of frame and headgear may be combined.

The interfacing structure may perform two or more functions: (i) a cushioning function, performed by a cushioning component, and (ii) an interconnection function, performed by a cushion-to-frame component or clip portion. Generally, in this specification the term "clip" or "clip portion" may describe the aforementioned clip portion or a cushion to frame component for securing the cushioning component to a frame of a mask.

Forming the interfacing structure from two separate elements enables each to have different properties, such as different densities or air permeabilities as suits their different roles, as will be described in more detail in the following sections. Furthermore, the different properties of different materials can act to influence the other component. For example, a more rigid clip or cushion-to-frame portion can act as a support structure for a softer cushioning component.

However, in another embodiment, the interfacing structure may be constructed from a single component with different properties in different regions of the interfacing structure. Furthermore, the interfacing structure may be formed from more than two components.

The interfacing structure may be constructed and arranged to apply air or breathable gas to both the nose and mouth (a "nose & mouth" or "full-face" mask), or to the just the nose (a "nose" or "nasal" mask), or just the mouth (a "mouth" mask).

The statement "more rigid" may be understood to mean less flexible and/or stiffer.

2. Cushion Component

2.1 Material

In one form, the cushioning component may be made from an unskinned, low density, permeable foam. In a preferred embodiment, the cushion component is constructed from a low resilience viscoelastic polyurethane foam. The cushioning component material may be manufactured from a free rising slabstock foam process. In other embodiments the material may be manufactured by other processes such as molding or other known processes used to produce soft and cellular materials. One or more fabrication steps (known as conversion techniques) may then be applied to the material to partially or completely form the geometry of the cushion component. These conversion techniques are described herein and in other related specifications referenced herein. Such a foam material and conversion techniques are disclosed in PCT Publication Nos. WO 2008/011682, published Jan. 31, 2008, and WO 2008/070929, published Jun. 19, 2008, each of which is incorporated herein by reference in its entirety. In one form, the cushioning component may be formed in whole or in part by a known method such as die cutting. Die cutting is disclosed in PCT Application PCT/AU2009/000262, filed Mar. 4, 2009. In another form the cushioning component may be formed in whole or in part by using other methods such as those disclosed in AU 2008904769 and AU 2008904778.

Most foam material production techniques produce a material that has a substantially skinned material such that the density of the material at the surface is greater than the density of the material's bulk (internal) properties. The utilization of particular manufacturing techniques, such as foam conversion processes involving cutting, may allow the production of a unskinned cushioning component such that the bulk properties of the cellular material are exposed at the surface of the cushioning component, providing a number of advantages to the design, manufacture and performance of the mask assembly.

The unskinned cushion component provides improved sealing, comfort and fit range performance, sealing properties sufficient to not require a silicone membrane, and a unskinned mask assembly that allows utilization of the bulk properties of the unskinned material, e.g., porosity for breathability, fine cell structure for a comfortable feel.

2.2 Shape

The interfacing structure is preferably constructed and arranged to have a three dimensional shape defined in part by a locus of points surrounding and complementary to the entrance to the relevant airways. Furthermore, the interfacing structure has a cross-section chosen at different points around its perimeter to provide efficacy and comfort by being suitably shaped to adapt and conform to the face of the user forming a compression-type seal. In another configuration, a flap-type seal is formed.

The shape of the interfacing structure may be adapted to allow the cushioning component to provide a better fit and seal against the face of the patient.

In an embodiment, the geometry of the cushion may be at least partly determined by the geometry of the frame to which it is to be attached. For example, the general shape of a small size cushion may be different than the general shape of a large size cushion because the small and large size frames may be different, e.g., the small may be more stout or wide while the large may be more elongated and thinner.

2.2.1 Full Face Mask

Figure 16A:
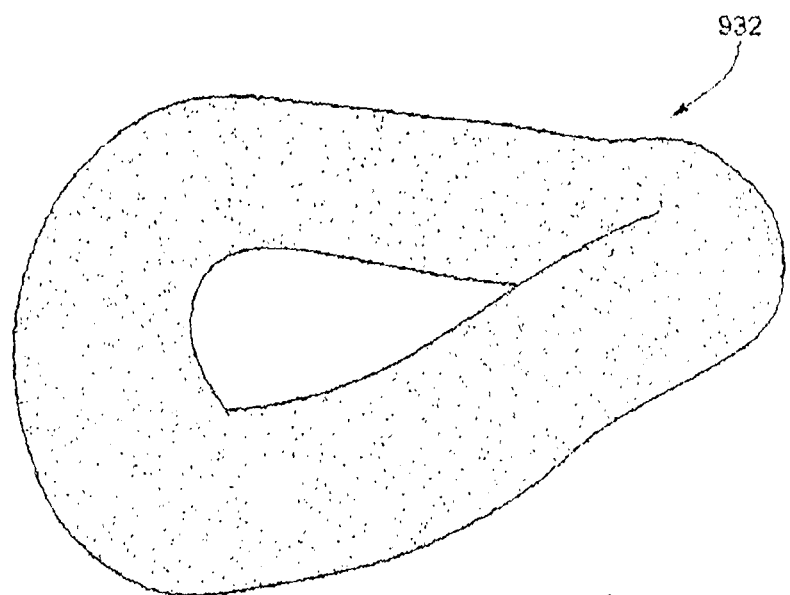
FIGS. 16a to 16i show various views of the cushioning component of the interfacing structure shown in FIGS. 14a to 14f.
Figure 16B:
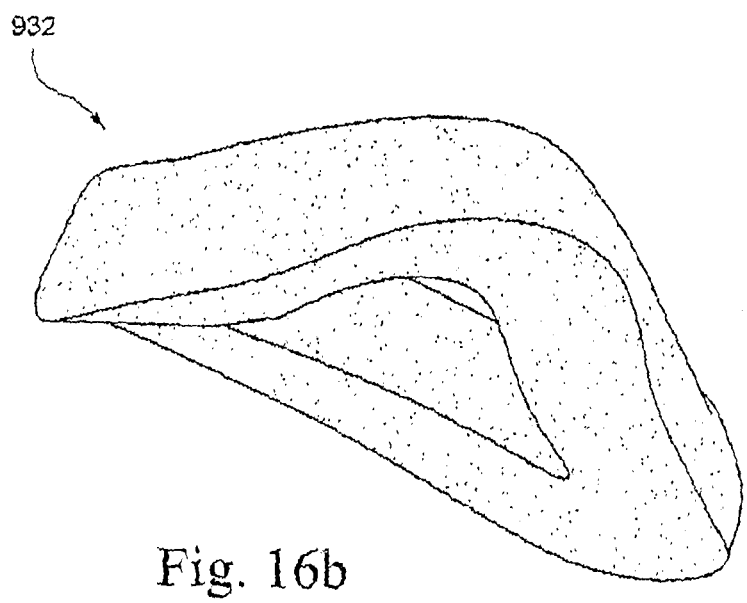
Figure 16C:
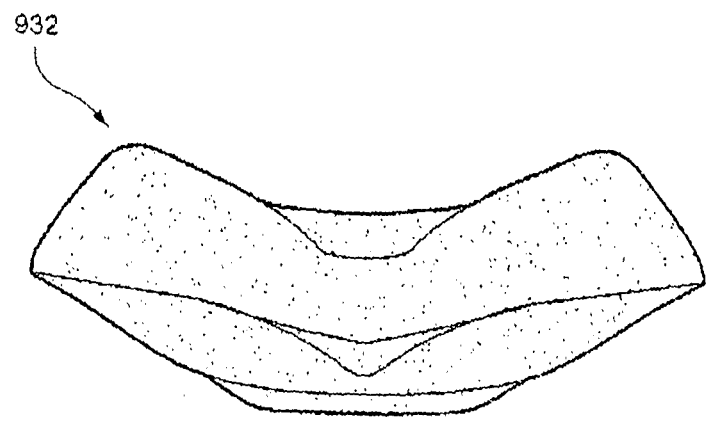
Figure 16D:
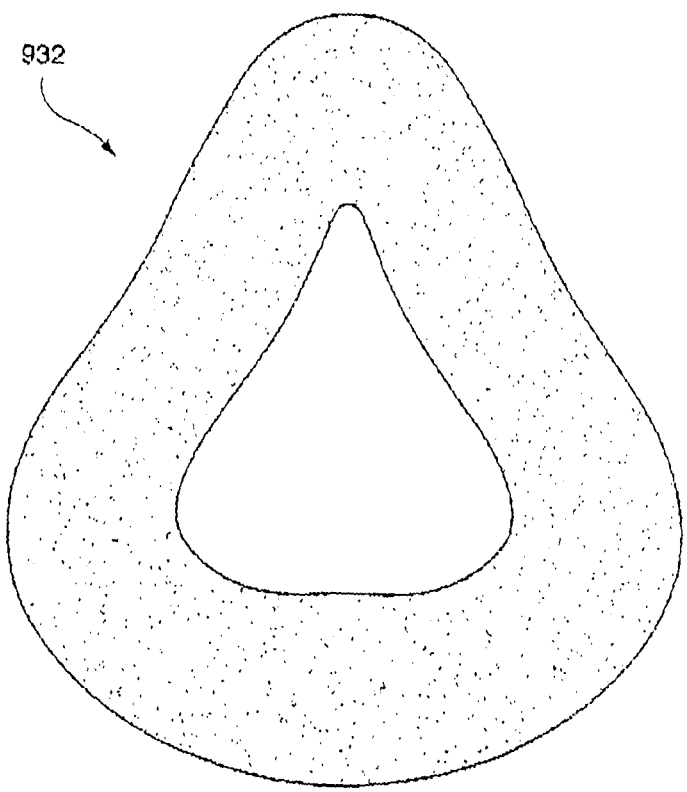
Figure 16E:
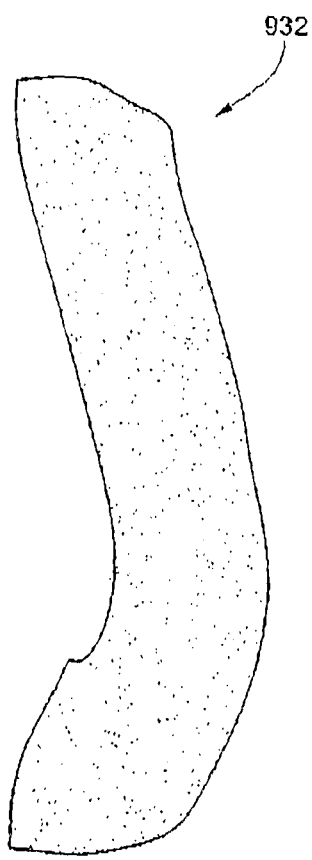
Figure 16F:
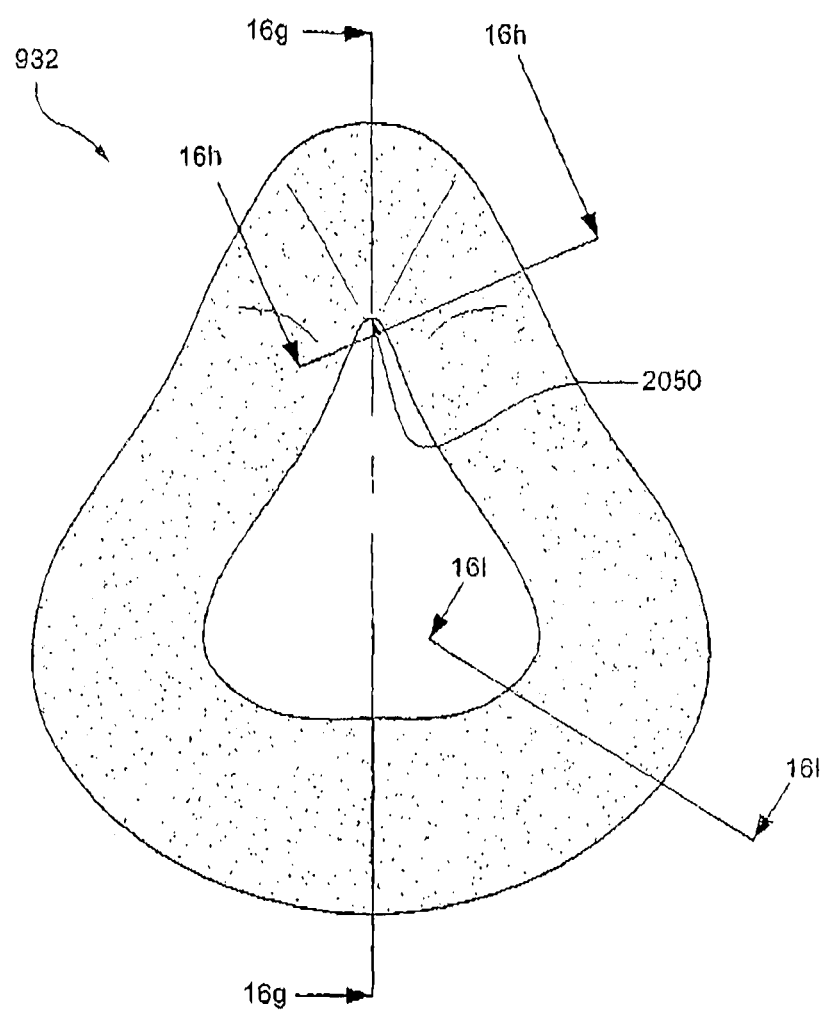
Figure 16G:
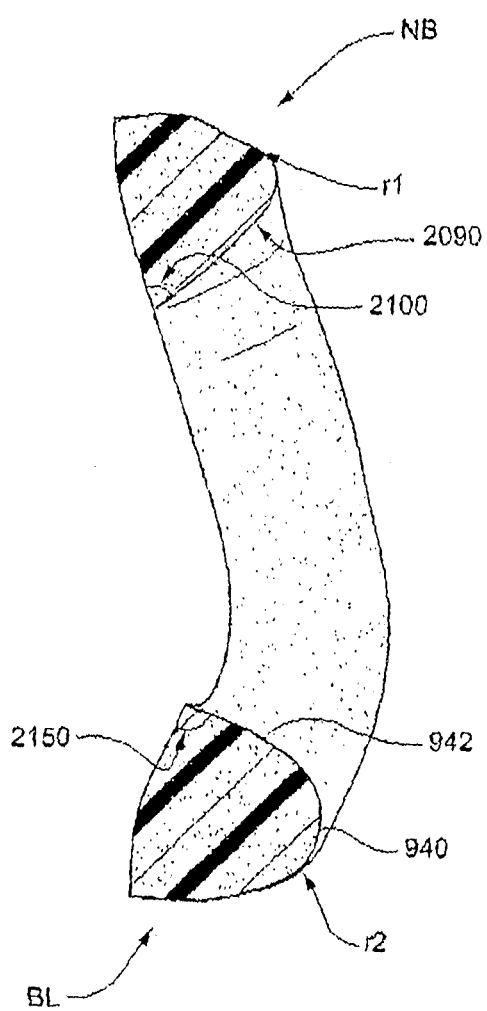
Figure 16H:
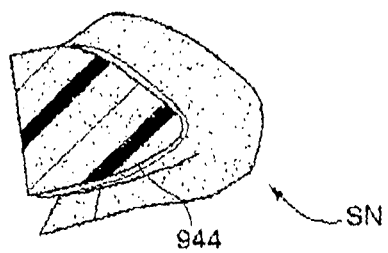
Figure 16I:
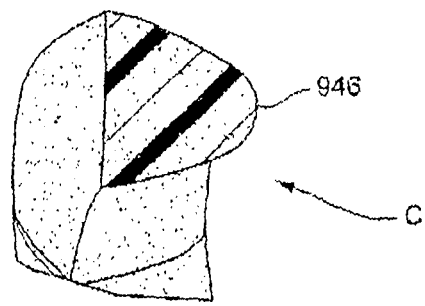
Figure 19:
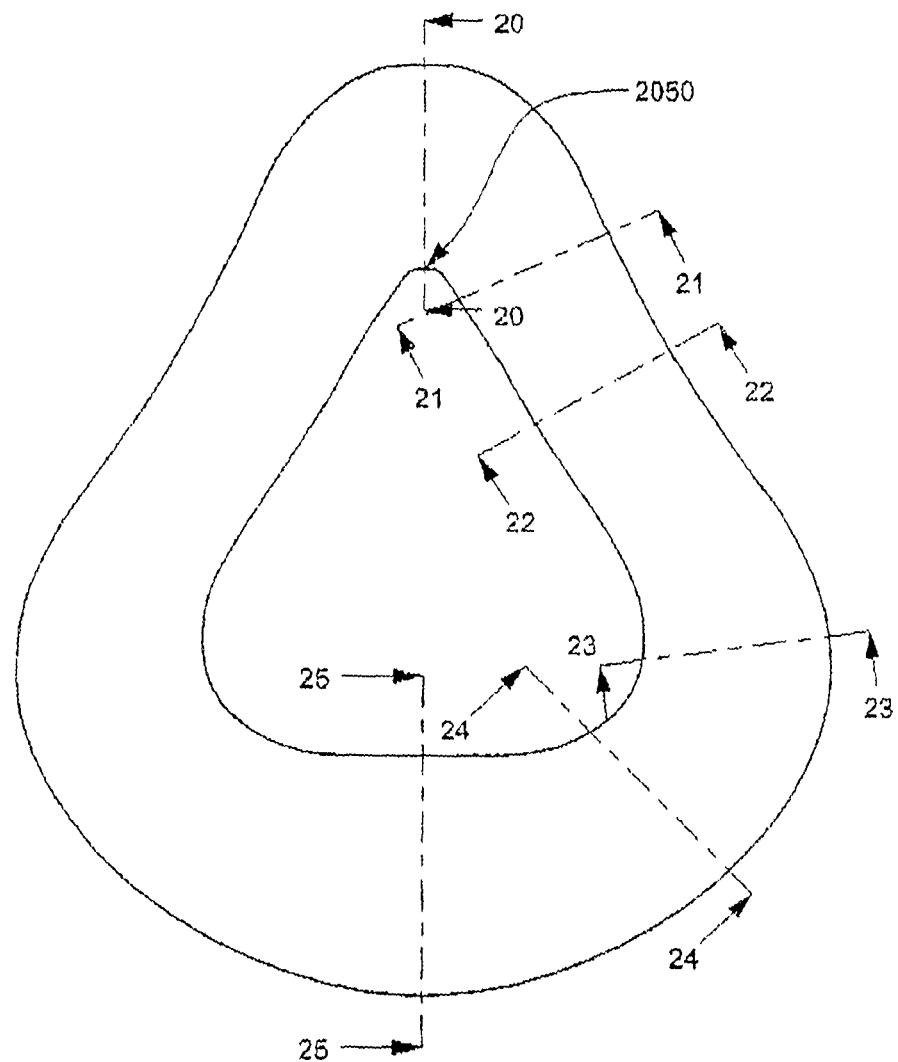
FIG. 19 is a front view of a further embodiment of a full face cushioning component.

FIGS. 16g to 16i show various cross-sections through one embodiment of the cushioning component 932 (origin of cross section shown in FIG. 16f), FIG. 19 shows an alternative embodiment of the present invention with corresponding cross sections in FIGS. 20-25.

FIGS. 33-38 depict a further preferred embodiment of a interfacing structure wherein the interfacing structure includes a co-molded or otherwise attached cushioning component and a clip portion Preferably, the full face masks depicted in this specification may have cushioning components about 105-110 mm in width (as measured from the outer most edges of the base surfaces); and a length of between 120-150 mm.

Nasal Bridge Region

Figure 20:
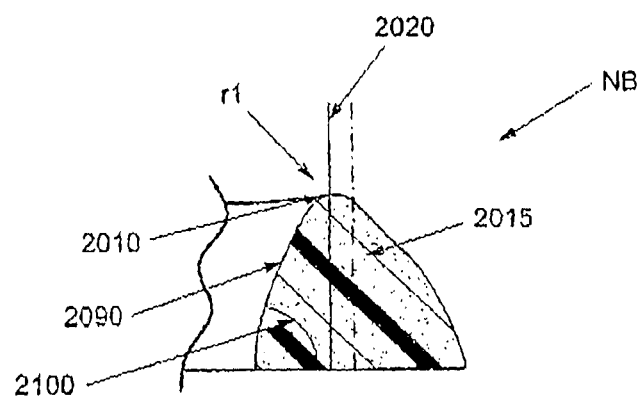
FIGS. 20-25 depict various cross-sectional views of the embodiment shown in FIG. 19.

As shown in FIG. 16g, the cross section at the nasal bridge region NB is generally triangular. The cross section at the nasal bridge region NB may also be another other reasonable shape, such as generally rectangular, oval, octagonal etc. In addition, it is possible for the cross section at the nasal bridge region to include a shape with generally rounded or curved corners. The cross section at the nasal bridge region may also be an irregular shape. FIG. 20 shows an alternative cross section for the nasal bridge region.

There is a radius r1 at the apex 2010 of the cross section, that may be relatively small or sharp radius at the nasal bridge region NB. For example, radius r1 may be between 1 to 4 mm. This relatively small or sharp radius at radius r1 provides the advantage that the cushioning component is kept away from the patient's eyes, especially when the cushioning component is compressed and inflated with air pressure in use. The relatively small or sharp radius at radius r1 may also enable minimal contact of the mask with the patient's skin, so as to make the mask feel more comfortable and less obtrusive.

As best shown in FIG. 20, apex 2010 of the generally triangular cross section may be skewed or offset. The apexes or the corners of the generally triangular cross sectional may be rounded to promote a better fit with the patient and/or a better seal. This offset is shown on FIG. 20, where apex 2010 and center line 2015 are spaced by distance 2020. Distance 2020 may be preferably around 1-2 mm at the position proximal to the patient's nose. The comparable offset in the cushioning component about the portion adapted to cover the bottom lip of the patient is preferably 8 mm. The comparable offset in the cushioning component about the portion adapted to cover the cheeks of the patient is preferably 1.25 mm. FIG. 20 demonstrates an offset towards the inner edge of the cushioning component. Alternatively the apex may be skewed, or over the outer edge of the cushioning component.

Additionally, the generally triangular cross section of the cushioning portion may also additionally be defined has having three sides: an inner side which faces into the centre of the mask; an outer side facing away from the centre of the mask and a base surface, which may be adapted to be joined to a clip portion, at least in part.

The outer side of surface of the cushioning portion is generally adapted to be longer than the inner surface. This may allow the cushioning component to, in effect, roll, bend or move inwards. The rolling motion leads to an extension of the sealing surface formed between the skin of the patient and the cushioning component. As the cushioning component is depressed, the contact region against the patient's skin is lengthened from the minimum contact point which is the apex to at least partially extending along the outer surface or side of the cushioning component.

Figure 58:
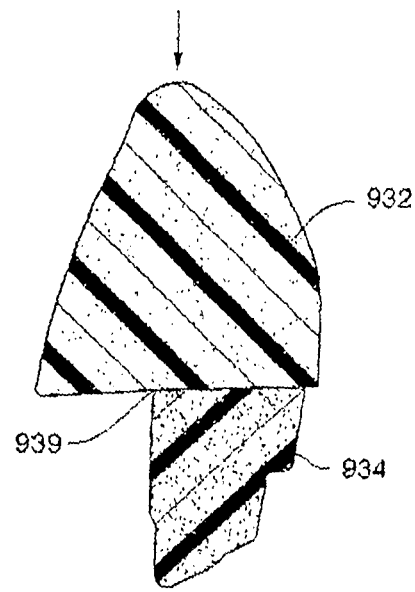
FIGS. 58 and 59 illustrate the rolling effect of a cushioning component according to an embodiment of the invention.
Figure 59:
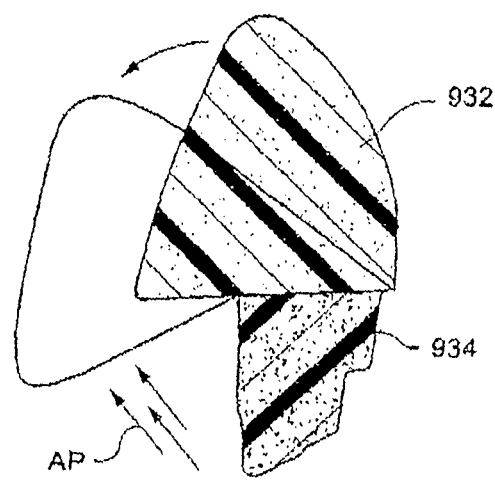

For example, the apex of the triangle that contacts the user's face (FIG. 58) enables the cushion component 932 to deflect or roll such that if the apex is towards the inner part of the cushion component, the cushion component will roll inwards and over the clip portion 934 about hinge point 939. Air pressure AP from the CPAP device (FIG. 59) acts on the back of the rolled section of the cushion component 932 such that the air pressure forces the cushion component into sealing engagement on the patient's face.

The rolling effect or the turning moment force, when the mask is pressed onto the face, can be also increased or assisted the positioning or shape of the clip portion attached to the cushioning portion. Preferably, the clip portion 3234 may be joined to the base surface of the cross section of the cushioning component. More preferably, the clip is mounted proximal to the outer side of the cushioning component, and provides little or no support relative to the inner side of the cushioning component. Preferably, the clip portion may not generally support the inner side of the cushioning component.

Preferably, the clip portion includes a stepped configuration when viewed in accordance with its cross section. In FIGS. 27-32, a preferred clip portion is joined to a cushioning portion. The stepped configuration is adapted to mate with a corresponding groove, slot or recess in the frame to provide aa seal. In this embodiment, the step formation is oriented towards the outer side of the cushioning component for ease of use by the patient.

Preferably, the clip portion is joined to the cushioning component by an upper side. The upper side of the clip portion may be shaped to assist with: sealing of the cushioning component; comfort; and/or the aforementioned rolling effect of the cushioning component. In FIGS. 30-31, the upper side of the clip portion has been angled towards the centre of the mask by lengthening the outer side of the clip portion relative to the shorter inner side of the clip portion. This angling of the upper surface of the clip portion is adapted to aid or assist in the rolling in effect of the cushioning component. Additionally, in the embodiments shown in FIGS. 26-32, the angled upper side of the clip portion has been included on the lower corners of the mask. For example, as shown in FIGS. 30 and 31, the upper surface of the clip portion is angled to enhance rolling and sealing in lower cheek and lip regions (e.g., a1 and a2 between about 0-20°). As shown in FIG. 32, the angle of the upper surface in the chin region (e.g., a3 between about 0-20°) is oriented opposite that in the lower cheek and lip regions (e.g., the bottom lip region) (FIGS. 30 and 31), e.g., for manufacturability.

Preferably, the upper corner which is adapted to engage the nasal bridge of the patient, the upper surface of the clip portion is flat and not angled towards to the centre of the mask. This is generally because the region around the nose doesn't require as much "roll" as the sealing area against the sides of the nose is relatively long compared the regions around or about the cheeks of the patient. This feature is demonstrated in FIGS. 27 and 28.

Preferably, the nasal bridge region also includes a modification to the base surface, wherein the base surface has been reduced or shortened to thereby reduce the volume of foam material rolled inwards at the nasal bridge.

FIG. 32 depicts the interfacing structure wherein the upper surface of the clip surface has been angled outwards relative to the centre of the mask. This reduces the effect of "roll in" in the predetermined regions including this outwardly disposed angle of the upper surface. Generally, the outwardly disposed angle of the upper surface is suitable for regions requiring reduced "roll in" such as around the bottom lip or around the upper lip (in the nasal mask configurations). Another way to regulate "roll in" is by changing the amount of overhang of the cushioning component with respect to the clip portion.

As shown in FIG. 16f, the inner apex 2050 of the cushion has the radius of curvature of between 3 to 10 mm (most preferably 3-5 mm). This is similarly shown in FIG. 19, where the inner apex 2050 of the cushion has the radius of curvature. The size of this radius may affect the durability, and more specifically the tear strength of this region.

As shown on FIGS. 16g and 20, inner edge 2090 may have an angle 2100 from the base of the cushioning component. Angle 2100 may influence the amount of the cushioning component that may contact the patient. For example, angle 2100 shown in FIG. 16f may be larger than angle 2100 shown in FIG. 20, such that more of the cushioning component in FIG. 16f may contact the patient's face than that of FIG. 20. Preferably, angle 2100 may be about 90-95 degrees. The angle of the outer side or edge meeting the base surface is preferably between 78-83. Preferably, the angle by which the outer side meets with the base surface is generally less than the angle formed between the inner side and the base surface.

The most preferred maximum width of the nose bridge region (as measured along the base surface) is 22 mm and most preferred maximum height of the cushioning component at the nose bridge position is approximately 24 mm.

Bottom Lip Region

Figure 25:
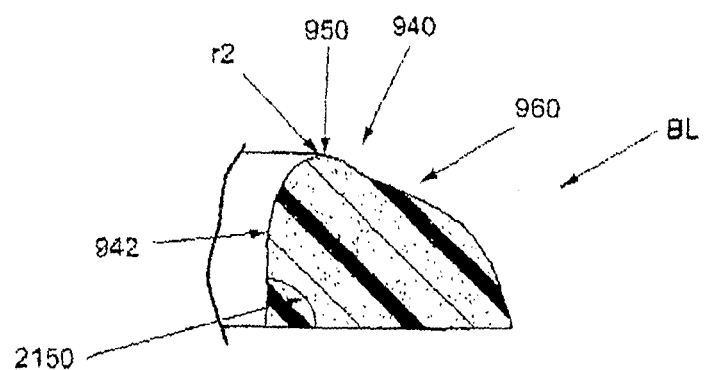

As shown in FIG. 16g, the cross section at the bottom lip region BL may preferably be generally trapezoidal. The cross section at the bottom lip region BL may also be another other reasonable shape, such as generally rectangular, oval, octagonal etc. In addition, it is possible for the cross section at the bottom lip region to include a shape with generally rounded or curved corners. The cross section at the bottom lip region may also be an irregular shape. FIG. 25 demonstrates this feature in a cross section for the bottom lip region.

Preferably, in the embodiment depicted in FIG. 25, the apex 950 is skewed towards the centre of the mask, the outer side or surface of the cushioning component at the region that is adapted to contact the bottom lip region of the patient. The outer side has been divided into an upper and a lower portion, wherein the upper portion is at a reduced angle in respect to the lower portion. The apex 950 is adapted to rest or engage the cleft formed between the bottom lip of the patient and lower extremity of the chin. The upper portion is adapted to engage the patient's face at a position lower and extending away from the cleft. Thereby providing an increased sealing surface between: the patient's face at the location between the bottom lip and the lower extremity of the chin; and the outer side of the cushioning component.

As best shown in FIGS. 16g and 25, the patient contacting surface 940 is generally flat or has a larger radius r2 when compared to the nasal bridge region radius r1. This arrangement aids in comfort and increases the length of the sealing surface such that a better seal may be maintained.

In FIG. 25, the radius r2 at the apex of the cushion is preferably about 5 mm.

Alternatively, patient contacting surface 940 may have apex 950 that may first contacts the patients face and anchors the cushion in the dimple of the chin or curvature between the lower lip and chin region. Apex 950 may have a relatively small radius r2 when compared to that radius r2 shown in FIG. 16g. Radius r2 may be about 5 mm. Patient contacting surface 940 may also have a kink or inflexion 960 that may generally match the approximate curvature of the chin so as to rest the cushion on the chin to sealingly engage the cushion with the patient. This kink 960 also allows apex 950 to flex inwards towards the centre of the cushion, and outwards away from the centre of the cushion, so as to accommodate movement of the patient's chin or jaw. For example, it is possible for patients to drop their jaw during sleep, so in order to maintain a seal with the patient, the mask must be able to move with the patient's jaw. This arrangement further enables a greater fit range of patients, i.e. kink 960 may flex either inwards or outwards on a patient's jaw depending on the length and depth of their chin, other facial features etc.

Additionally, as shown in FIGS. 16g and 25, the internal wall 942 of the cushioning component is arranged substantially vertical or normal to the face of the patient in use as demonstrated by angle 2150. This arrangement reduces the likelihood of the foam cushioning component touching the patient's bottom lip when compressed in use, a problem that may occur for larger faces within each size range.

The preferred maximum width of the cushioning component as measured in respect of the base surface is generally about 35 mm in relation to the bottom lip region. The preferred maximum height of the cushioning component is generally about 26 mm in relation to the bottom lip region.

In FIG. 25, the angle formed between the outer side and base surface is approximately between 80-90 degrees; and the angle formed between the inner side and the base surface is approximately between 90 to 100 degrees. Preferably, the angle by which the outer side meets with the base surface is generally less than the angle formed between the inner side and the base surface.

Side of Nose Region

Figure 21:
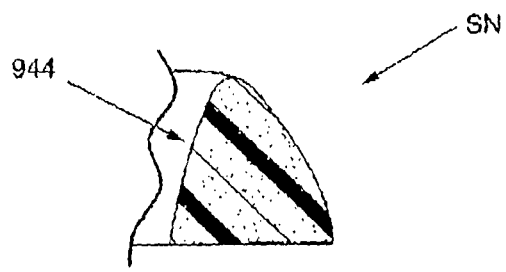
Figure 22:
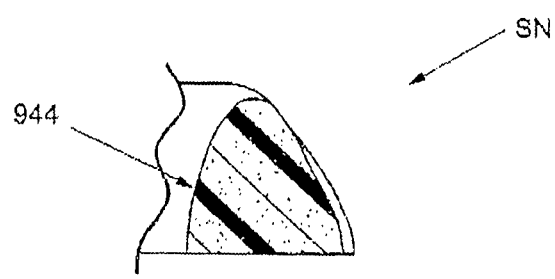

As shown in FIG. 16h, the cross section at the side nose SN is generally triangular. The cross section at the side nose region SN may also be another other reasonable shape, such as generally rectangular, oval, octagonal etc. In addition, it is possible for the cross section at the side nose region to include a shape with generally rounded or curved corners. The cross section at the side nose region may also be an irregular shape. FIGS. 21 and 22 show an alternative cross section for the side of nose region.

FIG. 16h shows a cross-section of the cushioning component in a side of nose region SN. Similar to the nasal bridge region NB as shown in FIG. 16g, the cross section is generally triangular. However the triangular cross section is skewed or biased towards the inner edge of the cushioning component. This arrangement aids with sealing because inner wall 944 abuts the side of the patient's nose in use, thereby increasing the sealing surface. This is similarly demonstrated in FIGS. 21 and 22.

Preferably, the outer side is longer than the inner side. Also preferably, the angle formed between the outer side and the base surface is generally less than the angle formed between the inner side and the base surface.

The most preferred maximum width of the side of nose region (as measured along the base surface) is 22 mm and most preferred maximum height of the cushioning component at the side of nose position is approximately 24 mm.

Cheek Region

Figure 23:
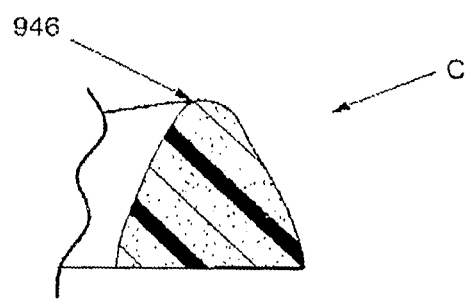
Figure 24:
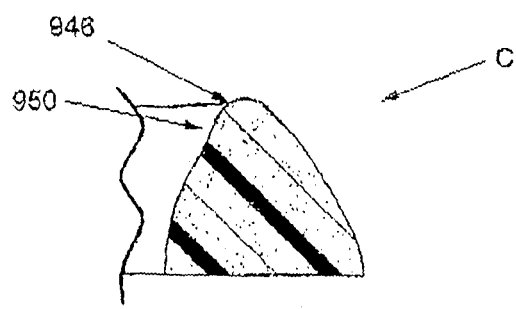

As shown in FIG. 16i, the cross section at the cheeks C is generally trapezoidal or triangular. The cross section at the cheeks region C may also be another other reasonable shape, such as generally rectangular, oval, octagonal etc. In addition, it is possible for the cross section at the cheeks region to include a shape with generally rounded or curved corners. The cross section at the cheeks region may also be an irregular shape. FIGS. 23 and 24 show an alternative cross section for the cheek region.

FIG. 16i shows a cross-section of the cushioning component in a cheek region C. As illustrated, the contacting surface or apex 946 where the cushioning component contacts the patient's cheek is similar to that at the bottom lip region BL as shown in FIG. 16g. The cross section is generally triangular, and may have a smaller top surface 946 when compared to the top surface 940 of the bottom lip region BL. This arrangement aids sealing around the patient's cheeks in use and increases the comfort of the interfacing portion, while reducing the bulk of the interfacing portion at the cheek region C.

A similar arrangement is shown in FIGS. 23 and 24. However, as shown in FIG. 24, inflexion 950 changes the curvature of the side wall of the cushion so that it may hinge or bend inwards. This may increase the ability for the cushion to seal on the patient's face when in use.

Preferably, the outer side of cushioning component is longer than the inner side. Also preferably, the angle formed between the outer side and the base surface is generally less than the angle formed between the inner side and the base surface.

The most preferred maximum width of the cheek region (as measured along the base surface) is 23 mm and most preferred maximum height of the cushioning component at the cheek region is approximately 24 mm.

Additionally, when the clip portion is joined or mounted to the cushioning component, the apex of the cushion is additionally offset towards the centre or middle of the mask. In the described embodiments, the apex may be offset to the extent that it overhangs the point formed between the inner side and the base surface.

2.2.2 Nasal Mask

FIGS. 39 to 47 show an alternative embodiment of the present invention. Cushion component 4000 may be used as a nasal mask that only covers the nose of the patient in use, and is positioned on the nose bridge, side of nose, cheeks and or upper lip region and may not cover the patient's mouth.

Preferably, the cushioning component of the nasal mask shown in respect of these embodiments is preferably: 70-75 mm in length (when measured from the outer most edges of the base surface of the cushioning component); and the width of the cushioning component is approximately 75-80 mm.

Nasal Bridge Region, Side of Nose Region and Cheek Region

The nasal bridge region 4200, side of nose region 4300 and cheek region 4400 may be generally similar to that described above for a full face cushion.

The preferred height of the cushioning component at the region designated to correspond to the nasal bridge of the patient is approximately 22 mm. The height of the cushioning component at the position designated to meet the side of the nose is approximately 25-27 mm. The height of the cushioning component at the position designated to meet the patient's cheek regions is approximately 27 mm.

The preferred width of the cushioning component in the side of nose regions is typically about 20 mm. Whereas the preferred width of the cushioning component in the cheek regions is typically about 18 mm.

Upper Lip Region

Figure 39:
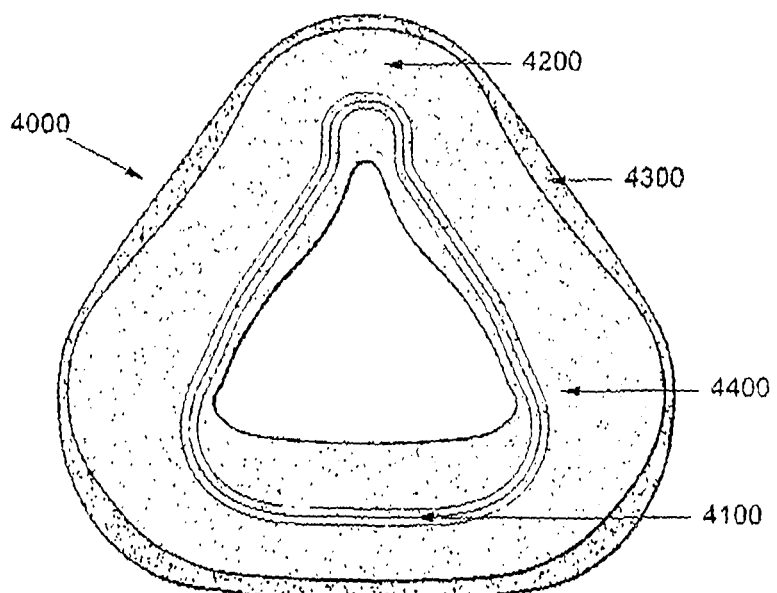
FIG. 39 is a front view of a further embodiment of a interfacing structure for use with a nasal mask.
Figure 40:
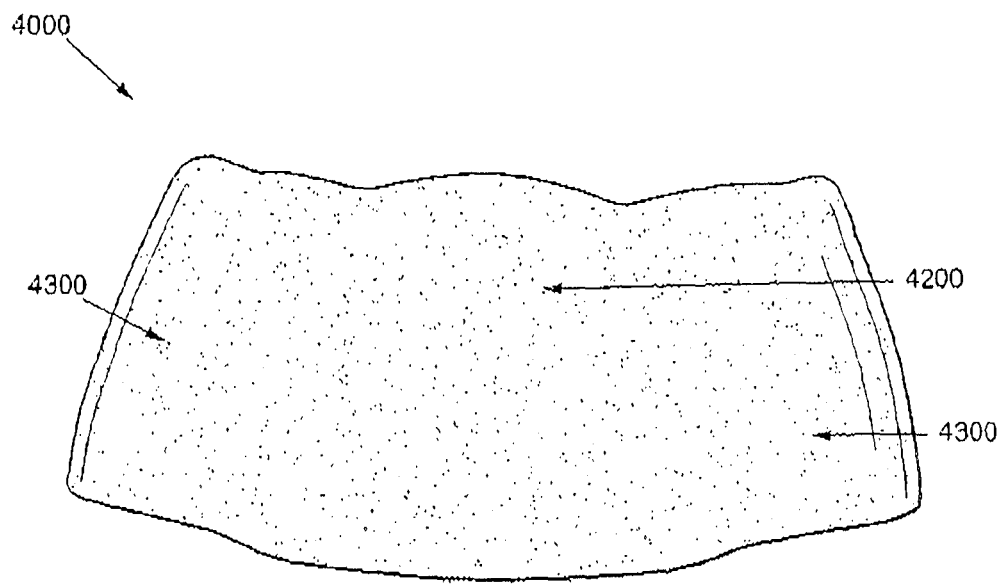
FIG. 40 is a top view of the embodiment shown in FIG. 39.
Figure 41:
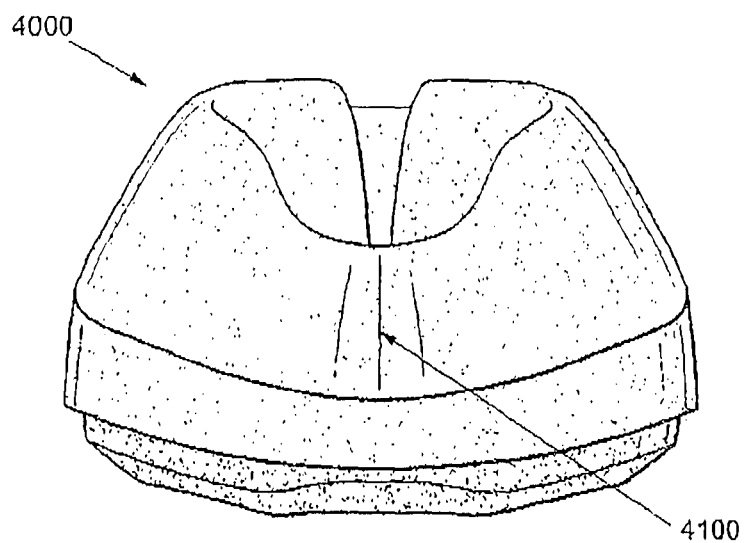
FIG. 41 is a bottom view of the embodiment shown in FIG. 39.
Figure 42:
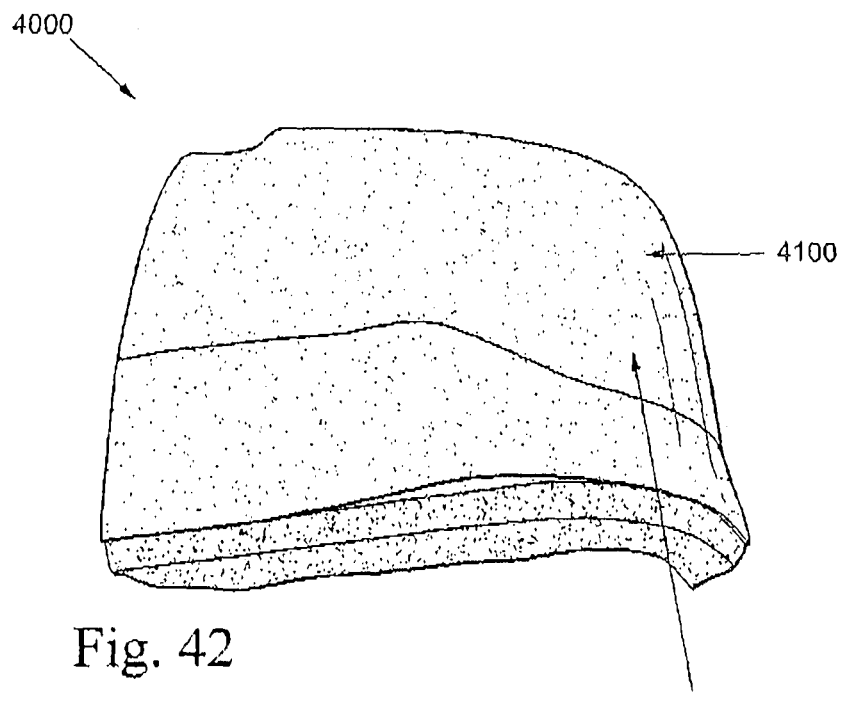
FIG. 42 is a side view of the embodiment shown in FIG. 39.
Figure 43:
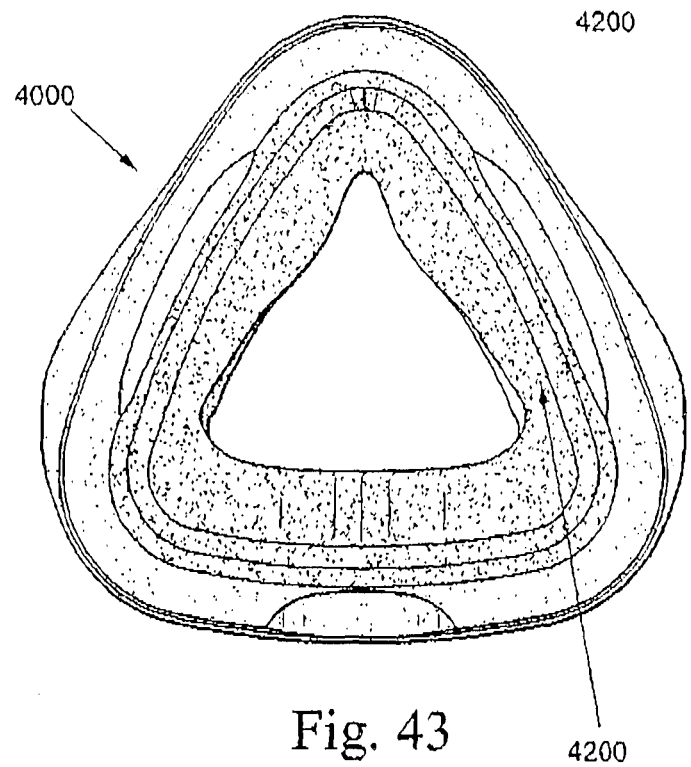
FIG. 43 is a back view of the embodiment shown in FIG. 39.
Figure 44:
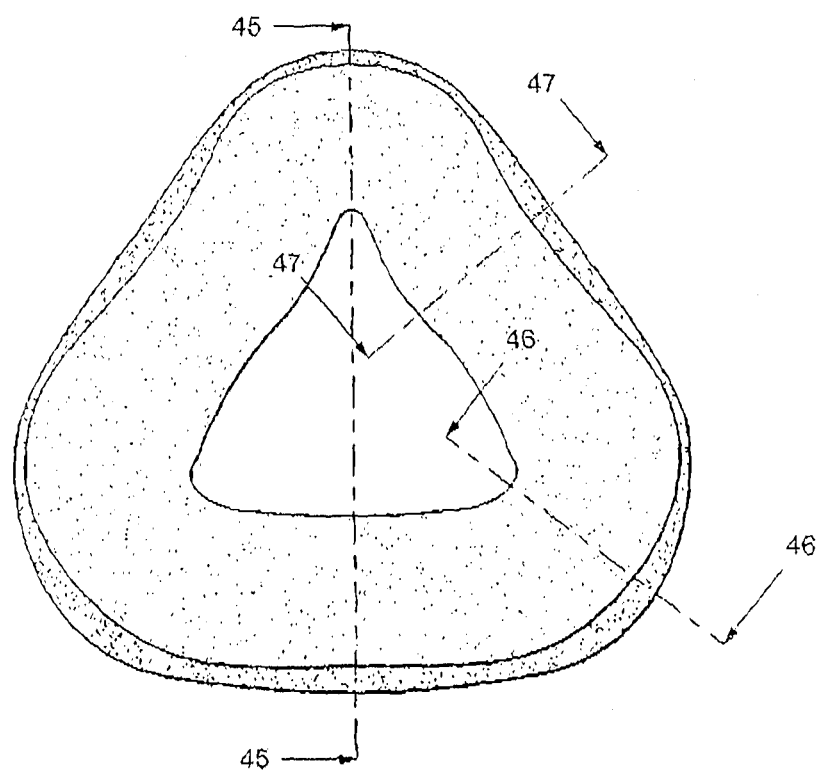
FIG. 44 is a front view of a further embodiment of an interfacing structure for use with a nasal mask.
Figure 45:
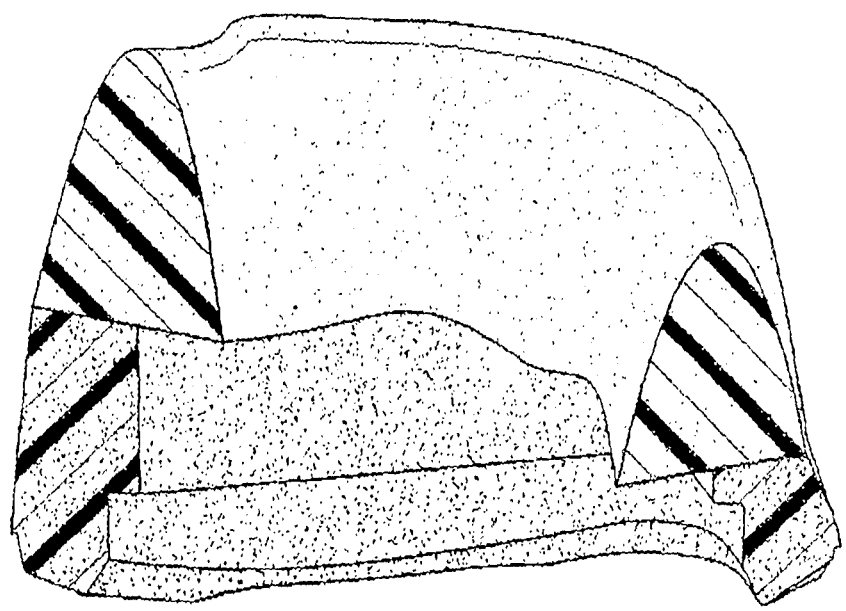
FIGS. 45-47 depict various cross-sectional views of the embodiment shown in FIG. 44.
Figure 46:
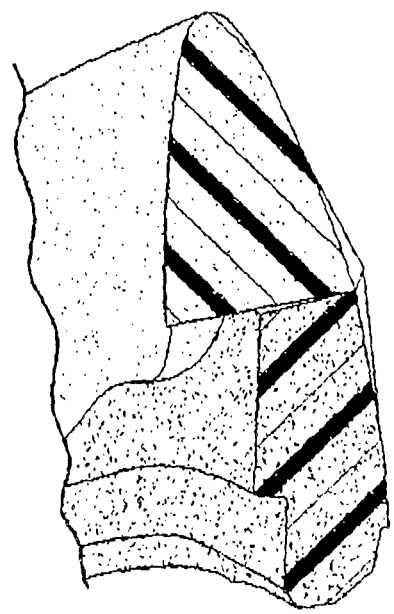
Figure 47:
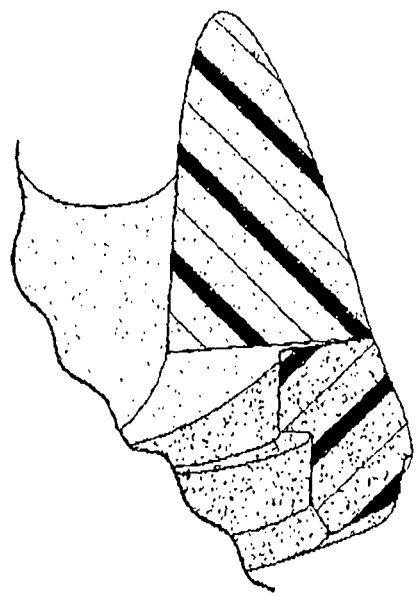

As shown in FIGS. 39 and 41, cushion component 4000 may have an upper lip region 4100 that has a dip or region of reduced height (when viewed from a side view as shown in FIG. 41) relative to the height of other regions 4200. This feature may accommodate various upper lip regions of patients whilst avoiding accidental occlusion of the nares. The overall reduction in the amount of foam material may reduce the risks for patients.

The preferred width of the cushioning component in the upper lip region is typically about 16 mm. The width of the cushioning component in the upper lip region may be 10-20 mm. The width of the cushioning component in the upper lip region may be 15-20 mm. The width of the cushioning component in the upper lip region may be 12-20 mm. The width of the cushioning component in the upper lip region may be 10-15 mm. The width of the cushioning component in the upper lip region may be 10-18 mm. The width of the cushioning component in the upper lip region may be 10-14 mm.

The preferred height of the cushioning component at the region designated to correspond to the upper lip of the patient is approximately 18 mm. The height of the cushioning component in the upper lip region may be 10-20 mm. The height of the cushioning component in the upper lip region may be 10-25 mm. The height of the cushioning component in the upper lip region may be 15-20 mm. The height of the cushioning component in the upper lip region may be 16-23 mm.

Fit Range

Because of the wide range of sizes and shapes of different people's faces, it is a continual challenge for mask designers to determine the least number of mask shapes required to fit the broadest range of patients. In one ideal form, a single mask shape would fit all patients.

A mask assembly in accordance with the invention provides an improved fit range. This maybe preferably achieved by combining a more comfortable and compliant material with a more anatomically neutral geometry that seals against a wider range of facial anatomy for a given shape.

The versatility of a chosen cushion shape, and hence its fit range performance, is also enhanced by the 'hovercraft' behavior exhibited by the cushion. In this context the "hovercraft' behavior is generally defined by the air pressure in the cavity of the mask when the air pressure in cavity of the mask is greater than the outside environmental air pressure and thereby allows the mask to float on the face of the wearer. The pressure seal is preferably formed by the cushioning component. This feature may enhance the ease and speed of fitting the mask.

When pressurized with air the cushion material has extra extensibility compared to other known cushion materials. The soft flexible cells in the foam material effectively stretch when inflated allowing the material the freedom to enlarge. This allows the cushion material to have an extra dimension of conformability over other cushion materials known in the art e.g. silicone, by being able to expand and morph to facial anatomy when inflated with air pressure. This is, in part, also achieved by combining an expandable open-cellular structure in direct communication with the air that is providing the positive airway pressurization. It is the flow of air through the sealing material that forms a fine layer of pressurized air between the facial skin, and the flexible nature of the cushion material that enables this hovercraft effect, hence making it easier to fit to the face. The foam being less sticky than silicone also has a significant advantage in achieving an easy, fast and comfortable fit.

2.3 Method of Manufacturing

The following manufacturing techniques may be used to create a range of shapes and cross-sections as may be required for different facial shapes. Since the cushioning component is preferably made from unskinned foam, one or more cutting processes may be used to create the part, such cutting processes including die cutting, and/or machining, etc. Alternatively the cushioning component may be molded with measures taken in the process to minimize the skin on the foam component, or the skin being subsequently removed from the molded component in a post process e.g. machined. Preferably, the foam material used in the herein described embodiments may be an open and closed cell foam. The foam material used may be an open cell foam. The foam material used may be a closed cell foam.

2.3.1 Die Cutting

In the illustrated embodiment shown in FIGS. 4a-4g, both an inside surface and an outside surface of the foam cushion component 232 are die cut. This typically results in generally straight cut edges. The cushion in these embodiments may have a generally rectangular cross section, where the top surface is generally substantially parallel to the patient's face in use, and the inner and outer side surfaces are generally perpendicular to the patient's face in use. It may be possible to die cut the foam using additional processing steps to create a non-rectangular cross section, e.g. the use of shims. The die cutting of a cushion component then from a flat sheet of foam results in a flat backed cushion component which may subsequently take the shape of a clip that it is assembled to e.g. glued. The foam cushion is therefore deformed into its final intended shape.

To create a curved backed cushion, that for example matches the shape of a curved clip without stretching or deformation, the cushion component may be die cut from a foam sheet that is cut into a curved shape rather than a flat sheet. The curved sheets may be formed from a known process referred to as contour cutting, where a foam block is cut into curved sheets by being fed into an oscillating blade that changes position and orientation during the cutting process.

In addition to die cutting or in the alternative, the cushioning component, e.g., as shown in FIGS. 9a to 12f, may be cut into a three-dimensional shape or geometry using the techniques described in AU 2008904769 and AU 2008904778.

FIGS. 9a to 9d illustrate a foam-based interfacing structure 430 including a foam cushion component 432 and a clip portion 434. Outer wall 400 may include contours and curvature incorporated into the design. The inner, patient contacting wall (or orifice) 402 may be die cut as known in the art. Again, this typically results in straight cut edges (e.g., see FIGS. 9b and 9d).

Figure 10A:
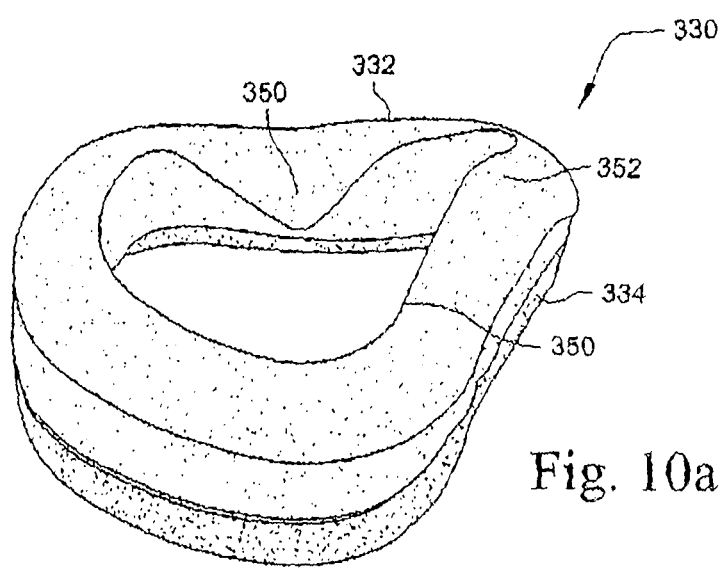
Figure 10B:
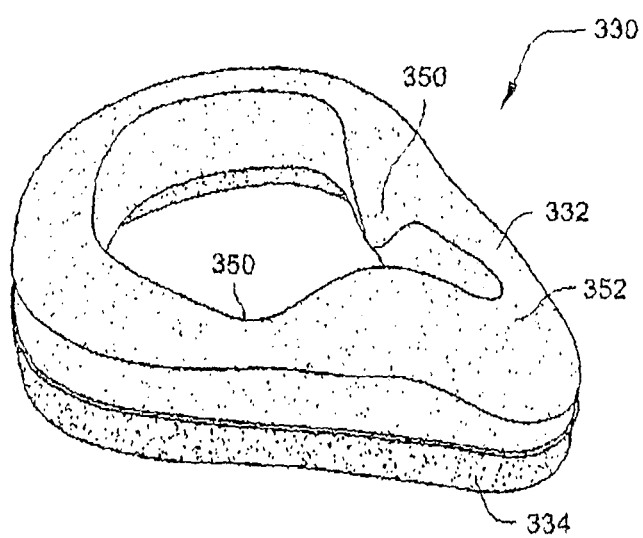
Figure 10C:
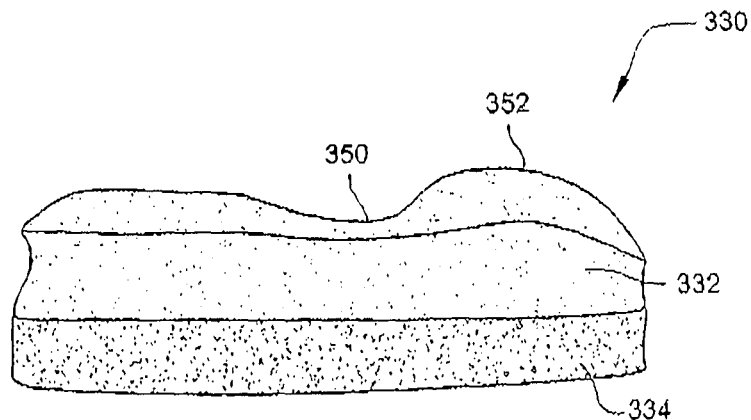

FIGS. 10a to 10c illustrate a foam-based interfacing structure 330 including a foam cushion component 332 and a clip portion 334, wherein the cushion component 332 includes localized regions with curvature or ridges, e.g., ridges 350 along cheek regions of the cushion component, a curvature 352 along the nasal bridge region of the cushion component, etc. In addition, the cushion component 332 is contoured along the chin region of the cushion component. The straight die cut inner and outer edges remain perpendicular to the patient's face in use similar to the previous embodiment.

Figure 11A:
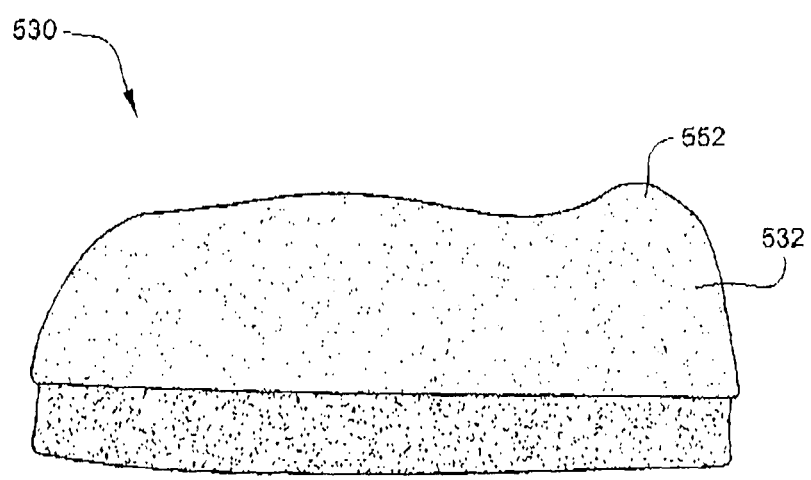
FIGS. 11a to 11c show various views of a foam-based interfacing structure according to another embodiment of the present invention.
Figure 11B:
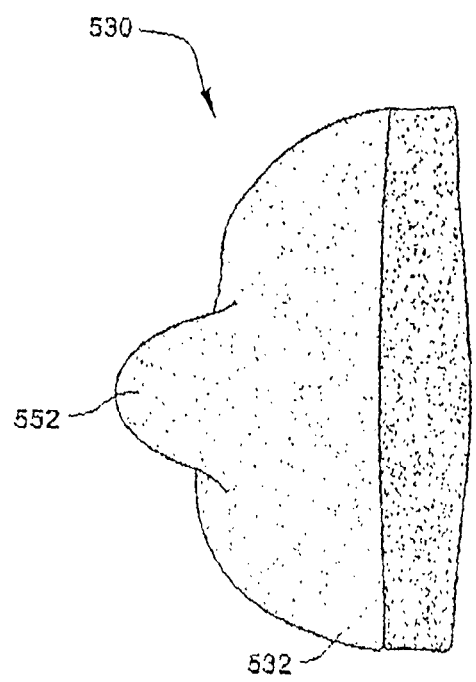
Figure 11C:
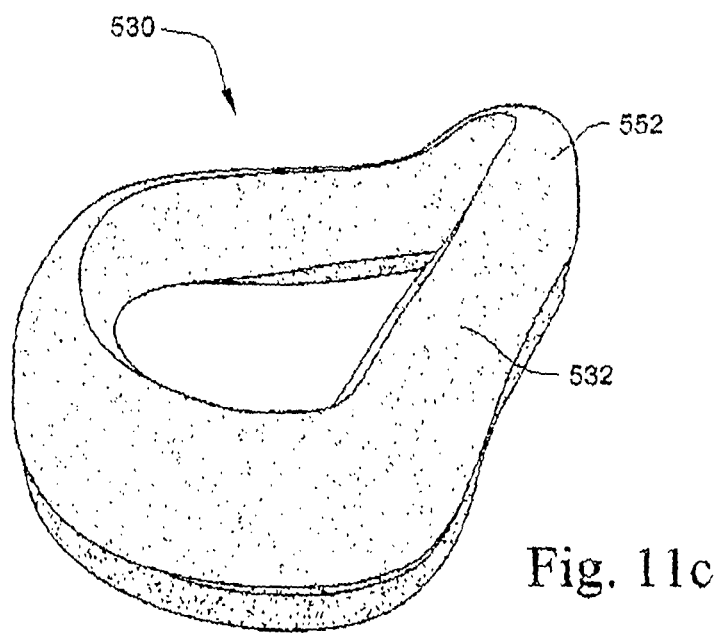
Figure 12A:
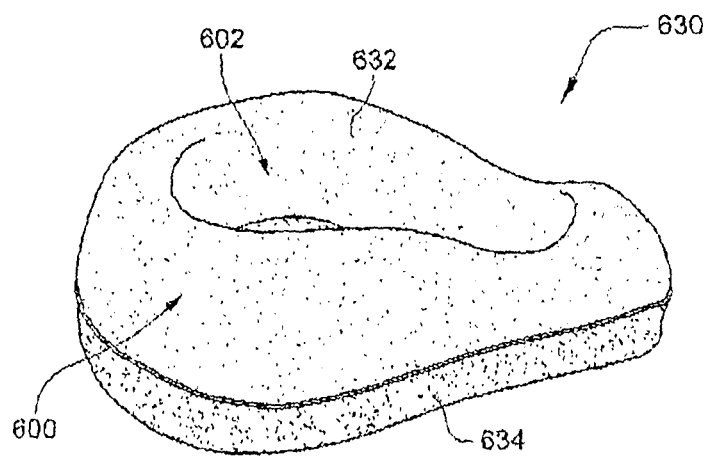
FIGS. 12a to 12f show various views of a foam-based interfacing structure according to another embodiment of the present invention.
Figure 12B:
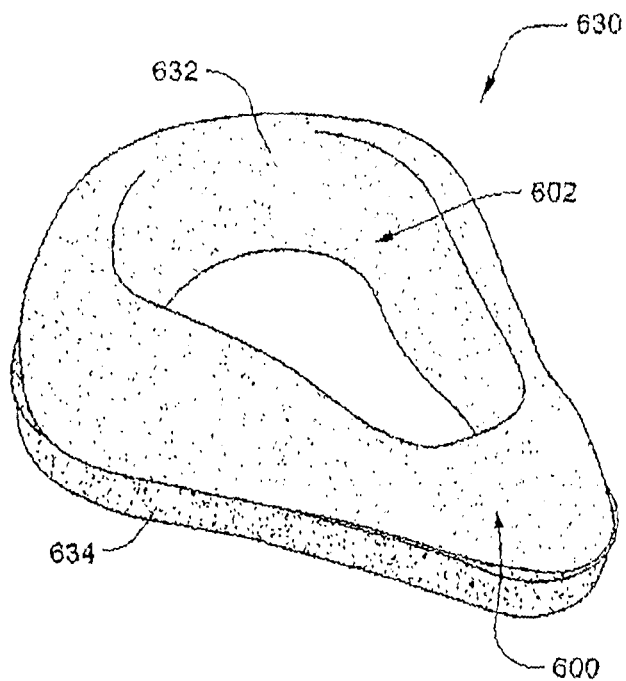
Figure 12C:
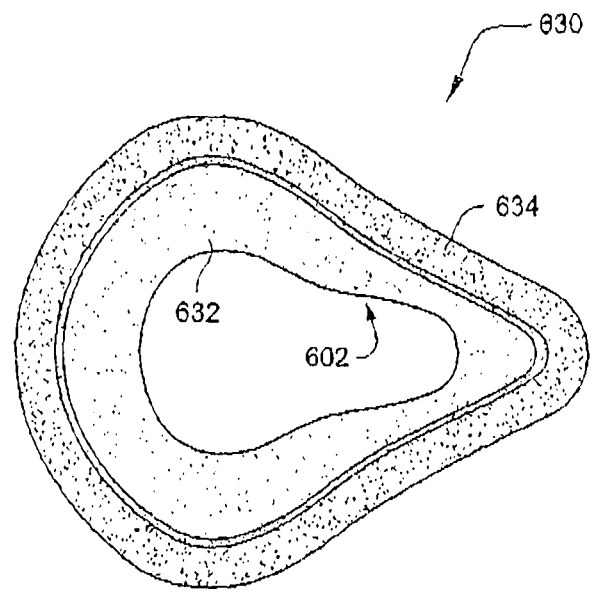
Figure 12D:
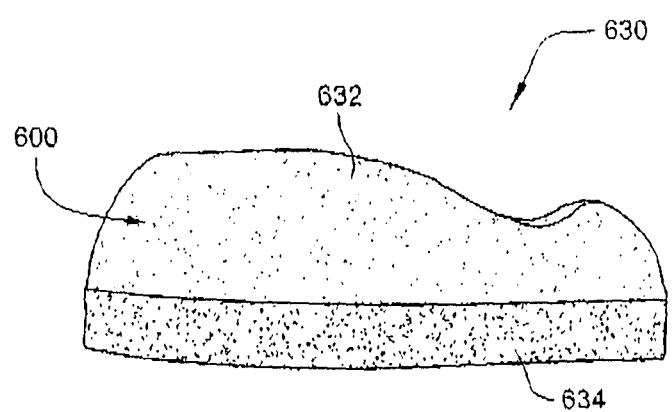
Figure 12E:
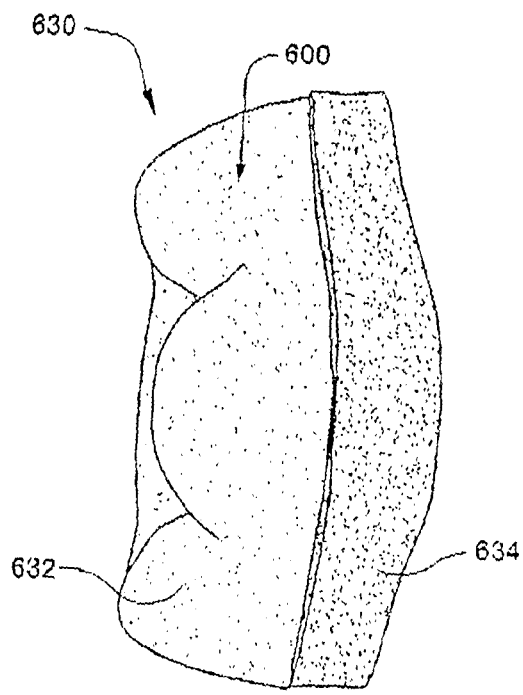
Figure 12F:
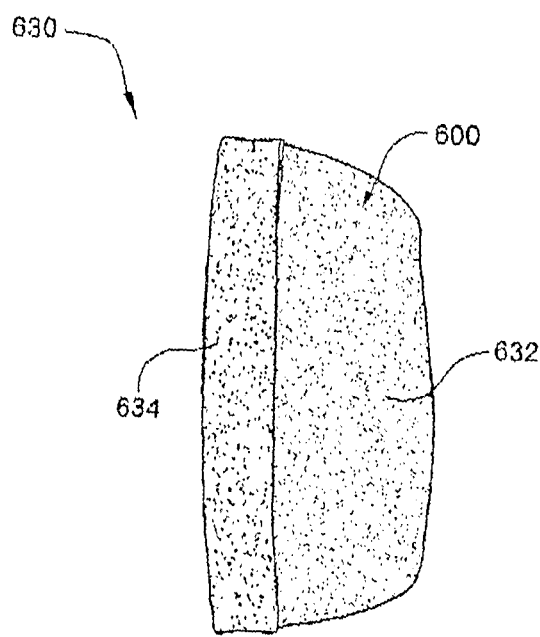

FIGS. 11a to 11c illustrate a foam-based interfacing structure 530 where a localized region 552 in the cushion component 532 at the nasal bridge has been raised, e.g., formed with a curved surface.

FIGS. 12a to 12f illustrate another embodiment in which a foam-based interfacing structure 630 including a foam cushion component 632 and a clip portion 634, wherein the foam cushion component 632 includes a slab of foam that is cut using methods known in the art. This process may be repeated in order to cut the outer wall 600 of the cushion component and then the inner, patient contacting wall (or orifice) 602 of the cushion component.

3. Clip Component

3.1 Material

The cushion-to-frame component may be made from a material that has greater structural integrity than the cushioning component. In a preferred embodiment the clip is made from polyurethane foam that has higher hardness, higher density, and lower permeability than the foam used for the cushioning component. The clip/cushion-to-frame component may be formed in a mould giving rise to a harder, denser, lower permeability foam having a skin. In an alternatively preferred embodiment, the clip may be constructed of a non-foamed polymer, for example (but not limited to), nylon, polycarbonate, polypropylene.

Preferably, the clip portion or clip component may be of reduced hardness or increased flexibility in comparison to the frame portion of the mask to which it is to connected or secured with.

3.2 Shape

Figure 13:
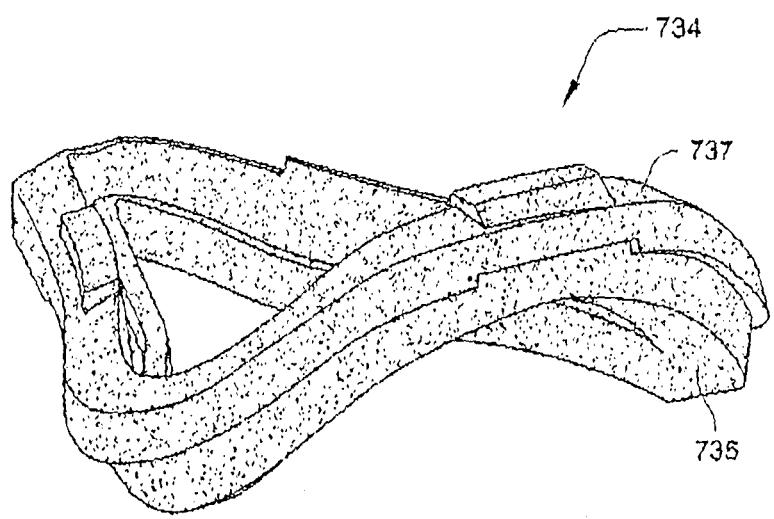
FIG. 13 is a perspective view of a clip portion according to an embodiment of the present invention.
Figure 14A:
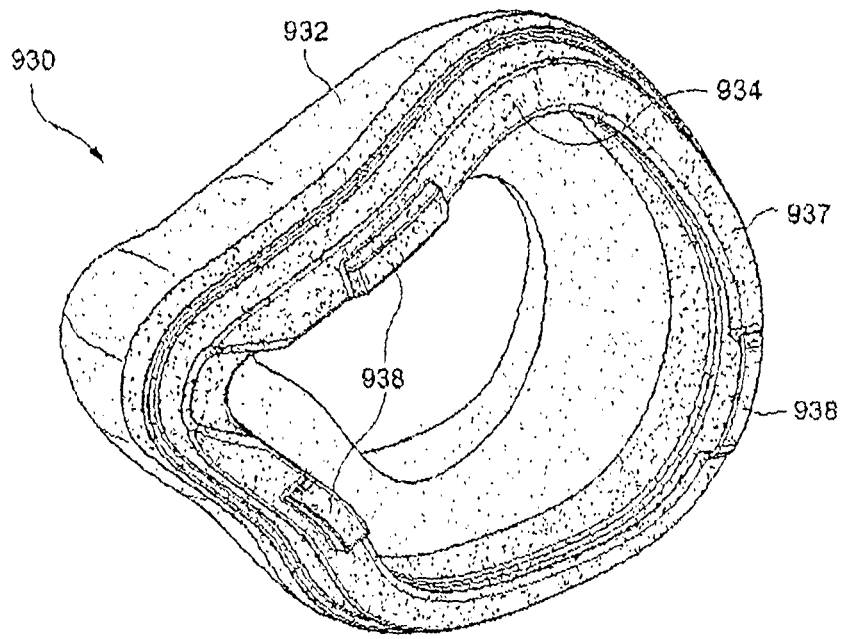
FIGS. 14a to 14f show various views of a foam-based interfacing structure according to an embodiment of the present invention.
Figure 14B:
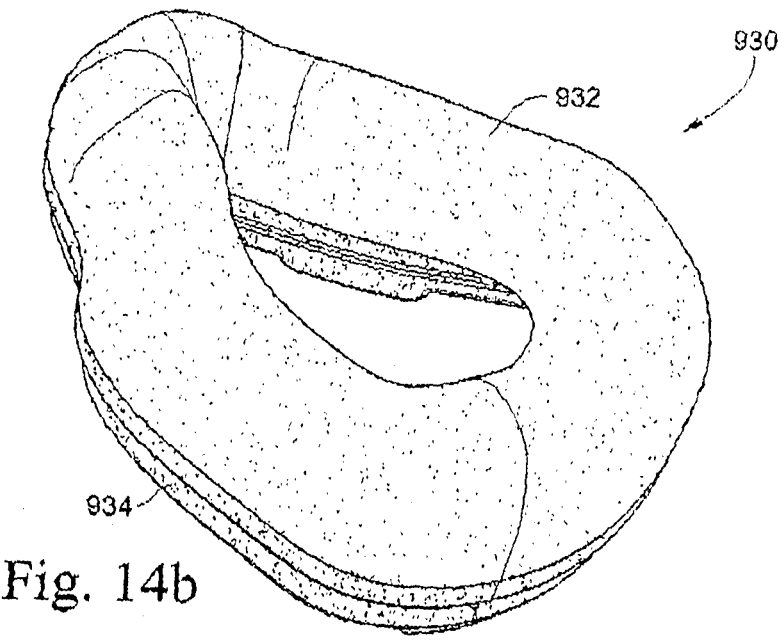
Figure 14C:
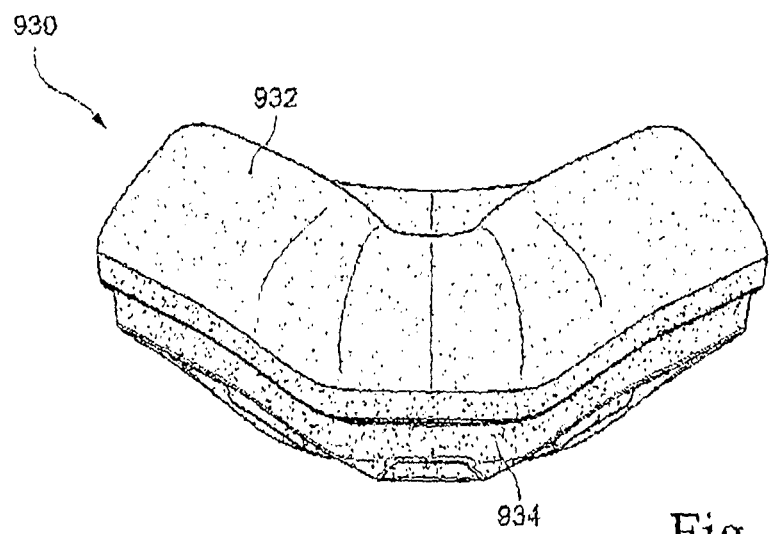
Figure 14D:
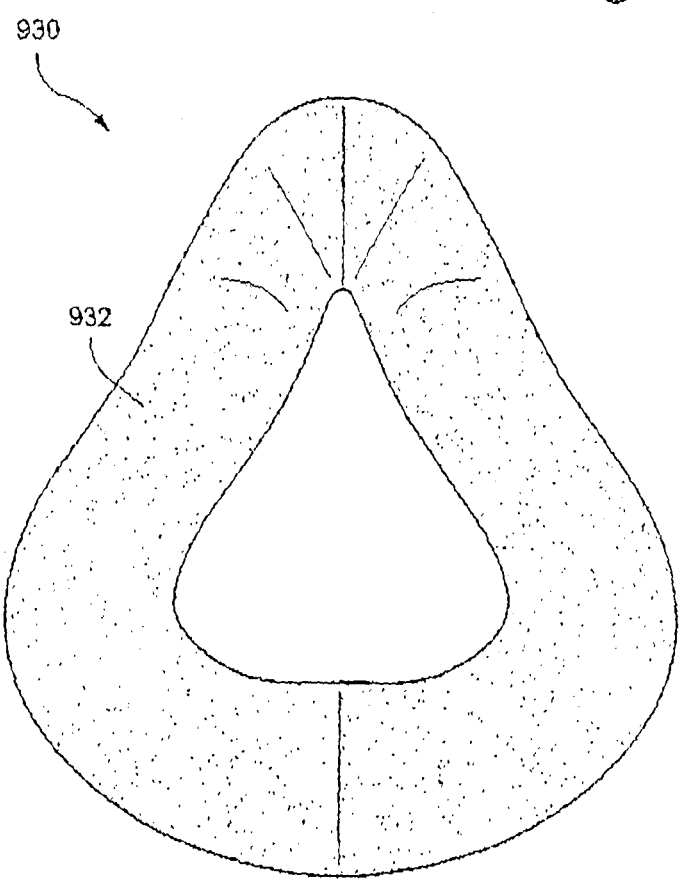
Figure 14E:
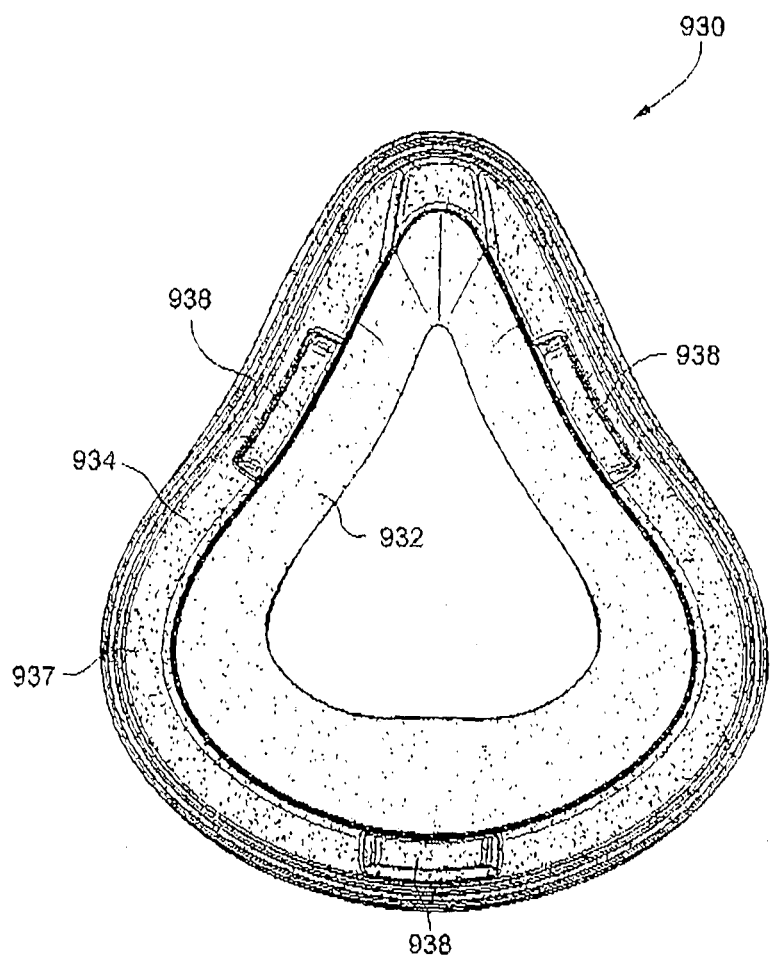
Figure 14F:
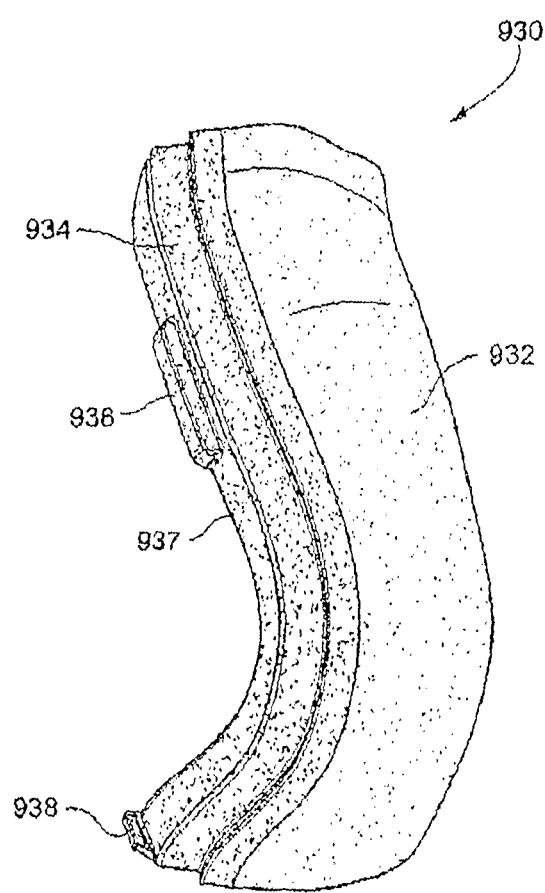
Figure 15A:
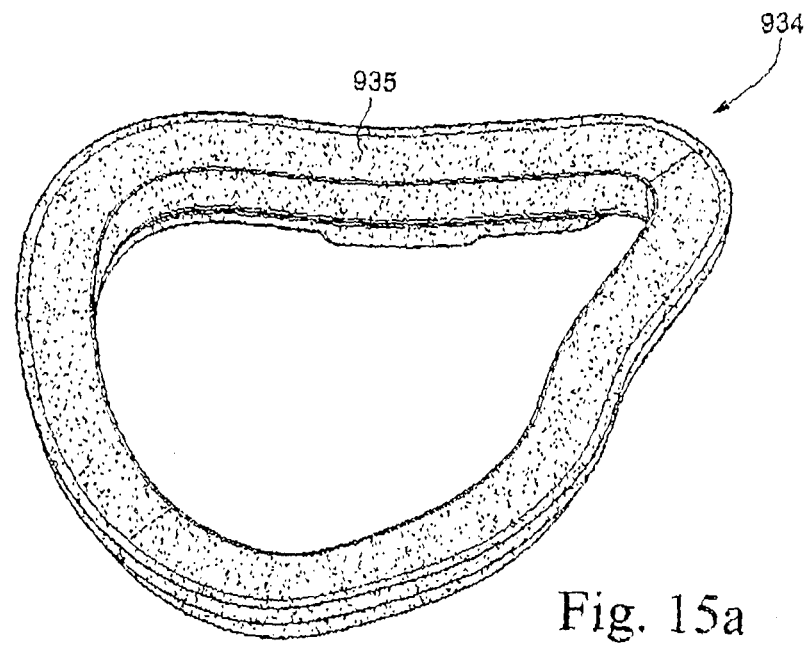
FIGS. 15a to 15e show various views of a cushion-to-frame component of the interfacing structure shown in FIGS. 14a to 14f.
Figure 15B:
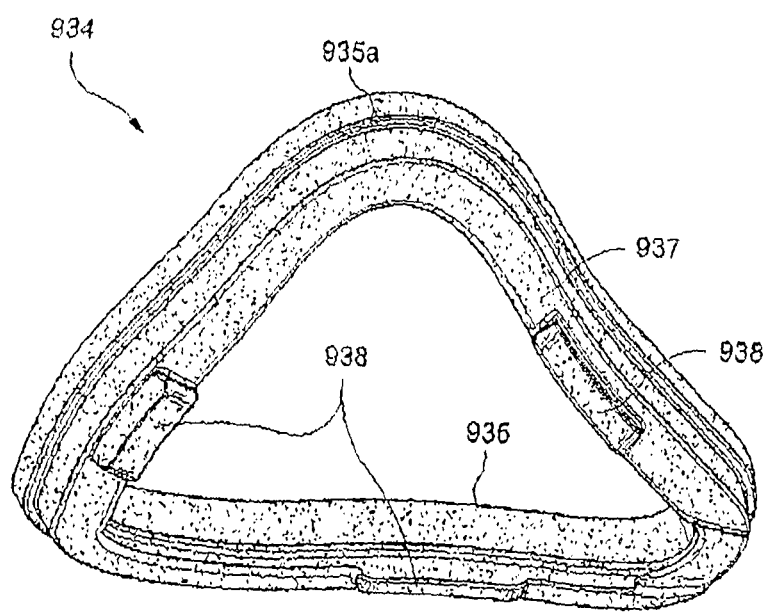
Figure 15C:
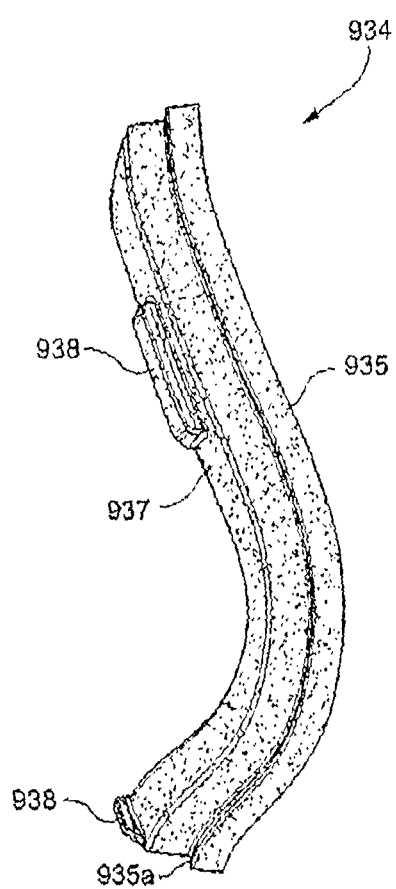
Figure 15D:
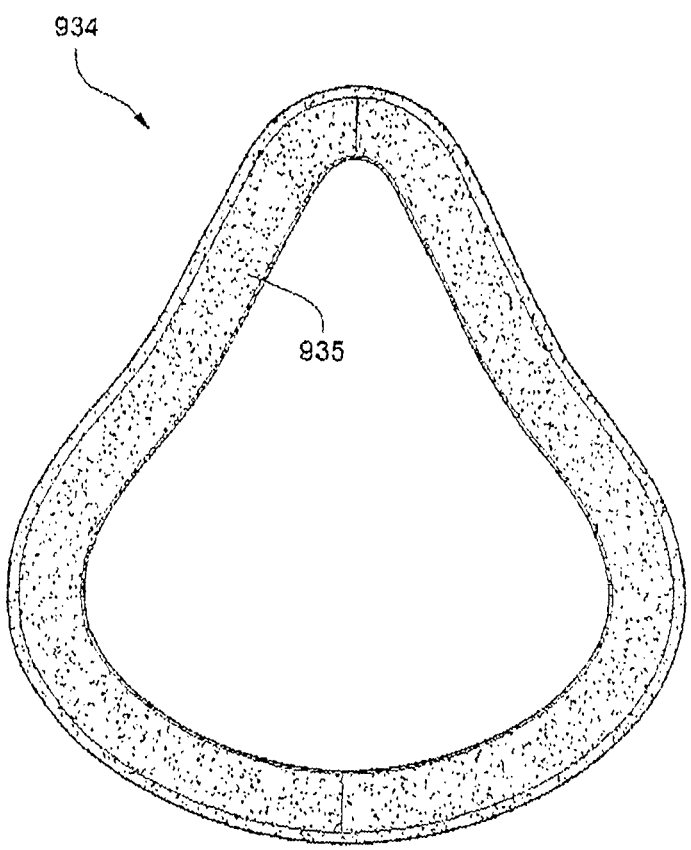
Figure 15E:
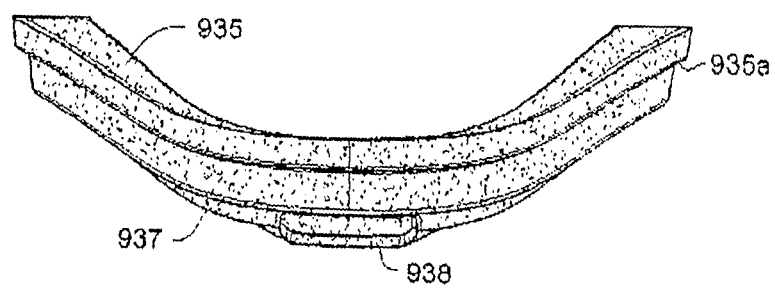

The clip 934 is shown generally in FIG. 13, and in more detail in FIGS. 15a-15e. The clip 934 is generally shaped in order to align with the frame. However, the general curvature of the clip 934 can be altered to suit the frame to which it is to be fitted. The general curvature of the clip may also be used to shape the cushion component. Since the cushion component is made from compliant foam, it will readily adapt to the shape of the clip when joined together. An example of where this may be an advantage is when the cushion component is made to have a flat back (from a flat foam sheet as described previously) and is given its final shape by assembly (e.g. glued) to a clip that gives the cushion its intended shape (e.g. curved).

The clip may also be made flat. The cushion can therefore also be made with a flat back to match the clip. The overall intended shape of the interfacing structure (combination of clip and cushion) can therefore be alternatively achieved by the flat clip and cushion being deformed and retained into a curved frame. This embodiment allows clip to be manufactured flat which can have several advantages including ease of handling and alignment during manufacture, packaging and transportation. The clip can therefore be formed by alternative methods e.g. die cutting from flat sheet material.

The clip may also be made curved. This may be achieved by several means including molding directly into a curved shape, die cutting from curved (contour cut) sheet, or heat forming a flat clip die cut from a thermoformable material. Having the clip curved allows ease of alignment and assembly to a curved frame, as well as giving the cushion a curved shape if the cushion is made from a process that results in it having a flat back.

In a preferred embodiment the clip is made from molded polyurethane. The cushion contacting surface 935 is generally smooth so that it can continuously join and seal to the underside of the cushion. Cushion contacting surface 935 has a lip 935a to enable alignment of the clip to the frame.

Frame contacting surface 937 has three alignment tabs 938 protruding from its surface that engage with the frame. There may be any number of alignment tabs 938 to aid the patient in aligning the interface structure with the anchoring structure. It should also be appreciated that the clip need not have alignment tabs 938 to engage the clip with the frame.

The clip may also be made to incorporate features that engage the frame to aid retention of the interfacing structure to the frame. Examples include, but are not limited to, surface roughening, ribs, notches, snaps etc.

3.3 Method of Manufacturing

The clip component may be separately formed as will be now described, or insert molded as will be described later in this specification.

Figure 18B:
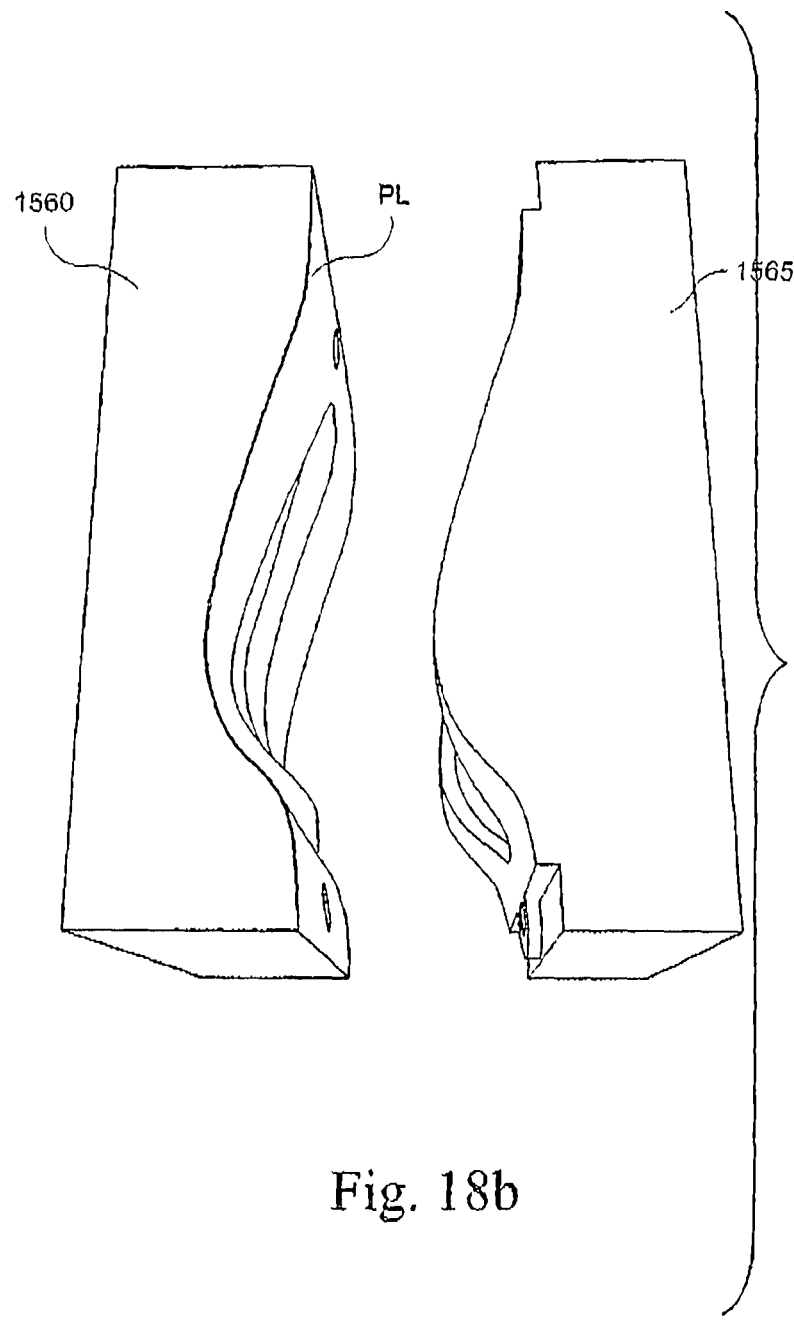
Figure 18C:
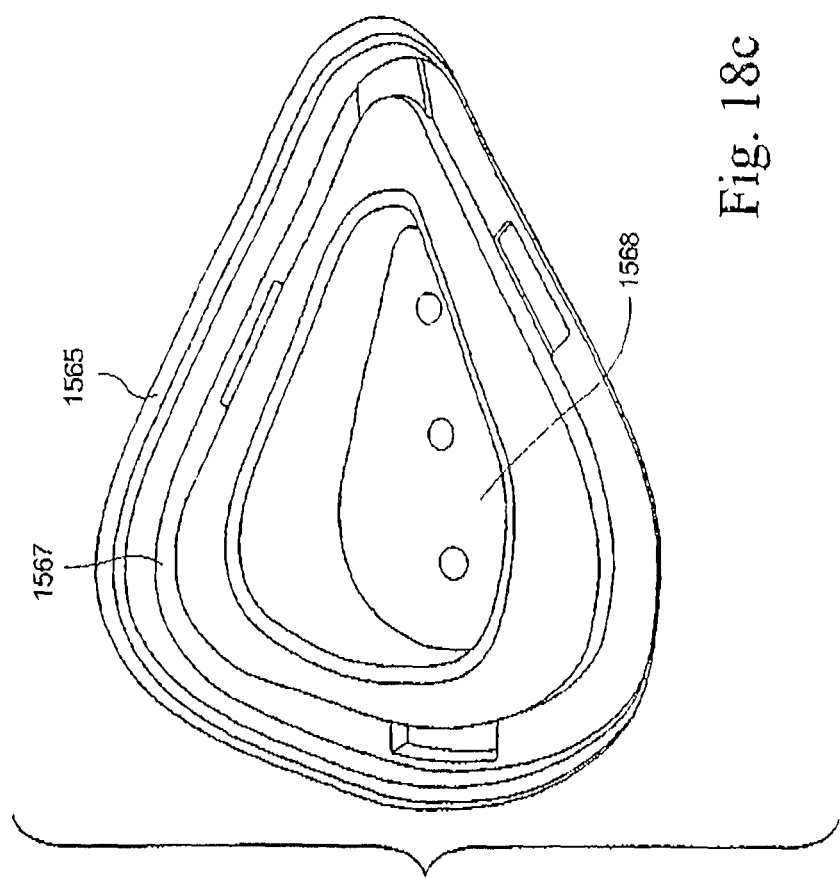

By way of example, FIGS. 18a to 18c illustrate a tool to mold a clip portion by itself, where the clip portion may subsequently be attached to the cushion component, e.g., by an adhesive or simply adhesion between the clip and cushion component. As illustrated, the tool includes a top half 1560 and a bottom half 1565 which are adapted to be joined together to form the clip portion. As shown in FIG. 18b, the tool provides a curved parting line PL between the top and bottom halves 1560, 1565.

The bottom half 1565 includes a cavity 1567 adapted to receive the material (e.g., foaming mixture) that will form the clip portion. Also, the center section 1568 of the bottom half 1565 accommodates a separate insert that acts as a manual ejection feature after molding. The top half 1560 provides a surface 1562 that will form the side of the clip portion for interfacing or joining with the cushion component.

The top and bottom halves 1560, 1565 of the tool are constructed and/or arranged to facilitate demolding of the clip portion from the tool so that the clip portion will not adhere to the tool. For example, the top and bottom halves 1560, 1565 may be constructed of a material from which the mold material (e.g., foaming mixture) may be removed (e.g., high density polypropylene, silicone). Alternatively, a demolding agent (e.g., wax) may be provided to the top and bottom halves to facilitate demolding.

An alternative demolding aid may be a release film that lines the tool and releases from the clip material easily after molding. In a preferred embodiment the release film may double, in whole or in part, as the packaging for the interfacing structure such that the product leaves the molding process already packaged. In another embodiment the clip includes a tab at one or a number of locations that facilitates gripping of the part for demolding during the manufacturing process. This tab feature may also double as an alignment feature for assembly and a gripping feature for disassembly for the user of the mask assembly.

In another embodiment the clip may include a tab feature that includes an end of life indicator for the interfacing structure.

4. Sub-Assembly 4.1 Relative Position

In accordance with an embodiment of the invention, a range of different arrangements of clip portions and cushion components may be provided. For example, the width of the clip portion may preferably match or be less than the maximum width of the cushion component, the width of the cross section of clip portion may be less than the width of the cross section of the cushion component. In these different configurations with different relative widths, the clip portion provides different forms of support to the cushion component.

Wherein the width of the cross section of the clip portion is less than the width of the cross section of cushion component, the clip portion and cushion component may be arranged such that (i) the outer perimeter of the clip portion and cushion component align (hides hardness of clip portion and provides desired freedom of movement in the cushion component), (ii) the inner perimeter of the clip portion and the cushion component align, or (iii) neither the inner or outer perimeter of the clip portion and the cushion component align.

Similarly, wherein the width of the clip portion is greater than the width of the cushion component, the clip portion and cushion component may be arranged such that (i) the outer perimeter of the clip portion and cushion component align, (ii) the inner perimeter of the clip portion and cushion component align, or (iii) neither the inner or outer perimeter of the clip portion and the cushion component align.

When the width of the clip portion is less than the width of the cushion component and the outer perimeter of the clip portion aligns with the cushion component, the cushion component may preferably be more able to flex in regions or directions not having a clip portion next to it than in regions having a clip portion adjacent to it or supporting it. For example, where the cushion component overhangs the clip portion, that overhanging region of the cushion component has more freedom to move. This arrangement can be more comfortable and more able to adapt to different geometries of a person, and provide the correct vectors to seal the cushion component against the face.

Preferably, the clip portion is to be joined to a cushioning component by a base surface of the cushioning component. It may also be preferably to arrange the clip portion to support the external extremity (relative to the circumference of the mask) of the base surface and to have no or little support inner extremity of the base surface.

When used as part of a respiratory mask, it may be preferable that the inner portion of the cushion component overhang the clip portion. In this arrangement in use, the face of the patient may engage with an unsupported inner edge of the softer cushion component causing it to bend and conform to the individual patient's shape. When the mask engages a patient's face, the cushioning component may roll inwards towards the centre of the mask when pressure is applied on the mask towards the patient's face.

Figure 4A:
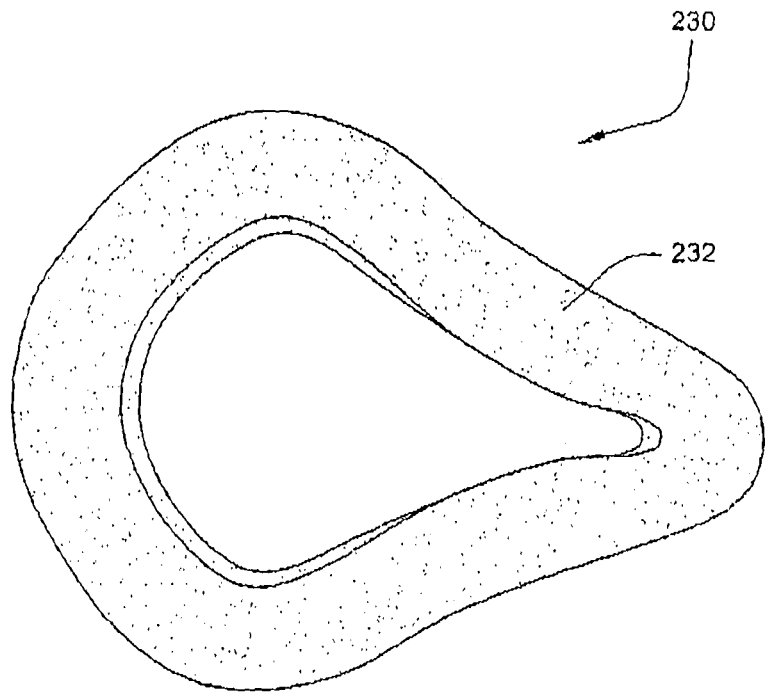
FIG. 4a shows a patient contacting side of an interfacing structure according to an embodiment of the invention.
Figure 4B:
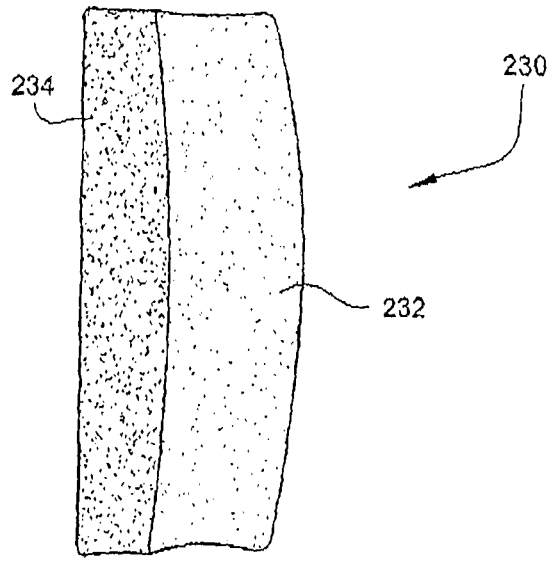
Figure 4C:
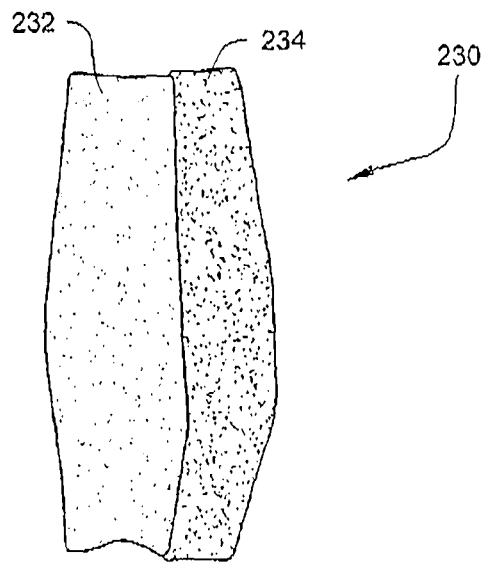
Figure 4D:
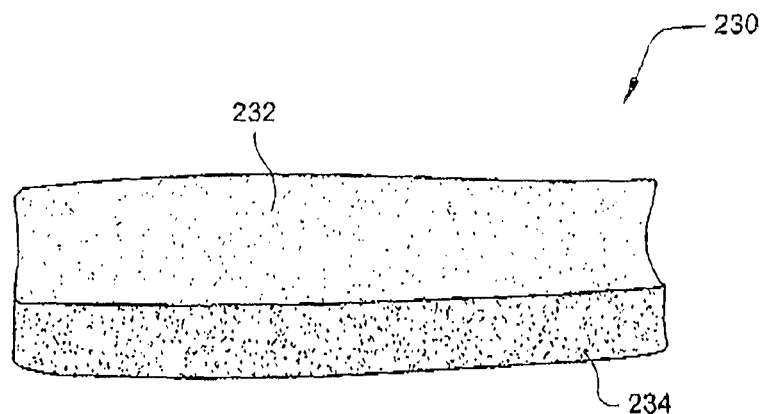
Figure 4E:
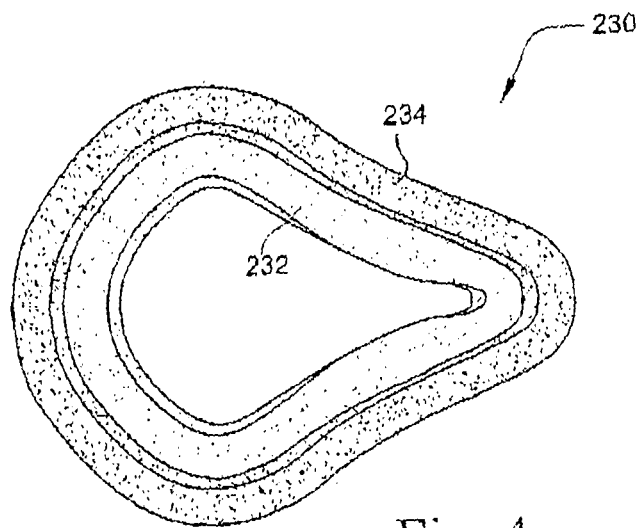
Figure 4F:
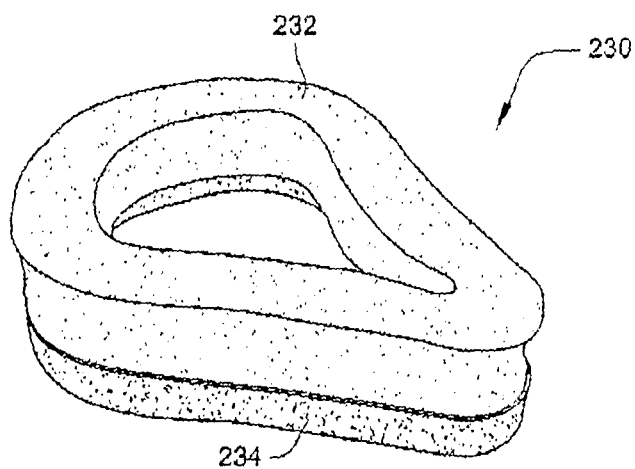
Figure 4G:
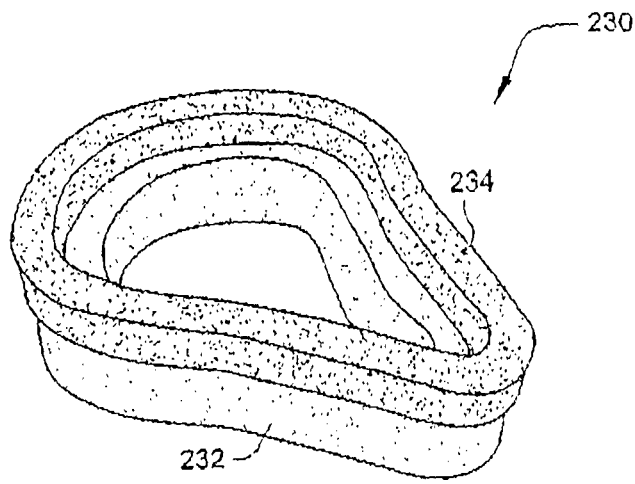
Figures 4, 60:
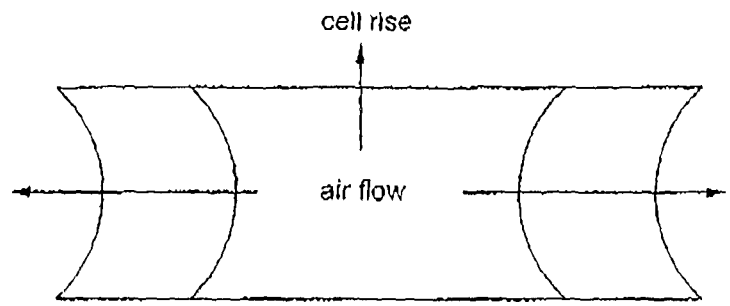
Figures 5, 60:
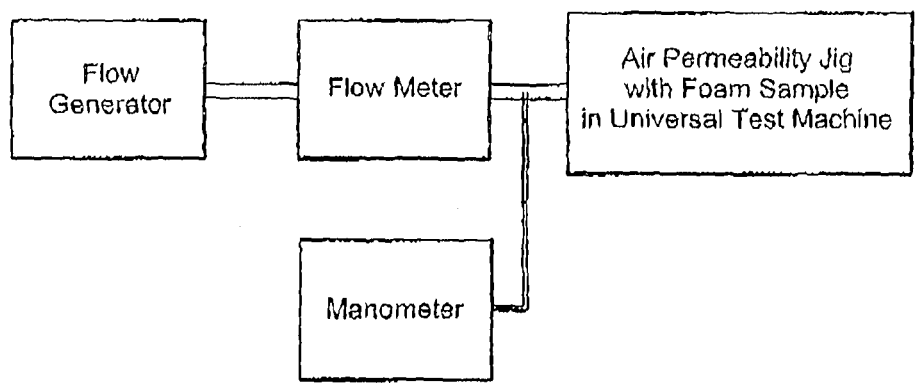
Figures 6, 60:
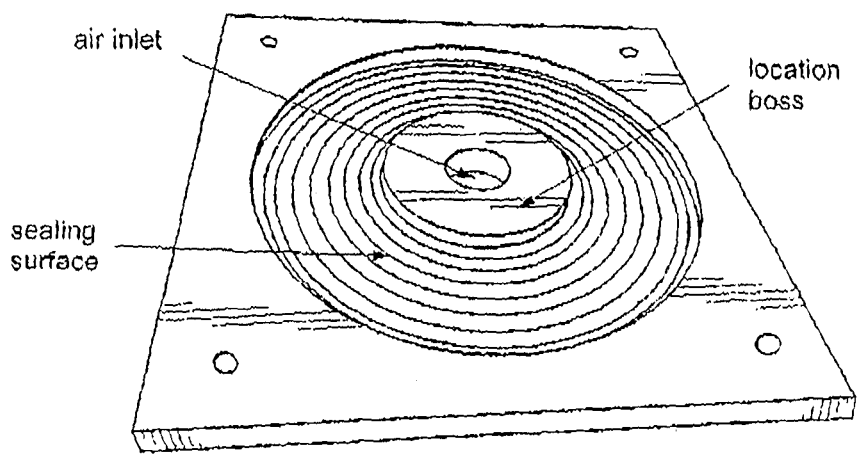
Figures 7, 60:
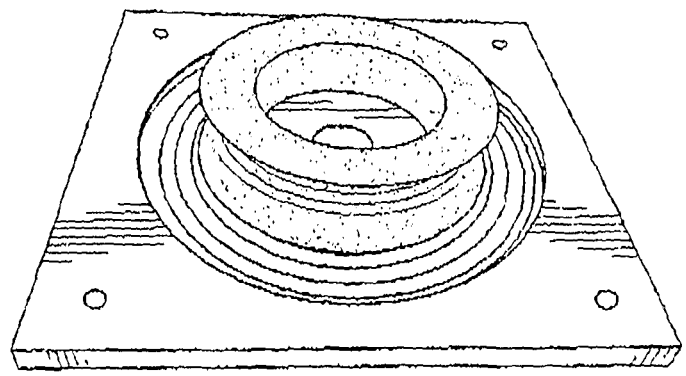
Figures 8, 60:
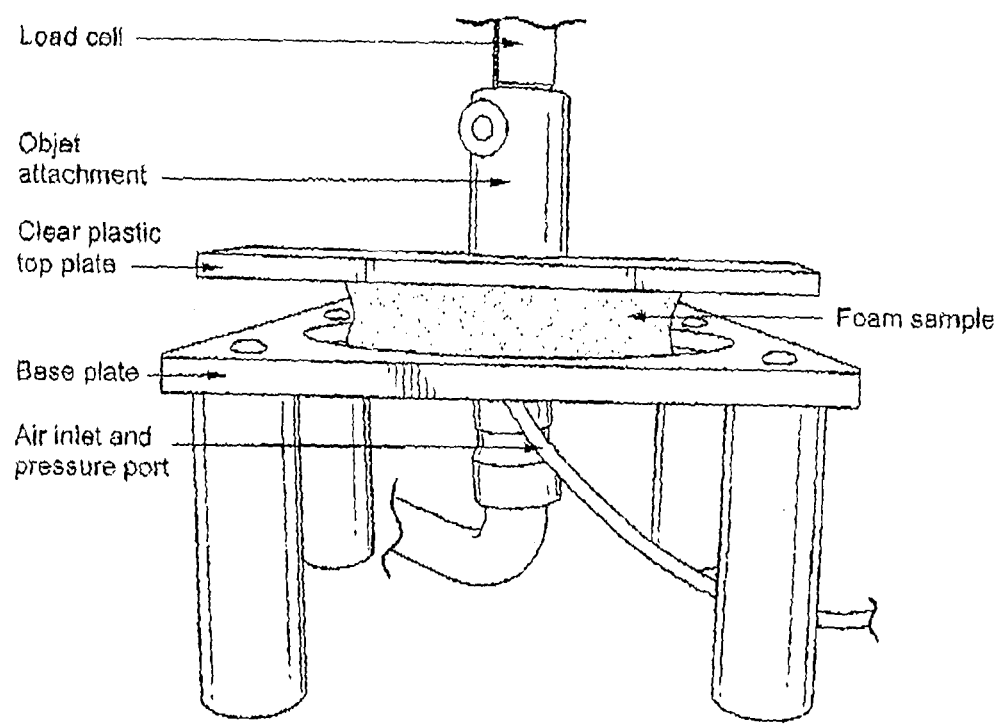

FIG. 7a shows an elevation view detail from the frame side of the interfacing structure 230 shown in FIG. 4e in a nasal bridge region. As shown in cross-section in FIG. 7b, it is apparent that the width w2 of the clip portion 234 is less than the width w1 of the cushion component 232 and that the outer perimeter of the clip portion 234 and the cushion component 232 are aligned. An advantage of this arrangement is illustrated in FIG. 7c where in use the nose is able to push the inner perimeter of the cushion component 232 in the direction shown by the arrow, in a cantilever manner as well as compressing. FIG. 8 is a cross-section showing the clip portion 234 of the interfacing structure 230 received within the channel 22 of a mask frame 20.

Figure 6A:
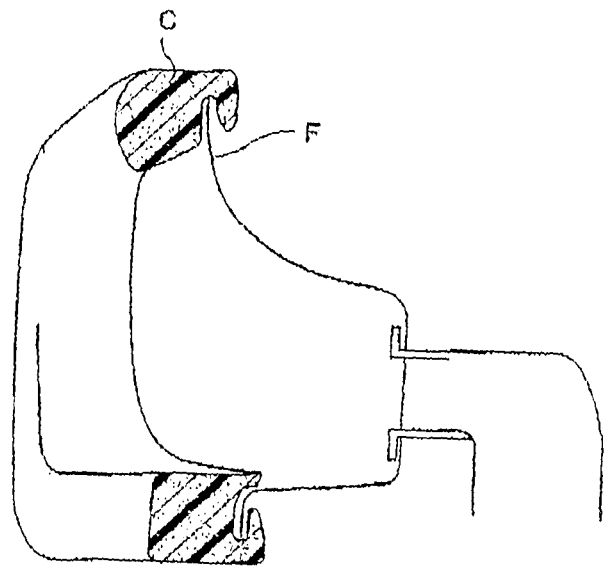
FIG. 6a shows a cross-section from a prior art nasal mask with foam cushion.
Figure 6B:
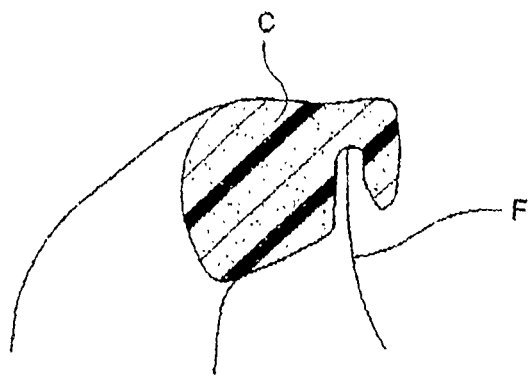
Figure 9A:
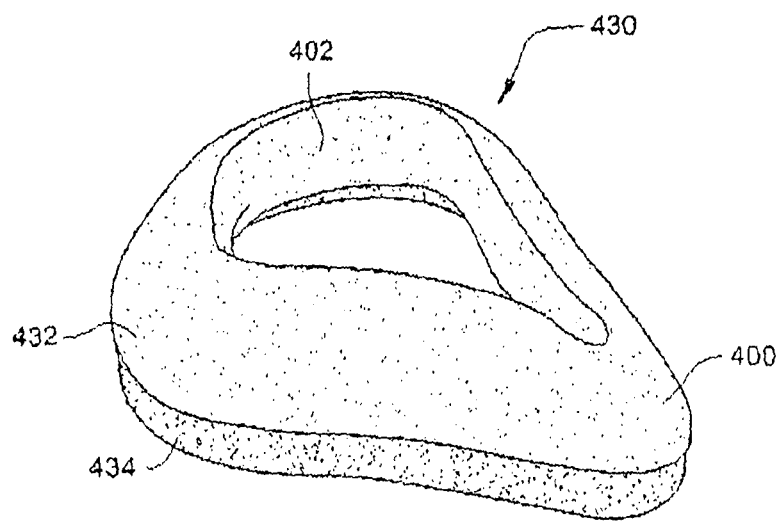
FIGS. 9a to 9d show various views of a foam-based interfacing structure according to an embodiment of the present invention.
Figure 9B:
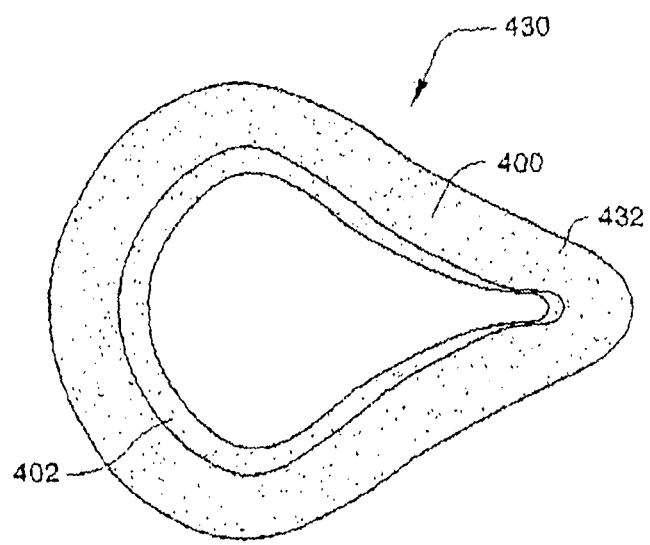
Figure 9C:
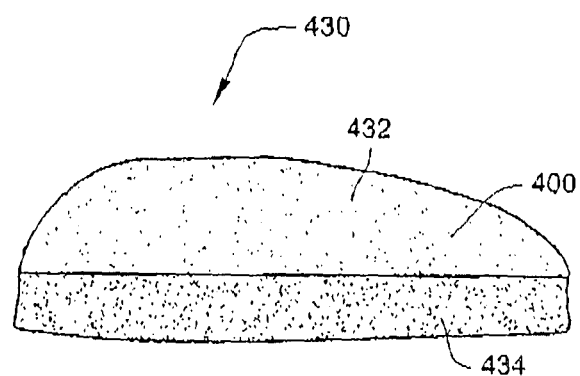
Figure 9D:
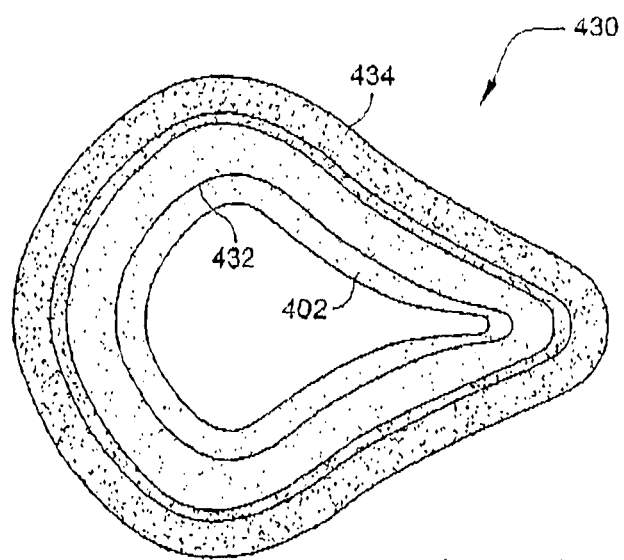

This arrangement is in contrast to prior art cushions (such as the Lifecare™ mask shown in FIGS. 6a and 6b) where the inner perimeter of the cushion C abuts the frame F, and hence it is not free to move inwardly and can only compress.

Figure 26:
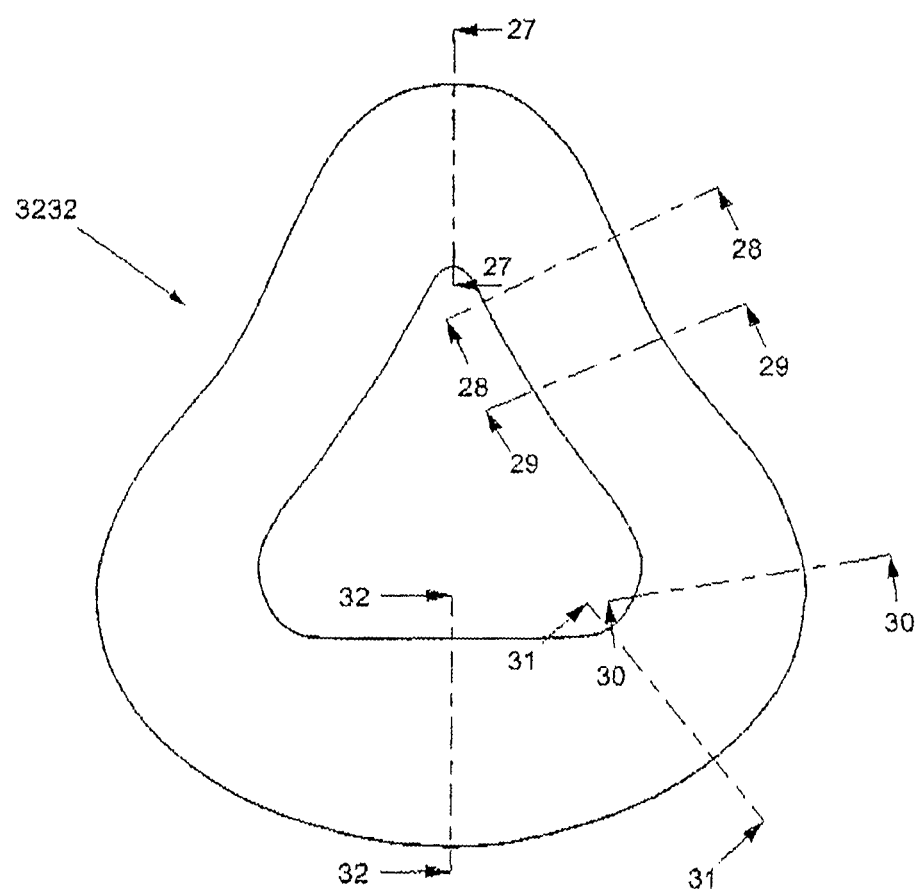
FIG. 26 is a front view of a further embodiment showing an interfacing structure for use with a full face mask including a cushioning component and clip portion.
Figure 27:
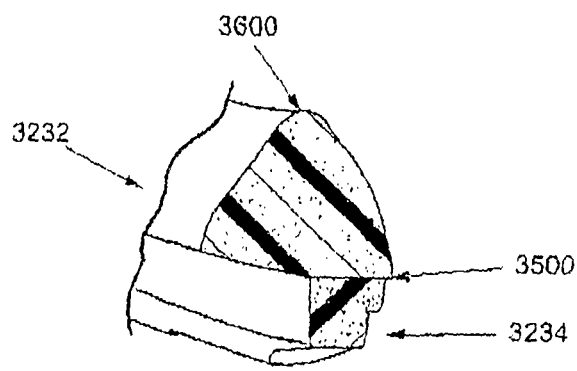
FIGS. 27-32 depict various cross-sectional views of the embodiment shown in FIG. 26.
Figure 28:
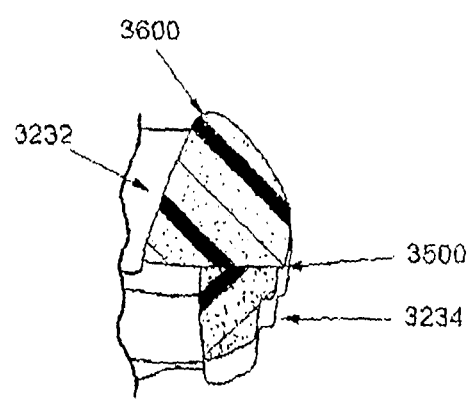
Figure 29:
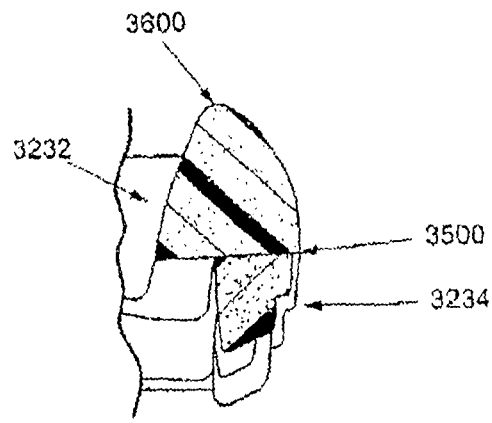
Figure 30:
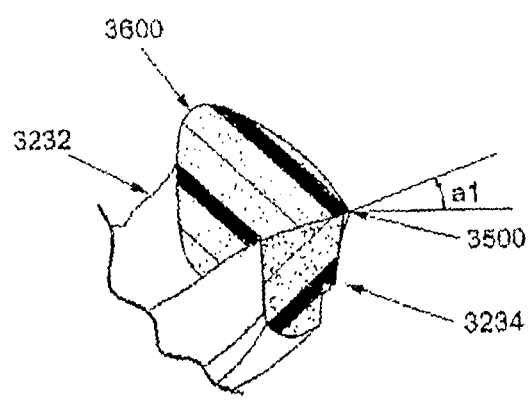
Figure 31:
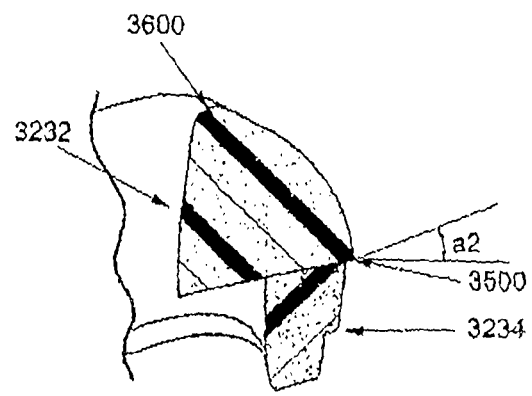
Figure 32:
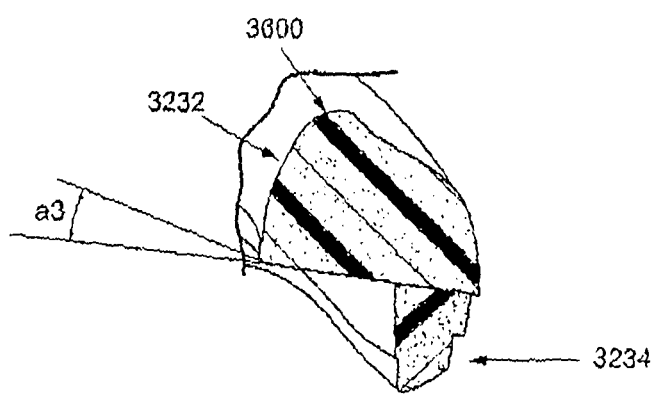
Figure 33:
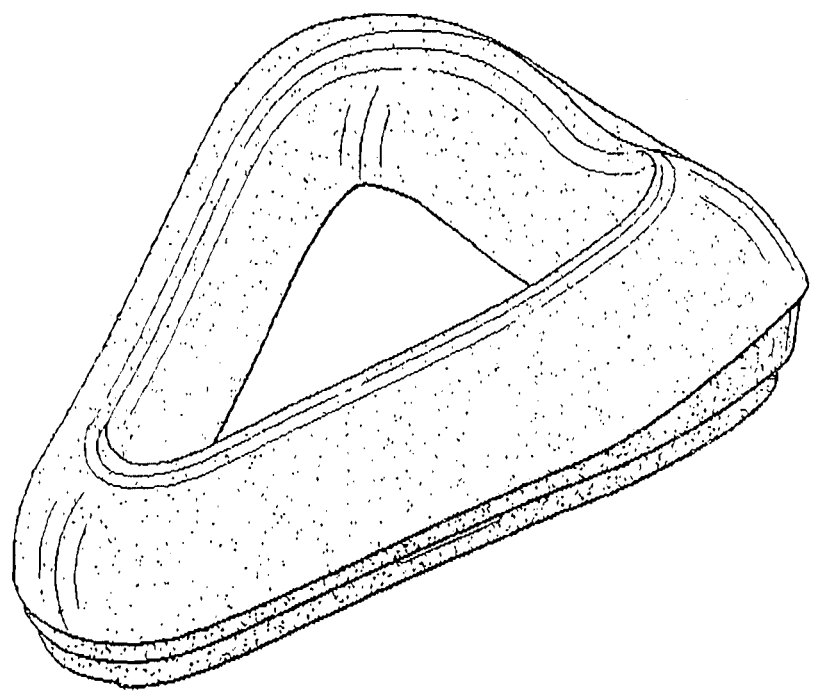
FIG. 33 is a perspective view of full face interfacing structure including a cushioning component and clip portion.
Figure 34:
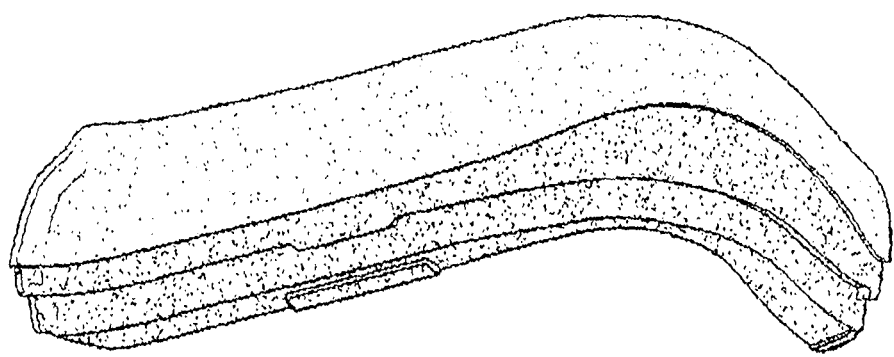
FIG. 34 is a side view of the embodiment shown in FIG. 33.
Figure 35:
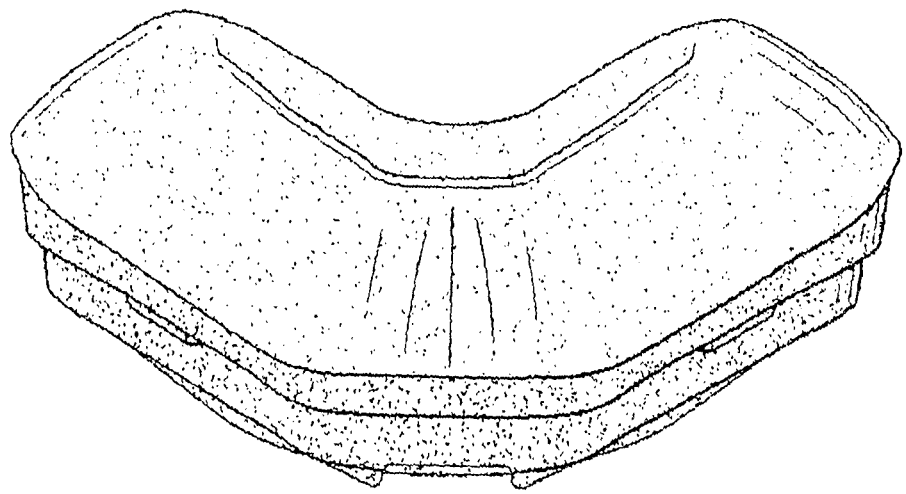
FIG. 35 is a top view of the embodiment shown in FIG. 33.
Figure 36:
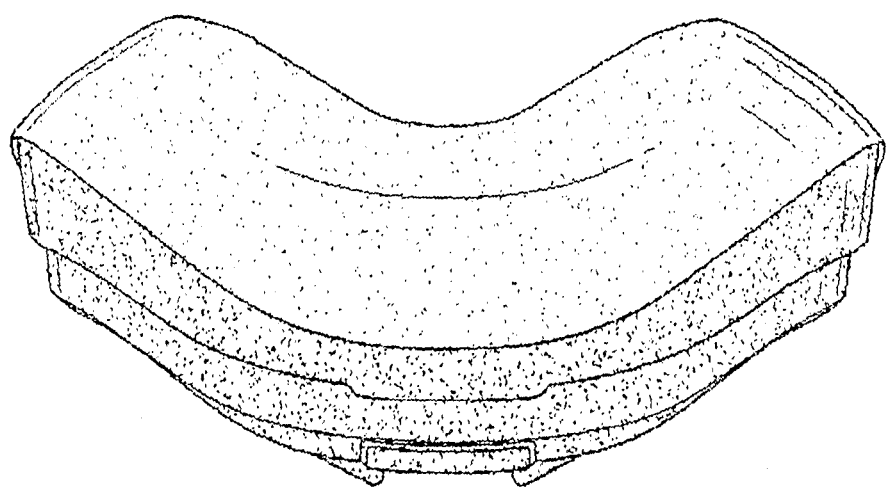
FIG. 36 is a bottom view of the embodiment shown in FIG. 33.
Figure 37:
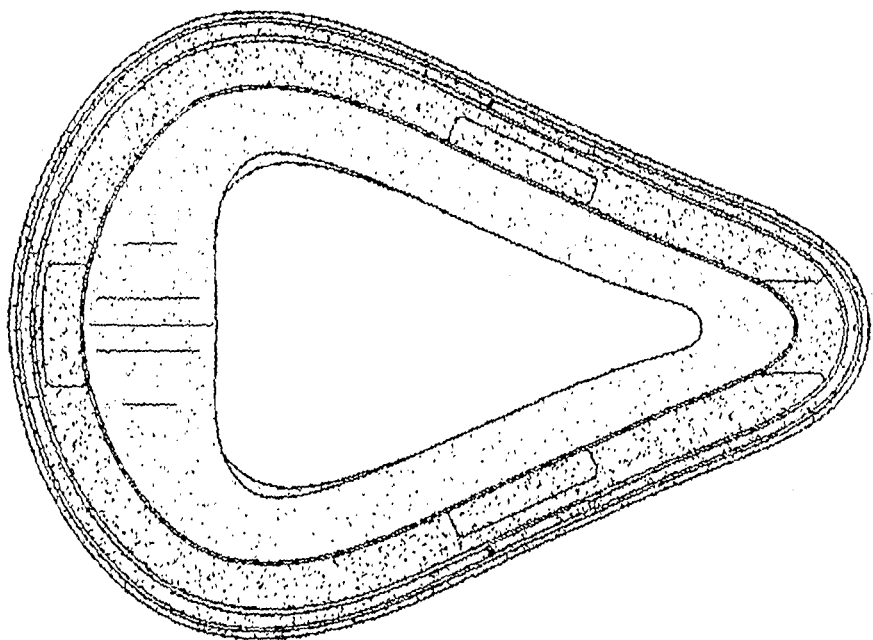
FIG. 37 is a back view of the embodiment shown in FIG. 33.
Figure 38:
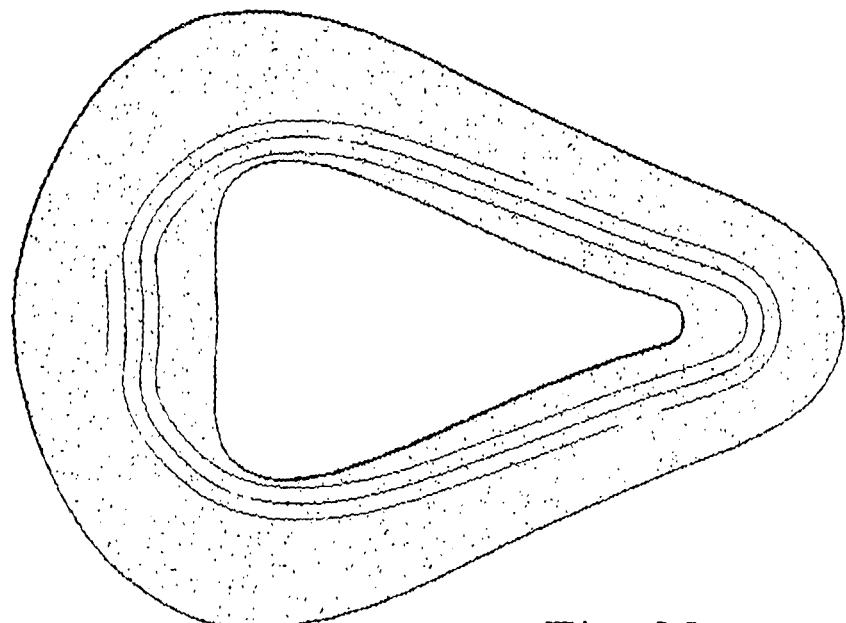
FIG. 38 is a front view of the embodiment shown in FIG. 33.

FIGS. 26-32 show an alternative embodiment of the present invention. FIG. 26 shows the cross sections later shown in FIGS. 27-32. Cushion component 3232 may be attached to clip component 3234. Cushion component 3232 may be similar to that shown in FIGS. 19-25. Clip component 3234 may have upper surface 3500 that attaches to cushion component 3232. Upper surface 3500 may be generally horizontal when in use or assembled, as shown in FIGS. 27, 28, and 29. In addition, this may position the tangent to apex 3600 of the cushion component 3232 generally parallel to upper surface 3500. Alternatively, upper surface 3500 may be generally curved or angled inwards towards the inner portion of the cushion so as to angle the cushion more towards the centre of the patient's face, as shown in FIGS. 30, 31, and 32. Therefore, tangent to apex 3600 may not be parallel to upper surface 3500. In an embodiment, the upper surface 3500 may be angled in one or more selected regions, e.g., lower cheek or chin regions to fit patients with more narrow, shallow faces (see FIGS. 30-32).

In an embodiment, as shown in FIGS. 27-32, the outer edge of the cushion component may slightly overhang (e.g., 1 mm overhang) the clip component, e.g., for manufacturability.

4.2 Glue

The two layers (i.e., the cushion component and the clip portion) may be adhered to one another using polyurethane hot melt glue or cyanoacrylate.

In alternate embodiments (not shown in Figures) the cushioning portion may be directly glued onto the frame.

4.3 Insert Molding

In a manufacturing process according to an embodiment of the present invention, insert molding may be used to assemble the cushioning component to the cushion-to-frame component. An advantage of this approach include lower cost when compared to other processes such as gluing.

FIGS. 17a to 17h illustrate a tool and manufacturing process for manufacturing an interfacing structure according to an embodiment of the present invention.

As best shown in FIG. 17a, the tool includes a first portion 1060 adapted to receive the cushioning component that may be cut from foam slabstock and a second portion 1065 adapted to receive the foaming mixture that will form the cushion-to-frame component.

The first portion 1060 of the tool may allow a vacuum to be applied to the cushioning component to retain it in position. For example, as shown in FIG. 17a, the walls of the cavity that receive the cushioning component include a plurality of orifices 1062, and a vacuum is applied to an opening 1063 in the side wall of the first portion 1060 so that the cushioning component may be drawn into the cavity. The first portion 1060 may be sized to provide an interference fit with the cushioning component.

The first and second portions 1060, 1065 of the tool are arranged so that there will be a region of contact between the cushioning component and the cushion-to-frame component such that they will adhere to one another.

At least a second portion of the tool is constructed and/or arranged to facilitate demolding of the cushion-to-frame component that would otherwise adhere to the tool. Preferably, this is achieved by using a tool constructed of a material from which the foam may be removed (e.g., high density polypropylene, silicone). Alternatively, steel or aluminum tools may be used, provided an appropriate de-molding agent can be used, such as wax (e.g., agent that does not present biocompatibility issues).

In the illustrated embodiment as best shown in FIG. 17a, the second portion 1065 includes three parts that are removably attached to one another, i.e., an inner portion 1066(1), and outer portion 1066(2), and a ring portion 1066(3).

An insert molding manufacturing process according to an embodiment of the invention will now be described in greater detail.

Figure 17C:
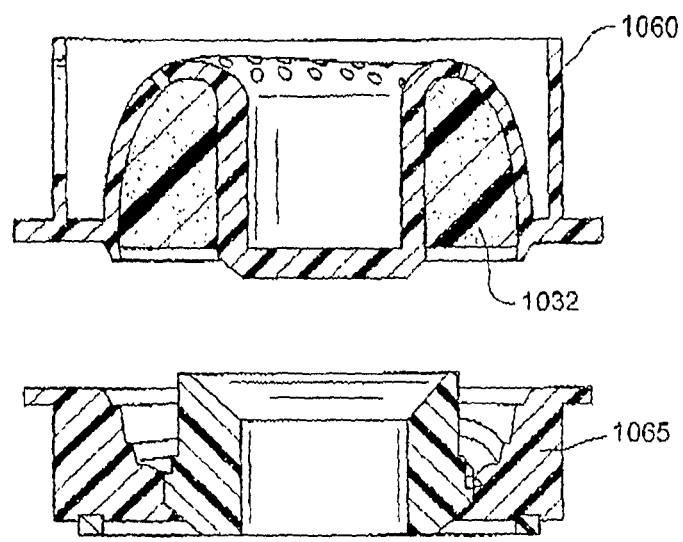

FIG. 17a illustrates the first and second portions 1060, 1065 of the tool separated from one another. In FIGS. 17b and 17c, the cushioning component 1032 is placed in the first portion 1060 of the tool. The cushioning component 1032 may be held in place in the first portion 1060 by a vacuum and may impart curvature on the cushioning component via the vacuum. This may be necessary if the cushion is made from a process that gives is a flat backed geometry. Placement of the cushioning component 1032 may be manual or automated. For example, the cushioning component 1032 may be sucked into the first portion 1060 using the vacuum.

Figure 17D:
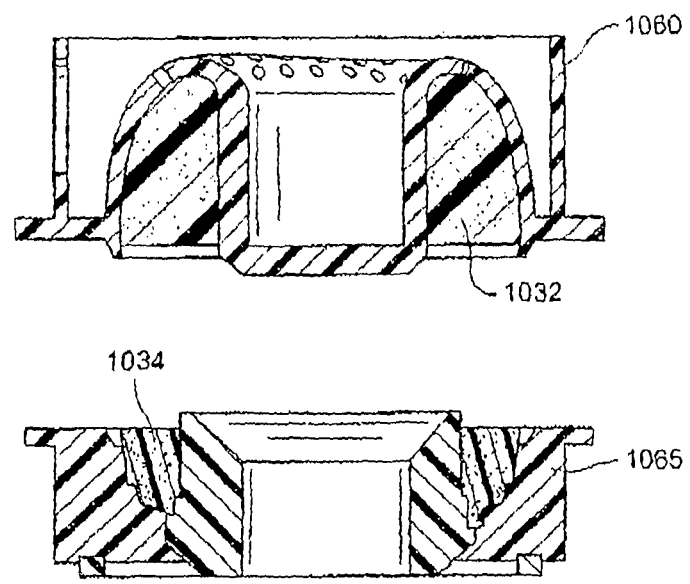

In FIG. 17d, a mixture of polyurethane (e.g., foam or elastomer) is prepared to form the cushion-to-frame component 1034 and the high-intensity mix is poured into the second portion 1065 of the tool. Pouring of the mix for the cushion-to-frame component 1034 may be manual or automated. If the cushion-to-frame component 1034 is made from a foam the cavity of the second portion 1065 will only be partly filled (e.g., 25%) and during the foaming process it will expand to fill the space and come into contact with the cushioning component where it will adhere.

Figure 17E:
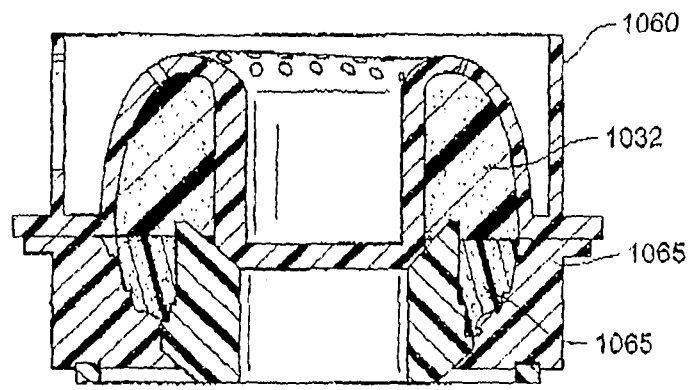

In FIG. 17e, the first and second portions 1060, 1065 of the tool are clamped together or closed to allow the cushion-to-frame component foaming reaction to proceed in the tool. That is, the foam for the cushion-to-frame component 1034 can rise up and chemically bond or adhere to the foam cushioning component 1032. The choice of clip material may enhance the bonding or adhesion process. In a preferred embodiment both the clip and the cushion are made from polyurethane material for ideal bond integrity between the two components. Additionally, should the cushion component have a regular, uniform, rough, irregular or non-uniform cell structure, the clip component may infuse into gaps in the cell structure of the cushion component, forming small mechanical bonds between the components.

Figure 17F:
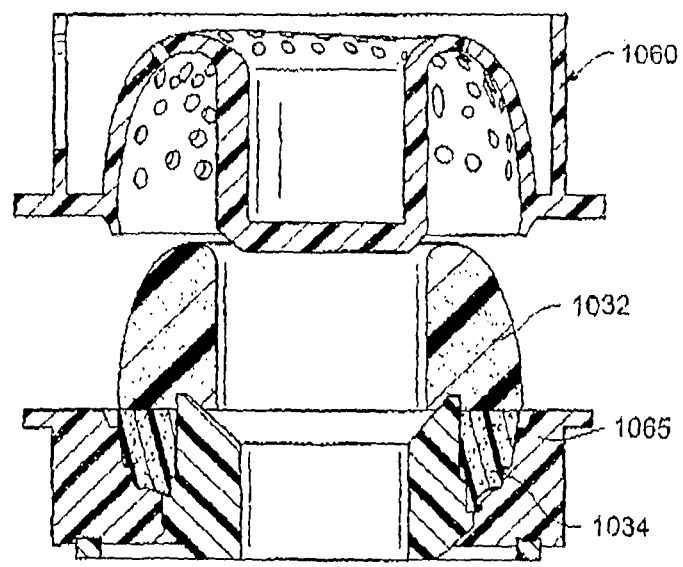
Figure 17G:
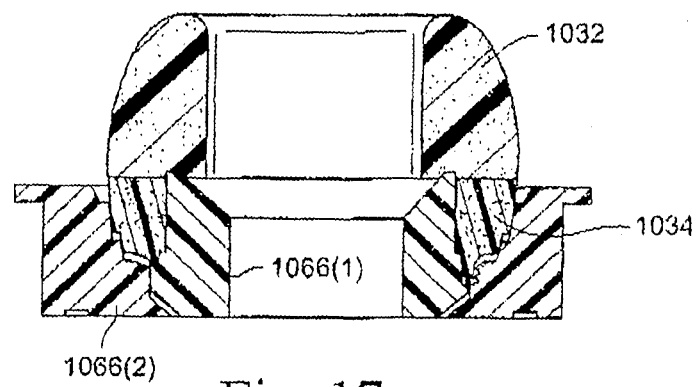
Figure 17H:
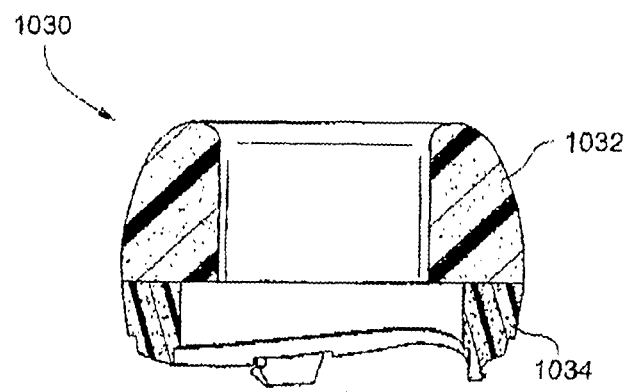

When the cushion-to-frame component 1034 has cured, the vacuum first portion and second portion are separated as shown in FIG. 17f. In FIG. 17g, the ring portion 1066(3) at the bottom of the second portion 1065 is removed and the inner portion 1066(1) is ejected to demold the cushion-to-frame component 1034. FIG. 17h shows the resulting interfacing structure 1030 removed from the tool with the cushioning component 1032 adhered to the cushion-to-frame component 1034. In a preferred embodiment the cushion component is originally flat when vacuum inserted into the top half of the tool and is bonded to a curved clip during the insert molding process. The resultant interfacing structure then assumes an intended curved shape.

In an alternative embodiment the cushion and clip are made flat but the cushion is made with sufficient depth to not require curvature to suitably adapt to the face when worn; but rather suitably deforms to the shape of the face due to the softness and depth of the cushion foam.

In another alternative arrangement, a film may be added to the second portion of the tool prior to the addition of the foaming mixture. This film may be structured to facilitate removal of the otherwise adhering cushion-to-frame component. The film may be used to form packaging for the interfacing structure.

In an embodiment, the clip portion of the interfacing structure may be constructed from more rigid and denser foam than the cushion component. For example, the clip portion may be formed from nitrogen blown polyethylene, or some other biocompatible foam having a fine cell-structure. Alternatively, the clip portion could be made from some other polymer or rubber. In an embodiment, the clip portion is adapted to form a cushion-to-frame engagement mechanism and to form a structural support for the cushion component.

Preferably, the cushioning component is less rigid, less stiff or more flexible than the clip portion, which is in turn less rigid, less stiff or more flexible than the frame of the mask. Preferably, the frame gives shape to the mask interfacing structure, wherein the interfacing structure is relatively flexible and less rigid, overall than the frame. This feature adds comfort and also allows the interfacing structure to be easily replaced by the patient or user. Further improvements to the interfacing structure may be made to adapt the shape and configuration to be disposable.

For example, FIG. 13 shows a clip portion 734 including a side 735 for interfacing with a foam-based cushion component and a side 737 for interfacing with a mask frame. In this embodiment, the clip portion 734 is constructed of a skinned foam and may be formed by molding. The foam of the clip portion 734 may be harder or more dense than the foam of the cushion component. Alternatively, the more dense or harder foam may be formed by cutting, e.g., die cutting, machining, and/or the methods set forth in AU 2008904769 and AU 2008904778.

This arrangement provides a one piece interfacing structure with a cushion component adapted to engage the patient's face and a clip portion adapted to interface with the mask frame.

In one form, a mask system may be provided that includes at least two different forms of interfacing structure chosen from the set of foam-based cushion, silicone-based cushion, and gel-based cushion.

FIGS. 14a to 16i illustrate an interfacing structure 930 including a cushion component 932 and a cushion-to-frame component or clip portion 934 provided to the cushioning component 932. FIGS. 14a to 14f show the cushioning component 932 attached to the cushion-to-frame component 934, FIGS. 15a to 15e are isolated views of the cushion-to-frame component 934, and FIGS. 16a to 16i are isolated views of the cushioning component 932.

As shown in FIGS. 14a to 15e, the cushion-to-frame component 934 includes a side 935 for interfacing with the cushioning component 932 and a side 937 for interfacing with a mask frame. The side 937 includes protrusions 938 to facilitate and/or enhance attachment to the mask frame.

5. Assembling the Frame and Interfacing Structure

The interfacing structure is constructed as described above and arranged for removable interconnection with the rest of the apparatus, for example a respiratory mask.

The ability to removably connect the interfacing structure enables one to replace the interfacing structure should it become soiled, damaged, uncomfortable or otherwise aged as a result of usage. It also facilitates trial or testing of different arrays of interfacing structures which are selected an different patients facial types or features (e.g., narrower face, longer nose, ox longer chin, etc.). One form of interfacing structure, for example a foam-based interfacing structure, may be used as a form of "training" system to allow a person to become accustomed to the sensation of wearing and using a mask. A foam-cushion based mask may provide an initially more appealing and comfortable surface for a new patient than a gel or silicone-based cushion. The patient may subsequently switch from the foam-based cushion to a silicone or gel based cushion. In this way, the patient may be more likely to adhere to therapy because they are used to the very soft comfortable feeling of foam.

When applied to respiratory equipment, the interfacing structure is adapted for connection with a mask frame. In use, a seal is formed between the interfacing structure and the frame. This arrangement could be used for both nasal and full-face masks. The seal between the frame and interfacing structure may seal better wherein the clip portion is less rigid or more flexible than the frame.

For example, FIG. 1 illustrates a mask 10 including a mask frame 20 a foam-based interfacing structure 30 provided to the mask frame 20. As illustrated, the foam-based interfacing structure 30 provides a foam cushion component 32 adapted to contact the patient's face in use. In this embodiment, the foam-based interfacing structure 30 is adapted for use with an existing mask (e.g., ResMed's Mirage Quattro mask), which allows the patient to switch from the foam-based interfacing structure 30 to the mask's existing silicone-based cushion if desired.

FIGS. 4a to 4g show a foam-based interfacing structure 230 according to an embodiment of the invention. As illustrated, the interfacing structure 230 includes a cushion component or face-contacting portion 232 and a clip portion 234 provided to the cushion component 232. In this embodiment, the clip portion 234 is adapted for an interference fit with a mask frame, and the width of the clip portion 234 is narrower than the width of the cushion component 232 (e.g., see FIGS. 4e and 4g).

5.1 Cushion-to-Frame Engagement Mechanisms

According to an aspect of the invention, the cushion-to-frame engagement and connection mechanism provided by the clip portion may include a channel-type engagement or rib-type engagement.

Figures 1, 50:
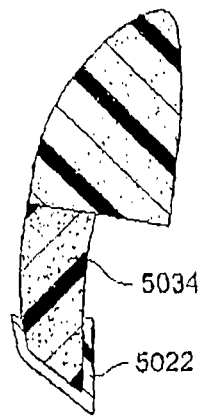
Figures 2, 50:
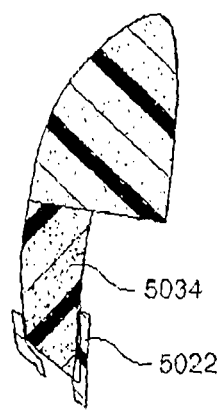

As shown in FIG. 2, the channel-type engagement includes a foam clip portion 34 that is adapted to be received within the channel 22 of a mask frame 20 with an interference fit. The foam clip portion 34 extends around the entire perimeter of the interfacing structure so as to form a seal and retention with the mask frame.

As shown in FIGS. 3a to 3c, the rib-type engagement includes a foam clip portion 34 with one or more slots 38 to receive inner and/or outer ribs 23, 24 of the mask frame 20. For example, the slot to rib engagement may provide an inner frame rib engagement (see FIG. 3a), an outer frame rib engagement (see FIG. 3b), or an inner and outer frame rib engagement (see FIG. 3c). This arrangement provides a broader base of support for the sealing foam.

Figure 5A:
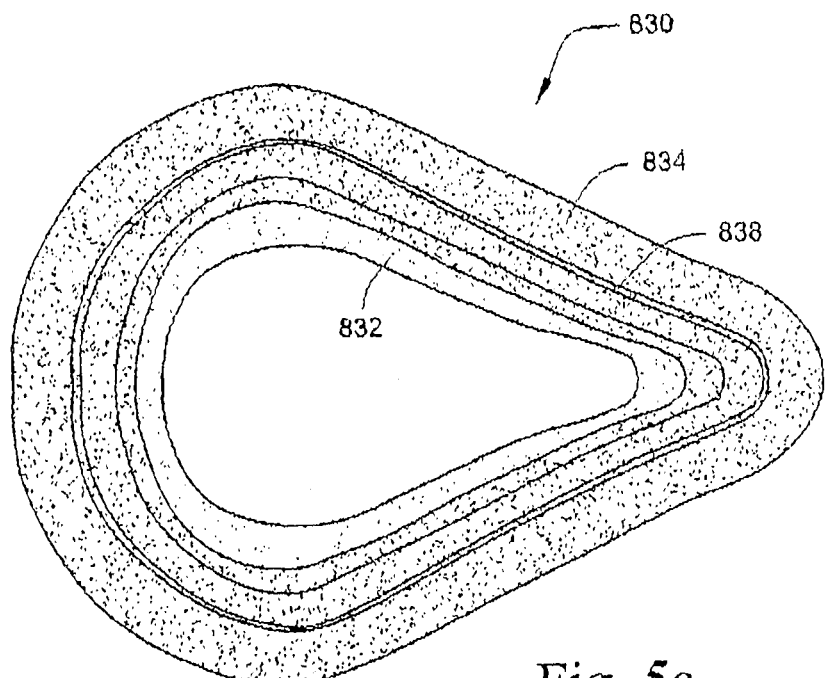
FIG. 5a is a plan view showing a die cut interfacing structure wherein the clip portion includes a slot for engagement with the frame according to an embodiment of the invention.
Figure 5B:
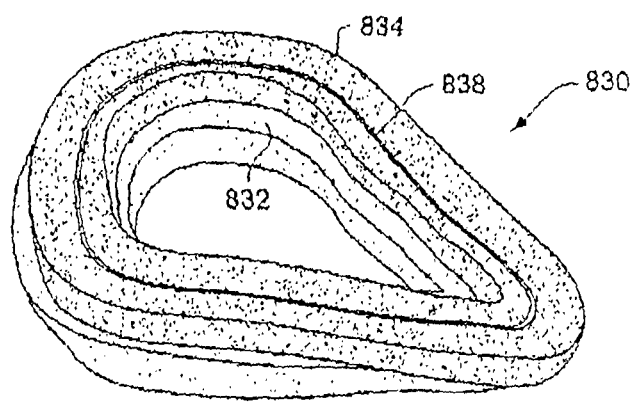
Figure 5C:
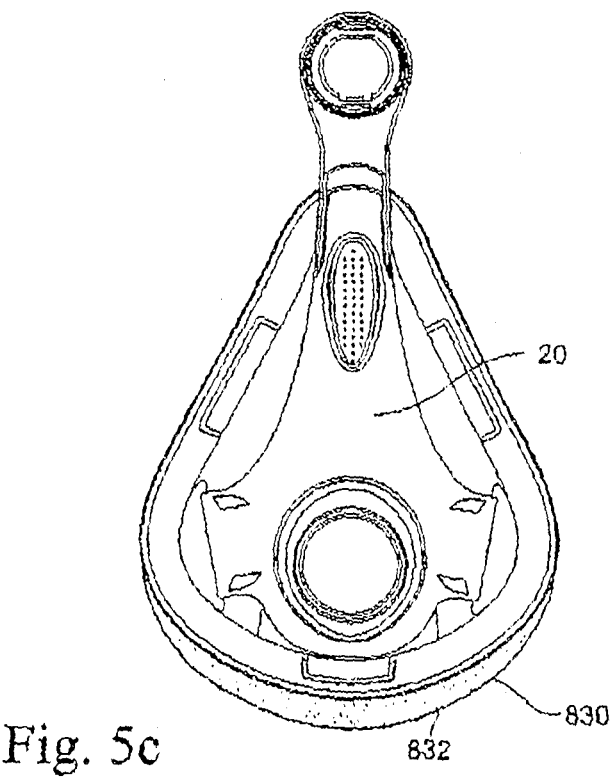
FIG. 5c is an assembly view of the interfacing structure shown in FIG. 5a with a mask frame.

FIGS. 5a and 5b illustrate a foam-based interfacing structure 830 including a foam cushion component 832 and a clip portion 834, and FIG. 5c illustrates the interfacing structure 830 provided to a mask frame 20. As shown in FIGS. 5a and 5b, the clip portion 834 includes a slot 838 adapted to receive a rib of the mask frame 20. Also, providing a wider clip portion 834 allows more stiffness and structural integrity to be provided to the clip portion, making the clip portion easier to assemble to the mask frame.

When structured to form an interference fit with the mask frame, the clip portion may have the following properties: appropriate rigidity (e.g., less than that of the frame and in one form more rigid than the foam cushion component); non-porous; and/or low compression set (the amount of deformation expressed as a percentage of original dimensions) which a material retains after compressive stress is released (in this way, the clip portion maintains its retention force during its usage life).

Additionally, the clip portion may include an additional extension (not shown) that extends beyond the outer extremity of the frame which is adapted to be gripped by the patient for easier removal of the interfacing structure. Preferably, this extension would be positioned in a region that is easy for the patient to grip such as the nasal bridge of the mask. Preferably, the extension will be small enough not to impede vision of the user or to affect the overall efficiency or seal of the mask. Preferable, the extension may function as a finger grip for the patient to remove or replace the interfacing structure, when desired.

Figures 1, 51:
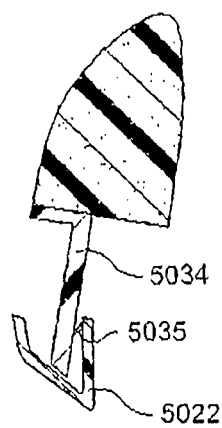
Figures 2, 51:
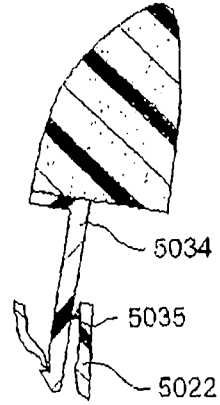
FIG. 2 shows a schematic diagram of a channel of a portion of a mask frame and a clip portion of an interfacing structure retained by an interference fit according to an embodiment of the invention.
Figures 1, 56:
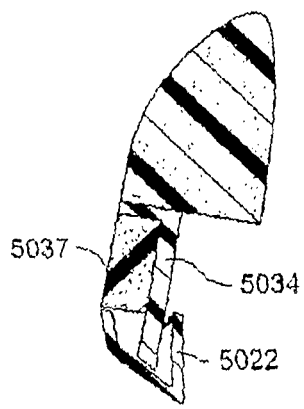
Figures 2, 56:
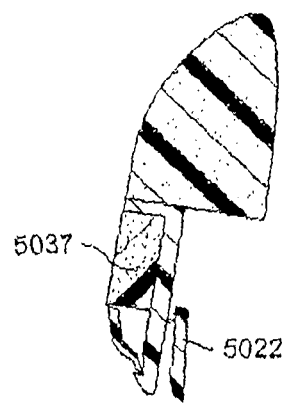
Figures 1, 57:
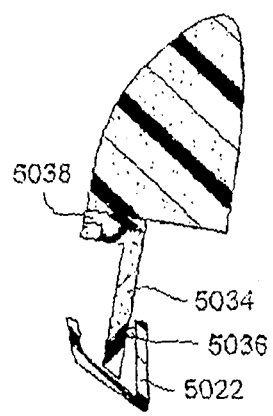
Figures 2, 57:
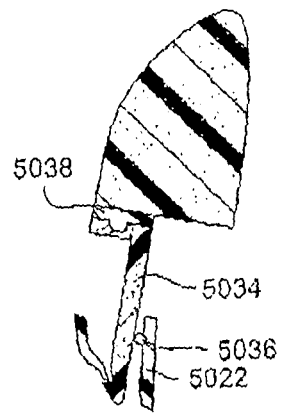

FIGS. 50-1 to 57-2 illustrate alternative mechanisms for attaching the clip portion to the frame. In FIGS. 50-1 and 50-1, the clip portion 5034 is in the form of a microcellular polyurethane clip adapted to engage within the frame channel 5022 with an interference fit. In FIGS. 51-1 and 51-2, the clip portion 5034 is in the form of a flexible plastic clip (e.g., Hytrel, TPE) adapted to engage the frame channel 5022 with a snap fit. The clip portion also includes a lip seal 5035 adapted to engage the channel wall. In FIGS. 52-2 and 52-2, the clip portion 5034 is in the form of a flexible plastic clip adapted to engage the frame channel 5022 with a snap fit. The clip portion also includes a sealing element 5035 (thermoplastic elastomer that may be over molded on to the clip portion) adapted to engage the channel wall. In FIGS. 53-1 and 53-2, the clip portion 5034 is in the form of a polyurethane clip adapted to engage within the frame channel 5022 with an interference fit. The clip portion also includes a flexible plastic clip 5036 (assembled to the polyurethane clip) adapted to engage the frame channel with a snap fit. In FIGS. 54-1 and 54-2, the clip portion 5034 is in the form of a polyurethane clip adapted to engage within the frame channel 5022 with an interference fit. The clip portion also includes a flexible plastic clip 5036 (glued to the polyurethane clip) adapted to engage the frame channel with a snap fit. In FIGS. 55-1 and 55-2, the clip portion 5034 includes a flexible plastic clip adapted to engage the frame channel 5022 with a snap fit or other fitting means e.g. interference fit. In addition, the clip is contoured such that the clip also engages the channel wall with an interference fit. In FIGS. 56-1 and 56-2, the clip portion 5034 includes a flexible plastic clip adapted to engage the frame channel with a snap fit. The clip portion also includes a foam element 5037 adapted to cover the clip. In FIGS. 57-1 and 57-2, the clip portion 5034 includes a polyurethane clip (attached to cushion component by plastic element 5038) adapted to engage the frame channel 5022 with a snap fit. The frame channel includes a plastic extension 5023 adapted to engage the clip. This arrangement allows replacement of the cushion component without the need to change the clip portion.

6. Exemplary Materials and Properties

The following provides exemplary materials and properties of the cushion component and clip portion.

6.1 Cushion Component

In an embodiment, the cushion component may be made from polyurethane, be resistance to hydrolysis and/or resistant to microbial attack.

In an embodiment, the cushion component may be air permeable. In an embodiment, the cushion component may not be air permeable.

In an embodiment, the cushion component may be able to maintain its air permeability over a period of use.

Preferably, the cushion component may not emit harmful or odorous volatiles or particulates.

Preferably, the cushion component may be coloured and this colour may not fade.

FIG. 48 is a chart showing exemplary material properties for the cushion component.

In one example, properties of the foam cushion component may include: density (relates to other foam properties and affects cost and weight of the cushion, e.g., higher density can reduce air permeability and higher density can increase hardness); air permeability (flow of air through cushion contributes to total mask flow characteristic of the mask which may affect compatibility with PAP devices); hardness (affects comfort and sealing performance); tear resistance (contributes to durability); tensile strength (contributes to durability); and/or tensile stiffness (resists the deforming effects of positive air pressure inside the mask).

6.2 Clip Portion

FIG. 49 is a chart showing exemplary material properties for the clip portion.

In one example, properties of the foam clip portion may include: density (affects weight); air permeability (permeability of the foam itself may not be critical if it is molded with a skin that renders it impermeable); hardness (soft and flexible enough to assemble to the frame with an interference fit and seal against the frame); elasticity/viscoelasticity (soft and flexible enough to assemble to the frame with an interference fit and seal against the frame); and/or compression set (should not deform over time to ensure easy assembly/retention).

6.3 Testing Methods

The following provides exemplary testing methods for determining material properties.

6.3.1 Air Permeability

Air permeability is defined as "the rate of air flowing through a foam sample (in L/min)".

This test measures the flow through a regular shape with a constant cross section, in a manner analogous to a cushion in real use. In the example of FIG. 60-1, the test specimen is an annulus of foam, about 30 mm thick. The circular shape ensures that pressure is evenly distributed and the foam inflates uniformly.

The foam sample is cut normal to cell rise direction as shown in FIG. 60-4.

Figures 1, 63:
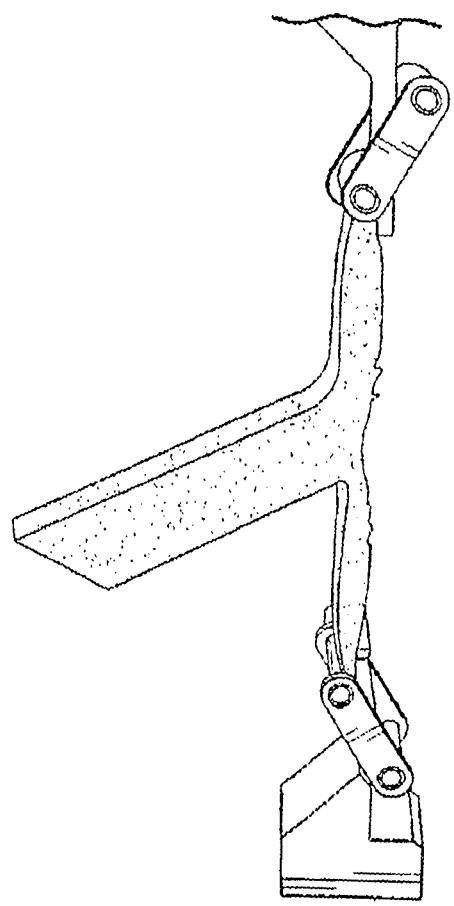
Figures 2, 63:
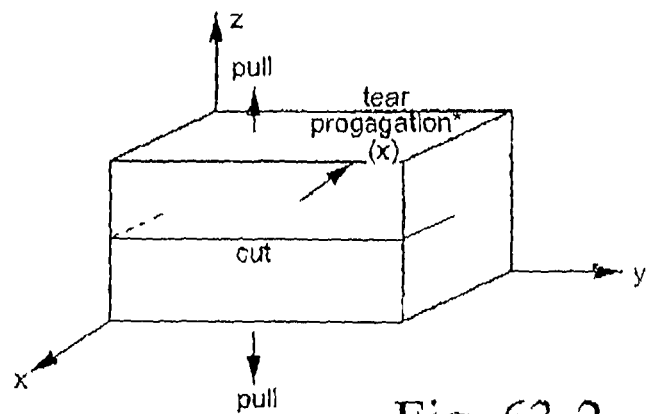
Figures 3, 63:
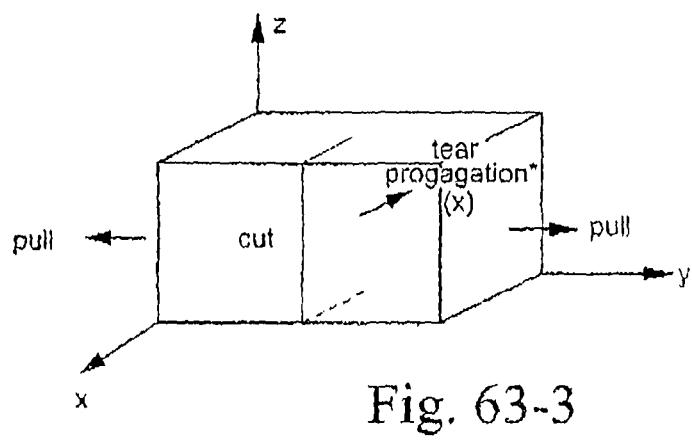
Figures 4, 63:
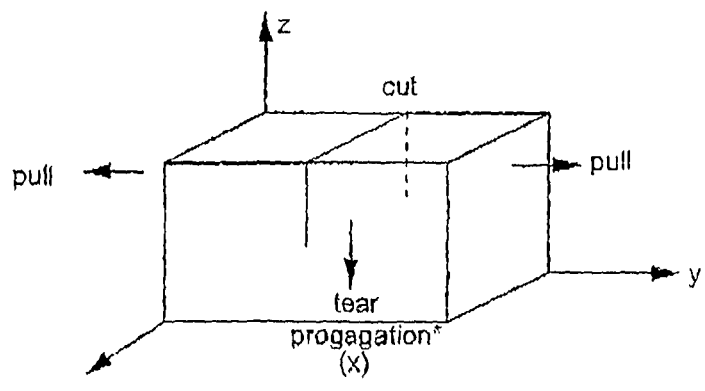

The wall section of the foam specimen may be rectangular (see FIG. 60-2), but it is possible for the wall section to have a concave outer surface and a convex inner surface (see FIG. 60-3).

The annular foam sample is held at a defined height between two plates in a Universal Test Machine (e.g., Instron). Air at a given pressure is directed into the centre of the annulus and flows out through the foam. The air flow rate and reaction force of the foam against the plates may be measured. FIG. 60-5 is a schematic of the test set up.

As shown in FIGS. 60-6, 60-7, and 60-8, the test jig used to hold the foam consists of: an aluminum base plate that locates the foam and seals against the flat bottom surface of foam annulus; an air inlet and pressure port in the centre of the base plate; a clear polycarbonate top plate that seals against the flat bottom surface of foam annulus and allows observation of the test sample; and a part glued to the top plate to connect with a load cell attachment on the Universal Testing Machine (UTM).

Once set up, attach the top plate to the crosshead of the UTM, zero the load cell of the UTM.

Zero the displacement of the UTM at the uncompressed height of the foam sample, i.e., 30 mm above the base plate sealing surface.

If there is variation of 1 mm or more in the thickness of the samples, then for each sample: (i) assemble the foam sample into the test jig; (ii) lower the crosshead just until a positive force is read on the UTM, e.g., 0.2 N; and (iii) zero the displacement.

Lower the crosshead at 50±20 mm/min until 40% compression displacement is reached.

Immediately record the reaction force, at 0 cmH$_2$O.

Wait 60 seconds and again record the force.

Immediately but gradually adjust the flow generator to 4 cmH$_2$O (and immediately record force and flow rate.

Wait 60 seconds and again record the force and flow rate.

Repeat steps 7 and 8 for 12 cmH$_2$O and 20 cmH$_2$O.

6.3.2 Hardness

Hardness is defines as "force required to indent a test piece of foam to a stated percentage of its original thickness".

Figure 61:
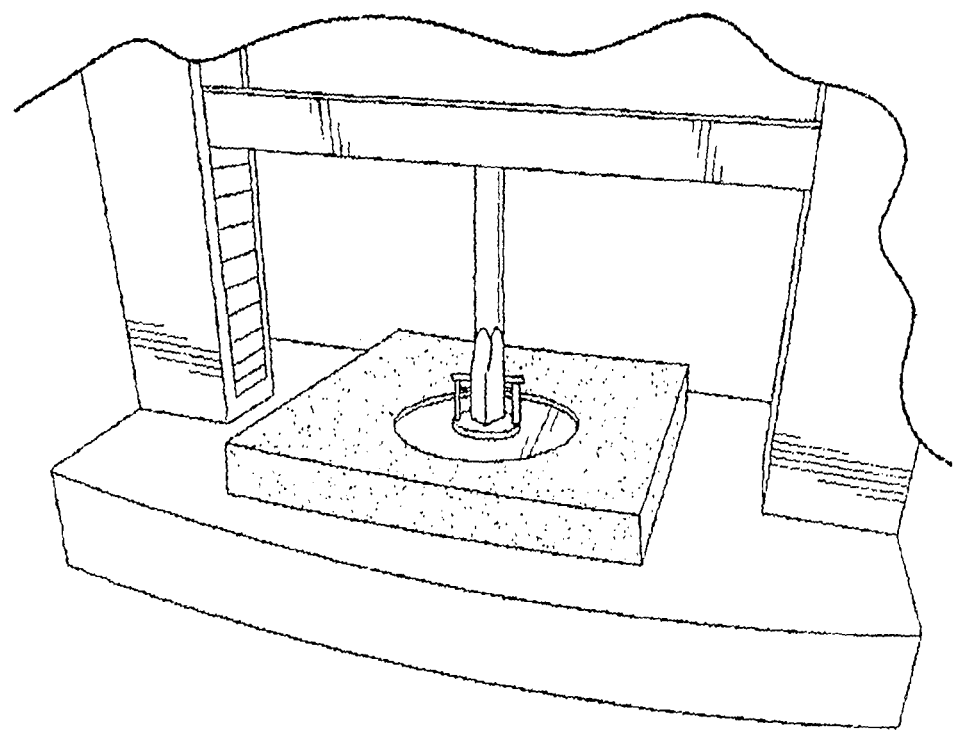
FIG. 61 illustrates apparatus for testing hardness according to an embodiment of the invention.

Hardness may be tested using an IDM Universal Test Machine, or equivalent (e.g., see circular flat indenter of FIG. 61)

If applicable, precondition the foam as specified in AS 2282.2-1999.

Test the foam according to AS 2282.8-1999 Method A—Indentation force on deflection test.

Report IF$_{40}$, the reaction force at 40% compression after 60 seconds indentation, H60s.

Also report the reaction force at 40% compression after 2 seconds indentation, H2s.

Report the sag factor or support factor, i.e., the ratio of 65% to 25% IFD value.

6.13 Tensile Strength

Tensile strength may be measured using an IDM Universal Test Machine, or equivalent. See FIG. 62-1.

Test both directions, i.e., parallel to and normal to the direction of cell rise.

Apply the following deviations from AS 2282.6-1999:

Do not reject test pieces that break outside the gauge length.

Record whether the test piece did break, did not break or came out of the jaws before maximum elongation was reached.

Three test pieces may be acceptable if the results are consistent (no individual value deviates more than 20% from the mean of the three values).

Select a typical or representative results curve by inspecting the graphs. Select a suitably linear region near the start of the curve. (The start of the curve is more representative of real use than an extremely stretched region and also ensures the result is not affected by the test sample sliding out of the gripping jaws.)

Calculate the change in force over a distance of at least 25 min and divide by the distance to obtain the stiffness value in N/mm.

Figures 1, 62:
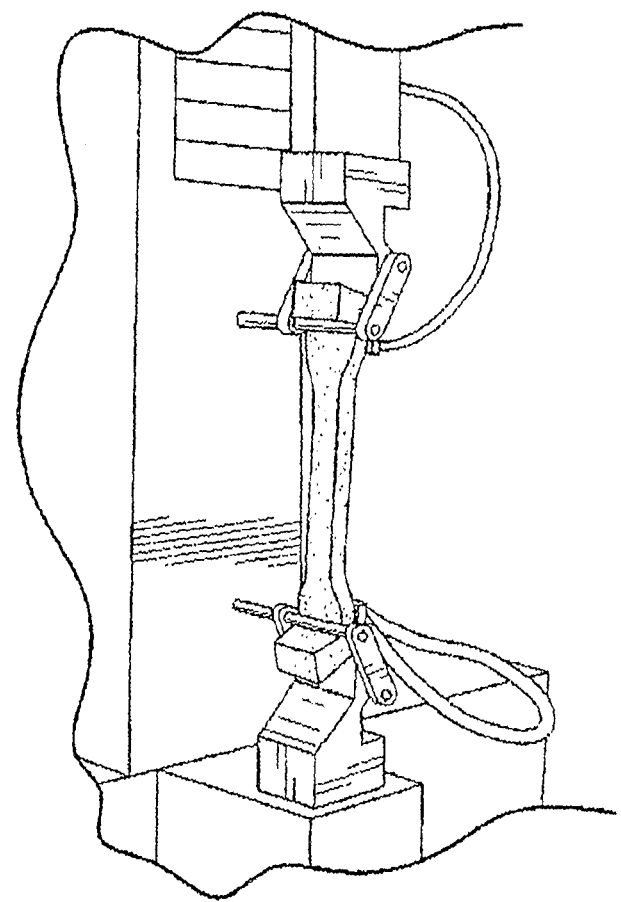
Figures 2, 62:
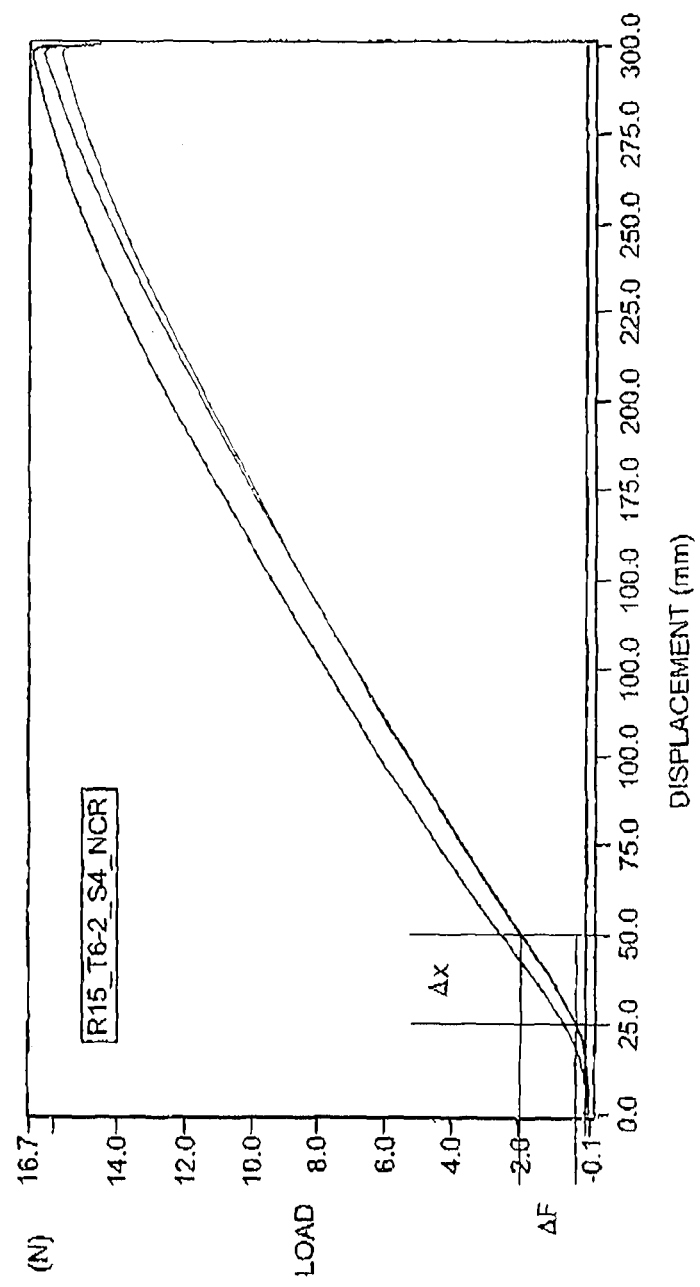

For example, the curve in FIG. 62-2 is most linear near the start of the curve, between 25 mm and 50 mm. Stiffness was calculated as follows.

$$k_{tensile} = \Delta F / \Delta x = (F_{50\ mm} - F_{25\ mm})/(50-25)$$

6.3.4 Tear Resistance

Tear resistance is defined as the force required to propagate a tear in a pre-cut sample. See FIG. 63-1.

Test according to AS 2282.7-1999 with the following parameters:

The speed of separation of the jaws holding the test piece shall be 200 mm/min.

Test all three directions defined in FIGS. 63-2, 63-3, and 63-4. Test and report the tear resistance results ($\sigma_t$) for each direction separately.

Apply the following deviations from AS 2282.7-1999;

Do not use a knife or blade to assist the direction of tear. Allow the foam to tear naturally.

It may not be possible to tear a 50 mm length of foam. Tear as far as possible up to 50 mm.

Total Mask Flow

Figure 64:
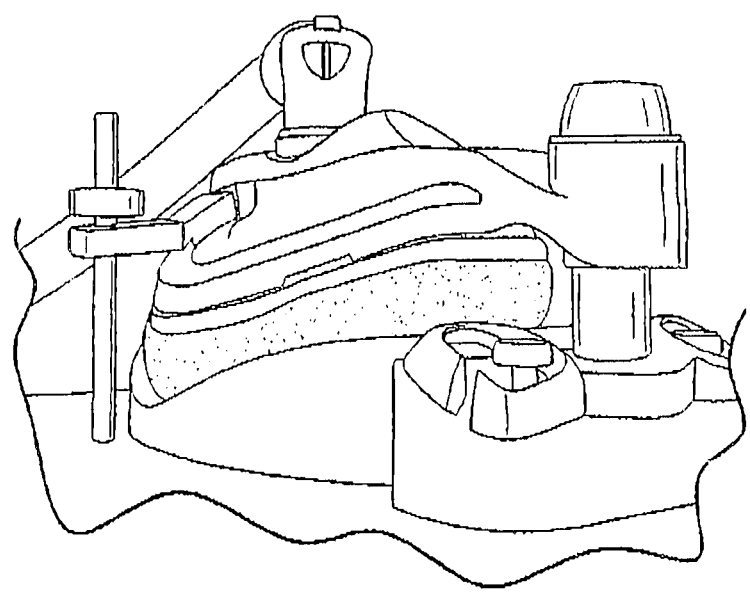
FIG. 64 illustrates apparatus for testing total mask flow according to an embodiment of the invention.

This test measures the flow through only the foam cushion, by blocking the mask vent all other leak paths. See FIG. 64.

The cushion is compressed by 40% of its 30 mm thickness, i.e., 12 mm.

7. Other Features

In an embodiment, a mask frame may be integrally molded or formed with the cushion-to-frame component 1034. For example, the second portion 1065 of the tool may be structured to mold the cushion-to-frame component together with the mask frame.

In the illustrated embodiment, a polyurethane foam cushioning component is provided to a polyurethane foam or polyurethane elastomer cushion-to-frame component. In an alternative embodiment, one or both of the components may be constructed of a gel material. For example, both components may be constructed of gel, the cushioning component may be constricted of gel and the cushion-to-frame component may be constructed of foam, or the cushioning component may be constructed of foam and the cushion-to-frame component may be constructed of gel.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. For example the cutting techniques used for the cushioning component may also be used for the clip component, or the interfacing structure. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A cushioning component for use with a mask including a frame or clip portion, wherein at least a portion of a cross section of the cushioning component comprises:

an inner side defined by a side facing the centre of the mask;

an outer side defined by a side facing away from the centre of the mask; and a base side facing the frame or clip portion, wherein the cross section of the cushioning component has a generally triangular shape, wherein the inner side and the outer side converge at an apex of the triangle, the apex being formed at least in part from foam and being configured to contact a patient's skin to form a seal therewith, and wherein the length of the outer side is greater than the length of the inner side.

2. The cushioning component according to claim 1, wherein the inner side, the outer side and the base form an entire outer boundary of the cross section.

3. The cushioning component according to claim 1, wherein the cross section is located at a nasal bridge region of the cushioning component.

4. The cushioning component according to claim 1, wherein the cross section is located at a lip region or a chin region of the cushioning component.

5. The cushioning component according to claim 1, wherein the inner side and the outer side meet at a portion of the cross section that is a radius.

6. The cushioning component according to claim 1, wherein the apex is offset from a center line of the base side towards the centre of the mask.

7. The cushioning component according to claim 6, wherein a distance of the offset is two different values at two different locations of the cushioning component.

8. The cushioning component according to claim 7, wherein the two different locations are an area configured to contact a nose of a user and an area configured to contact a lower lip of the user.

9. The cushioning component according to claim 1, wherein the outside surface further comprises at least an upper and a lower portion, the upper portion being at a reduced angle in comparison to the lower portion.

10. The cushioning component according to claim 1, wherein at least a portion of the cushioning component is configured to rotate towards the centre of the mask when pressure is applied to the cushioning component by the patient's face.

11. The cushioning component according to claim 1, wherein the inner and outer sides of the cushioning component taper together at an acute angle.

12. The cushioning component according to claim 1, wherein the cross-section of the cushioning component tapers from a wider cross-section to a narrower cross-section closer to the apex area.

13. The cushioning component according to claim 1, wherein the apex has a rounded cross sectional profile.

14. The cushioning component according to claim 1, wherein the cushioning component is configured to form a compression-type seal with the patient's skin.

15. A method of manufacturing a cushioning component for use with a mask including a frame or clip portion, the method comprising:

forming an inner side defined by a side facing a centre of the mask;

forming an outer side defined by a side facing away from the centre of the mask; and forming a base side configured to face the frame or clip portion when the cushioning component is worn by a patient, wherein the length of the outer side is greater than the length of the inner side, and wherein the inner side, the outer side and the base side are portions of a cross section of the cushioning component wherein the cross section of the cushioning component has a generally triangular shape, and wherein the inner side and the outer side converge at an apex of the triangle, the apex being formed at least in part from foam and being configured to contact a patient's skin to form a seal therewith.

16. The method according to claim 15, wherein the cushioning component is formed from unskinned foam.

17. The method according to claim 15, wherein the cushioning component is formed by cutting foam.

* * * * *